US007060277B2

(12) United States Patent
Kaempfer et al.

(10) Patent No.: US 7,060,277 B2
(45) Date of Patent: Jun. 13, 2006

(54) BROAD SPECTRUM ANTAGONISTS AND VACCINES DIRECTED AGAINST PYROGENIC EXOTOXINS

(75) Inventors: Raymond Kaempfer, Jersualem (IL); Gila Arad, Jersualem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 327 days.

(21) Appl. No.: 10/172,425

(22) Filed: Jun. 13, 2002

(65) Prior Publication Data

US 2003/0147908 A1 Aug. 7, 2003

Related U.S. Application Data

(63) Continuation-in-part of application No. 09/150,947, filed on Sep. 10, 1998.

(30) Foreign Application Priority Data

Dec. 30, 1996 (IL) .................................... 119938
Dec. 30, 1997 (WO) ..................... PCT/IL97/00438

(51) Int. Cl.
*A61K 39/00* (2006.01)
*A61K 39/02* (2006.01)
*A61K 39/38* (2006.01)
*A61K 38/385* (2006.01)
*C07K 14/00* (2006.01)

(52) U.S. Cl. ................ 424/184.1; 424/185.1; 424/193.1; 424/234.1; 424/235.1; 424/236.1; 424/237.1; 424/244.1; 530/300; 530/350

(58) Field of Classification Search ............. 424/184.1, 424/185.1, 193.1, 234.1, 235.1, 236.1, 237.1, 424/244.1; 530/300, 350
See application file for complete search history.

(56) References Cited

U.S. PATENT DOCUMENTS

| | | | |
|---|---|---|---|
| 5,310,874 A | | 5/1994 | Tamura et al. |
| 5,407,609 A | * | 4/1995 | Tice et al. .................... 264/4.6 |
| 5,705,151 A | | 1/1998 | Dow et al. |
| 5,716,637 A | * | 2/1998 | Anselem et al. ............. 424/450 |

FOREIGN PATENT DOCUMENTS

WO WO 98/29444 7/1998

OTHER PUBLICATIONS

Abrahmsén, et al., "Characterization of two distinct MHC class II binding sites in the superantigen staphylococcal enterotoxin A", The EMBO Journal, vol. 14, No. 13, pp. 2978-2986, (1995).

Andersen, et al., "The structure of cyclin H: common mode of kinase activation and specific features", The EMBO Journal, vol. 16, No. 5, pp. 958-967, (1997).

Arad, et al., "Transient Expression of Human Interleukin-2 and Interferon-□ Genes Is Regulated by Interaction between Distinct Cell Subsets", Cellular Immunology, vol. 160, 240-247 (1995).

Betley, et al., "Nucleotide Sequence of the Type A Staphylococcal Enterotoxin Gene", Journal of Bacteriology, Jan. vol. 170, No. 1. p. 34-41, (1988).

Bohach, et al., "Staphylococcal and Streptococcal Pyrogenic Toxins Involved in Toxic Shock Syndrome and Related Illnesses", Crit. Rev. Microbiol. vol. 17, p. 251 (1990).

Bohach, et al., "Nucleotide sequence of the staphylococcal enterotoxin C1 gene and relatedness to other pyrogenic toxins", Mol Gen Genet vol. 209:15-20, (1987).

Bohach, et al., "Conservation of the Biologically Active Portions of Staphylococcal Enterotoxins C1 and C2", Infection and Immunity, vol. 57, No. 7, p. 2249-2252, (1989).

Brander, et al., "Peptide immunization in humans: a combined CD8+/CD4+T cell-targeted vaccine restimulates the memory C4 T cell response but fails to induce cytotoxic T lymphocytes (CTL)", Clin Exp Immunol, vol. 105:18-25 (1996).

(Continued)

*Primary Examiner*—Mark Navarro
(74) *Attorney, Agent, or Firm*—Browdy and Neimark, PLC

(57) ABSTRACT

The invention relates to peptides comprising an amino acid sequence homologous to the amino sequence of a fragment of a pyrogenic exotoxin, and functional derivatives of said peptides, capable of eliciting protective immunity against toxic shock induced by a pyrogenic exotoxin or by a mixture of pyrogenic exotoxins. Preferred peptides comprise an amino acid sequence homologous to the amino sequence of a fragment of *Staphylococcal aureus* enterotoxin B (SEB). The invention also relates to broad spectrum pharmaceutical compositions for the treatment, protection against or short term prophylaxis of toxin-mediated activation of T cells, comprising as active ingredient at least one peptide according to the invention or derivative thereof, and to broad spectrum vaccines for conferring long term immunity against toxic shock induced by at least one pyrogenic exotoxin are provided. The vaccines comprising as active ingredient at least one peptide according to the invention, or derivative thereof.

12 Claims, 30 Drawing Sheets

OTHER PUBLICATIONS

Buelow, et al., "Localization of the Immunologic Activity in the Superantigen Staphylococcal Enterotoxin B Using Truncated Recombinant Fusion Proteins", The Journal of Immunology, vol. 148, 1-6, No. 1, pp. 1-6, (1992).

Cardarelli, et al., "The Collagen Receptor α2β1, from MG-63 and HT1080 Cells, Interacts with a Cyclic RGD Peptide", The Journal of Biological Chemistry, vol. 267, No. 32, pp. 23159-23164, (1992).

Choi, et al., "Interaction of Staphylococcus aureus toxin "superantigens" with human T cells", Proc. Natl. Acad. Sci, USA, vol. 86, pp. 8941-8945, (1989).

Choi, et al., "Residues of the variable region of the T-cell-receptor β-chain that interact with S.aureus toxin superantigens", Nature, vol. 346, (1990).

Chomczynski, et al., "Single-Step Method of RNA Isolation by Acid Guanidinium Thiocyanate-Phenol-Chloroform Extraction", Analytical Biochemistry, vol. 162, pp. 156-159 (1987).

Cho, et al., "Crystal Structure of a p53 Tumor Suppressor-DNA Complex: Understanding Tumorigenic Mutations", Science, vol. 265, pp. 346-355 (1994).

Couch, et al., "Cloning and Nucleotide Sequence of the Type E Staphylococcal Enterotoxin Gene", Journal of Bacteriology, vol. 170, No. 7, p. 2954-2960, (1988).

Dyer, et al., "A Synthetic Peptide Mimic of Plasma Apolipoprotein E That Binds the LDL Receptor", The Journal of Biological Chemistry, vol. 266, No. 34, pp. 22803-22806, (1991).

Fleischer, et al., "T Cell Stimulation By Staphylococcal Enterotoxins", J. Exp. Med., vol. 167, 1697-1707, (1988).

Fraser, John D., "High-affinity binding of staphylococcal enterotoxins A and B to HLA-DR", Nature, vol. 338, pp. 221-223, (1989).

Gerez, et al., "Aberrant Regulation of Interleukin-2 but Not of Interferon-( Gene Expression in Down Syndrome (Trisomy 21)", Clinical Immunology and Immunopathology, vol. 58, 251-266 (1991).

Gilon, et al., "Backbone Cyclization: A New Method for Conferring Conformational Constraint on Peptides", Biopolymers, vol. 31, 745-750 (1991).

Herman, et al., "SUPERANTIGENS: Mechanism of T-Cell Stimulation and Role in Immune Responses", Annu. Rev Immunol. vol. 9, pp. 745-72, (1991).

Hoffman, et al., "Predictions of T-Cell Receptor- and Major Histocompatibility Complex-Binding Sites on Staphylococcal Enterotoxin C1", Infection and Immunity, vol. 62, No. 8, p. 3396-3407, (1994).

Hughes, et al., "Ability of Synthetic peptides representing epitopes of outer membrane protein F of Pseudomonas aeruginosa to afford protection against P. aeruginosa infection in a murine acute pneumonia model", Vaccine, vol. 13, No. 18, pp. 1750-1753, (1995).

Hudson, et al., "Staphylococcal Enterotoxin A has Two Cooperative Binding Sites on Major Histocompatibility Complex Class II", J. Exp. Med., vol. 182, pp. 711-720 (1995).

Ikejima, et al., "Induction of Human Interleukin-1 by a Product of Staphylococcus aureus Associated with Toxic Shock Syndrome", J. Clin. Invest., vol. 73, pp. 1312-1320. (1984).

Janeway, Charles A. Jr., "Self Superantigens?", Cell, vol. 63, pp. 659-661, (1990).

Janeway, Jr., et al., "T-Cell Responses to M1s and to Bacterial Proteins that Mimic its Behavior", Immunological Reviews, No. 107,.pp. 61-88, (1989).

Jardetzky, et al., Superantigen SEB, Protein Data Bank, PDB code 1SEB, Deposited Nov. 26, 1995, Released Jun. 20, 1996.

Jardetzky, et al., "Three-Dimensional structure of a human class II histocompatibility molecule complexed with superantigen," Nature, vol. 268, pp. 711-718, (1994).

Jeffrey, et al., "Crystal Structure of the Tetramerization Domain of the p53 Tumor Suppressor at 1.7 Angstroms", Science, vol. 267, pp. 1498-1502,(1995).

Jett, et al., "Identification of Staphylococcal Enterotoxin B Sequences Important for Induction of Lymphocyte Proliferation by Using Synthetic Peptide Fragments of the Toxin", Infection and Immunity, vol. 62, No. 8., p. 3408-3415, (1994).

Kaempfer, et al., "Prediction of Response to Treatment in Superficial Bladder Carcinoma Through Pattern of Interleukin-2 Gene Expression", Journal of Clinical Oncology, vol. 14, No. 6, pp. 1778-1786, (1996).

Kappler, et al., "Mutations Defining Functional Regions of the Superantigen Staphylococcal Enterotoxin B", J. Exp. Med. vol. 175, pp. 387-396 (1992).

Hoffmann, Michelle, "Superantigens" May Shed Light on Immune Puzzle"", Science, vol. 248, pp. 637-784 (1990).

Ketzinel, et al., "Regulation of Human Interleukin-2 and Interferon-Gamma Gene Expression by Suppressor T Lymphocytes", Scand. J. Immunol. vol. 33, 593-605, (1991).

Komisar, et al., "Localization of Binding Sites of Staphylococcal Enterotoxin B (SEB), a Superantigen, for HLA-DR by Inhibition with Synthetic Peptides of SEB", Infection and Immunityp. vol. 62, No. 11, pp. 4775-4780 (1994).

Kuchroo, et al., "A Single TCR Antagonist Peptide Inhibits Experimental Allergic Encephalomyelitis Mediated by a Diverse T Cell Reppertoire", The Journal of Immunology, vol. 153, p. 3326. (1994).

Kussie, et al., "Structure of the MDM2 Oncoprotein Bound to the p53 Tumor Suppressor Transactivation Domain", Science, vol. 274, pp. 948-953, (1996).

Leder, et al., "A Mutational Analysis of the Binding of Staphylococcal Enterotoxins B and C3 to the T Cell Receptor β Chain and Major Histocompatibility Complex Class II," J. Exp. Med. vol. 187, pp. 823-833 (1998).

Li, et al., "Three-Dimensional Structure of the Complex between a T Cell Receptor β Chain and the Superantigen Staphylococcal Enterotoxin B", Immunity, vol. 9, pp. 807-816, (1998).

Lowell, et al., "Immunogenicity and Efficacy against Lethal Aerosol Staphylococcal Enterotoxin B Challenge in Monkeys by Intramuscular and Respiratory Delivery of Proteosome-Toxoid Vaccines", Infection and Immunity, vol. 64, No. 11, p. 4686-4693, (1996).

Lowell, et al., "Intranasal and Intramuscular Proteosome-Staphylococcal Enterotoxin B (SEB) Toxoid Vaccines: Immunogenicity and Efficacy against Lethal SEB Intoxication in Mice", Infection and Immunity, vol. 64, No. 5, p. 1706-1713, (1996).

Mallett, et al., "Intranasal or Intragastric Immunization with Proteosome-Shigella Lipopolysaccharide Vaccines Protects against Lethal Pneumonia in a Murine Model of Shigella Infection", Infection and Immunity, vol. 63, No. 6, p. 2382-2386, (1995).

Marrack, et al., "The Toxicity of Staphylococcal Enterotoxin B In Mice Is Mediated by T Cells", J. Exp. Med. vol. 171, pp. 455-464, (1990).

Marrack, et al., "The Staphylococcal Enterotoxins and Their Relatives", Science, vol. 248, pp. 705-711, (1990).

Mayordomo, et al., "Therapy of Murine Tumors with p53 Wild-type and Mutant Sequence Peptide-based Vaccines", J. Exp. Med., vol. 183, pp. 1357-1365, (1996).

"Medical Management of Biological Casualties, Handbook, U.S. Army Medical Research Institute of Infectious Diseases", Third Edition, Table of Contents, Jul. 1998.

Misfeldt, Michael L., "Microbial "Superantigens"", Infection and Immunity, vol. 58, No. 8, p. 2409-2413, (1990).

Mosmann, et al., "TH1 and TH2 Cells: Different Patterns of Lymphokine Secretion Lead to Different Functional Properties", Ann. Rev. Immunol. vol. 7, pp. 145-173, (1989).

Murray, et al., "Staphylococcal and Streptococcal Superantigens: Their Role in Human Disease", ASM News, vol. 61, No. 5, pp. 229-235, (1995).

Papageorgiou, et al., "Crystal Structure of Microbial Superantigen Staphylococcal Enterotoxin B at 1.5 Å Resolution: Implications for Superantigen Recognition by MHC Class II Molecules and T-cell Receptors", J. Mol. Biol. vol. 277 pp. 61-79, (1998).

Pavletich, et al., "The DNA-binding domain of p53 contains the four conserved regions and the major mutation hot spots", Genes & Development, vol. 7, pp. 2556-2564, (1993).

Pinto, et al., "Suppression of the In Vivo Humoral and Cellular Immune Response by Staphylococcal Enterotoxin B (SEB)", Transplantation, vol. 25, No. 6.pp. 320-323, (1978).

Poindexter, et al., "Suppression of Immunoglobulin-Secreting Cells from Human Peripheral Blood by Toxic-Shock-Syndrome Toxin-1", The Journal of Infectious Diseases, vol. 153, No. 4, pp. 772-779, (1986).

Prasad, et al., "Structure of Toxic Shock Syndrome Toxin 1", Biochemistry, vol. 32, No. 50, pp. 13761-13766, (1993).

Prasad, et al., "Toxic Shock Syndrome Toxin 1", Protein Data Bank, PDB code 1TSS, Deposited Oct. 29, 1993, Released Oct. 15, 1994.

Rietman, et al., "Protected peptide disulfides by oxidative detachment from a support", International Journal of Peptide Protein Research, vol. 44, pp. 199-206, (1994).

Sakita, et al., "In vivo CTL immunity can be elicited by in vitro reconstituted MHC/peptide complex", Journal of Immunological Methods, vol. 192, pp. 105-115, (1996).

Schad, et al., "Crystal structure of the superantigen staphylococcal enterotoxin type A", The EMBO Journal, vol. 14, No. 14, pp. 3292-3301, (1995).

Schad, et al., "Staphylococcal Enterotoxin A", Protein Data Bank, PDB code 1SEA, Deposited May 25, 1995, Released Jul. 11, 1996.

Schlievert, Patrick M., "Role of Superantigens in Human Disease", The Journal of Infectious Diseases, vol. 167, pp. 997-1002 (1993).

Scholl, et al., "Toxic shock syndrome toxin 1 binds to major histocompatibility complex class II molecules", Proc. Natl. Acad. Sci USA, vol. 86, pp. 4210-4214, (1989).

Seelig, et al., "Development of a Receptor Peptide Antagonist to Human (-Interferon and Characterization of Its Ligand-bound Conformation Using Transferred Nuclear Overhauser Effect Spectroscopy", The Journal of Biological Chemistry, vol. 270, No. 16, pp. 9241-9249, (1995).

Smith et al, "The Effect if Staphylococcal Enterotoxins on the Primary In Vitro Immune Response," The eJournal of Immunology, vol. 115, pp. 575-578, (1975).

Spiekermann, et al., "Oral Administration of the Bacterial Staphylococcal Enterotoxin B Induces Activation and Cytokine Production by T Cells in Murine Gut-Associated Lymphoid Tissue", The Journal of Immunology, vol. 161:5825-5831, (1998).

Stiles, et al., "Biological Activity of Toxic Shock Syndrome Toxin 1 and a Site-Directed Mutant, H135A, in a Lipopolysaccharide-Potentiated Mouse Lethality Model", Infection and Immunity, vol. 63, No. 4, p. 1229-1234, (1995).

Swaminathan, et al., "Crystal structure of staphylococcal enterotoxin B, a superantigen", Nature, vol. 359, pp. 801-805, (1992).

Toniolo, C., "Conformationally restricted peptides through short-range cyclizations", Int. J. Peptide Protein Res., vol. 35, pp. 287-300, (1990).

Tseng, et al., "Humoral Immunity to Aerosolized Staphylococcal Enterotoxin B (SEB), a Superantigen, in Monkeys Vaccinated with SEB Toxoid-Containing Microspheres", Infection and Immunity, vol. 63, No. 8, p. 2880-2885, (1995).

Uchiyama, et al., "Activation of Murine T Cells by Toxic Shock Syndrome Toxin-1", The Journal of Immunology, vol. 143, pp. 3175-3182, No. 10, (1989).

Wang, et al., "Localization of an Immunologically Functional Region of the Streptococcal Superantigen Pepsin-Extracted Fragment of Type 5 M Protein", The Journal of Immunology, vol. 151, pp. 1419-1429, (1993).

Watson, et al., "Molecular Biology of the Gene", Fourth Edition, vol. 1, The Benjamin Cummings Publishing Company, Inc. Menlo Park, Ca., 2000, pp. 144-147.

Williams, et al., "Design of Bioactive Peptides Based on Antibody Hypervariable Region Structures", The Journal of Biological Chemistry, vol. 266, No. 8, pp. 5182-5190, (1991).

Williams, et al., "Modulation of T Cell Responses with MHC-Derived Peptides", Immunol Res vol. 11, pp. 11-23, (1992).

Woody, et al., "Staphylococcal enterotoxin B mutants (N23K and F44S): biological effects and vaccine potential in a mouse model", Vaccine, vol. 15, No. 2, pp. 133-139, (1997).

* cited by examiner

BROAD SPECTRUM ANTAGONISTS AND VACCINES DIRECTED AGAINST PYROGENIC EXOTOXINS

CROSS REFERENCE TO RELATED APPLICATIONS

This application is a continuation-in-part of U.S. patent application Ser. No. 09/150,947, filed on Sep. 10, 1998.

INTRODUCTION

The invention relates to peptides structurally related to protein domains in pyrogenic exotoxins that are capable of antagonizing the activation of T cells that is mediated by said exotoxins and of eliciting protective immunity against the toxic shock that is induced by said exotoxins. The invention further relates to pharmaceutical preparations containing said peptides, for the treatment or prophylaxis of toxic shock and to vaccines containing said peptides that are capable of eliciting protective immunity against the toxic shock induced by said exotoxins.

BACKGROUND OF THE INVENTION

A family of pyrogenic exotoxins, also known as superantigenic toxins, is produced by *Staphylococcus aureus* and *Streptococcus pyogenes*. The exotoxins comprised of the *S. aureus* enterotoxins (SEs) cause the majority of human food poisoning cases manifested by vomiting and diarrhea after ingestion [Schlievert, J Infect Dis 167:997 (1993)]. *S. aureus* is found widespread in nature, often in association with humans. Among the 5 major serological types within the family of SEs (labeled SEA to SEE and SEG), SEB is the most prominent [Marrack and Kappler, Science 248:705 (1990)]. SEB has also been recognized as a leading cause of human cases of non-menstrual toxic shock syndrome that can accompany surgical or injurious wound infections, as well as viral infections of the respiratory tract of influenza patients to which children are especially vulnerable [Schlievert (1993) ibid.; Tseng et al., Infect Immun 63:2880 (1995)]. Toxic shock syndrome, in its most severe form, causes shock and death [Murray et al., ASM News 61:229 (1995); Schlievert (1993) ibid.]. More generally, members of the staphylococcal exotoxin family, including SEA to SEE and toxic shock syndrome toxin 1 (TSST-1), have been implicated in toxic shock syndrome, in atopic dermatitis [Schlievert (1993) ibid.] and in Kawasaki's syndrome [Bohach et al., Crit Rev Microbiol 17:251 (1990)].

Because of the potential for causing lethal shock in humans after aerosol exposure and because of the relative ease with which SEB can be produced in large amounts, there is concern that SEB could be used as a biological weapon [Lowell et al., Infect Immun 64:1706 (1996)]. SEB is thought to be a potential biological weapon mainly in view of its lethal potential. However, through its exquisite ability to induce vomiting and diarrhea, SEB is also an incapacitating agent that could severely impair the effectiveness of a fighting force, even temporarily, thereby enhancing vulnerability to conventional military means. Needless to say, the harmful effects of SEB need to be generally attacked, and not only in connection with the military aspect.

SEB is a toxic mitogen that triggers a paradoxical response in the infected organism: a vast stimulation of the immune system on the one hand and, on the other hand, a profound immunosuppression that may allow the multiplication of the infecting bacteria, unimpeded by an immune response [Hoffman, Science 248:685 (1990); Smith and Johnson J Immunol 115:575 (1975); Marrack et al., J Exp Med 171:455 (1990); Pinto et al., Transplantation 25:320 (1978)]. During the cellular immune response, a dynamic interplay is induced, by antigens or mitogens, between activation of Th1 type cytokine gene expression, exemplified by interleukin-2 (IL-2), interferon-γ (IFN-γ and tumor necrosis factor-β (TNF-β), and on the other hand, its cell-mediated suppression by CD8 cells and other cell subsets [Ketzinel et al., Scand J Immunol 33:593 (1991); Arad et al., Cell Immunol 160:240 (1995)], and by the inhibitory cytokines from Th2 cells, IL-4 and IL-10 [Mosmann and Coffman, Annu Rev Immunol 7:145 (1989)].

SEB is a member of the family of pyrogenic exotoxins [Herman et al., Ann Rev Immunol 9:745 (1991)] that comprises bacterial exotoxins and Mls proteins. These antigenic toxins stimulate a 20,000-fold greater proportion of rodent or human T cells than do ordinary antigens. Thus, SEB activates 30–40% of all T cells in some mice to divide and produce cytokines [Marrack and Kappler (1990) ibid.]. Indeed, toxicity of SEB requires T cells; mice that lack T cells or SEB-reactive T cells are not affected by doses of SEB that cause weight loss and death in normal animals [Marrack et al. (1990) ibid.; Marrack and Kappler (1990) ibid.]. Unlike normal antigens, SEB and related toxic mitogens do not require processing and antigen presentation [Janeway et al., Immunol Rev 107:61 (1989)] but activate the T cell by binding at a specific site in the variable portion of the β chain (V-β) of the T-cell receptor [Choi et al., Nature 346:471 (1990)]. The crucial region for T-cell receptor interaction with toxin lies on the outer face of the V-β domain, a region not involved in conventional antigen recognition [Choi et al., Proc Natl Acad Sci U.S.A. 86:8941 (1989)]. Simultaneously, pyrogenic exotoxins bind directly to MHC class II molecules [Scholl et al., Proc Natl Acad Sci U.S.A. 86:4210 (1989)] and thus affect primarily CD4$^+$ T cells, although CD8$^+$ cells are also activated [Fleischer and Schrezenmeier, J Exp Med 167:1697 (1988); Fraser, Nature 339:221 (1989); Misfeldt, Infect Immun 58:2409 (1990)]. The current consensus is that pyrogenic exotoxins activate T cells so effectively because they bypass the ordinary interaction of antigen with class II MHC and T-cell receptor [Janeway, Cell 63:659 (1990)]. An alternative view is that pyrogenic exotoxins act as coligands that facilitate, and thus greatly exaggerate, the effect of minute amounts of ordinary antigens [Janeway (1990) ibid.].

The toxicity of SEB and related exotoxins is thought to be related to the capacity of these molecules to stimulate the rapid and excessive production of cytokines, especially of IL-2, IFN-γ and tumor necrosis factors (TNFs). IL-2, IFN-γ, and TNF-β are secreted from activated T helper type 1 (Th1) cells while TNF-β is secreted by Th1 cells, monocytes and macrophages. High levels of these cytokines, suddenly produced, have been implicated as a central pathogenic factor in toxin-related toxicity [Schad et al., EMBO J 14:3292 (1995)] and are thought to cause a rapid drop in blood pressure leading to toxic shock.

While investigation has produced a plausible explanation for the vast stimulation of T cells by SEs, it is not yet clear why these toxins are also strongly immunosuppressive. They induce a decline in both primary T and B cell responses, including the production of antibodies and the generation of plaque-forming cells [Hoffman (1990) ibid.; Smith and Johnson (1975) ibid.; Marrack et al. (1990) ibid.; Pinto et al. (1978) ibid.; Ikejima et al., J Clin Invest 73:1312 (1984); Poindexter and Schlievert, J Infect Dis 153:772 (1986)].

The sensitivity of humans to staphylococcal toxins exceeds that of mice by a factor of 100. Thus, the toxic shock syndrome toxin 1, TSST-1, another pyrogenic exotoxin from *Staphylococcus aureus*, stimulates human T cells to express the key cytokines, IL-2, IFN-γ and TNF-β at <0.1 pg/ml, while murine cells require approximately 10 pg/ml [Uchiyama et al., J Immunol 143:3173 (1989)]. Mice may have developed relative resistance to toxic mitogens by deleting from their T cell repertoire those cells that display the most highly reactive V-β chains or by eliminating these V-β genes [Marrack and Kappler (1990) ibid.]. Such deletions have not been detected in humans, making them far more vulnerable.

The incapacitating and potentially lethal effects of SEB in humans (and of exotoxins of the same family of superantigens), whether exerted on civilians or military personnel, create a need for prophylaxis against SEB, for treatment of SEB-exposed individuals and for a safe SEB vaccine.

Despite the urgency of this need, methods of protection or treatment have been lacking. Thus, in D-galactosamine-sensitized murine models of SEB intoxication, one based on intramuscular challenge with SEB toxin and the other on intranasal challenge using mucosal SEB exposure, it was possible to protect mice with proteosome-SEB toxoid vaccines in which the SEB toxoid component was prepared by a 30-day formalin treatment of the biologically active, intact SEB protein molecule [Lowell et al. (1996) ibid.]. As detailed below, however, the inventors have now found that antibodies raised against certain peptide domains within the SEB molecule enhance the ability of SEB to stimulate human T cells, rather than protecting them against the toxin. This finding limits the use of SEB toxoids as vaccine, in view of the danger of eliciting certain SEB-sensitizing antibodies that could not only fail to confer protective immunity but would lead to significant exacerbation of the toxic responses in SEB-exposed persons.

Other investigators sought recourse in the use of fragments rather than the complete SEB protein molecule, through the synthesis of a series of overlapping SEB peptides, in the order of 30 amino acids each in length [Jett et al., Infect Immun 62:3408 (1994)]. These peptides were used to generate antisera in rabbits whose ability to inhibit the SEB-induced proliferation of a mixture of human T cells and macrophages was then tested. That effort failed to yield an effective or specific inhibitory response. Thus, peptide pSEB(113–144), containing amino acids 113 to 144 of the SEB protein molecule, as well as peptides covering amino acids 130–160, 151–180, and 171–200 each elicited antisera that inhibited the SEB-induced lymphocyte proliferation weakly, by up to 2.5-fold [Jett et al. (1994) ibid.].

A number of investigators attempted to create peptide vaccines. Thus, Mayordomo et al. [J Exp Med 183:1357 (1996)] used a mutant peptide derived from p53 as vaccine for therapy of murine tumors. Hughes and Gilleland [Vaccine 13:1750 (1995)] used synthetic peptides representing epitopes of outer membrane protein F of *Pseudomonas aeruginosa* to afford protection against *P. aeruginosa* infection in a murine acute pneumonia model. In an attempt to use peptide immunization in humans Brander et al. [Clin Exp Immunol 105:18 (1996)] showed that a combined CD8+/CD4+ T cell-targeted vaccine restimulated the memory CD4+ T cell response but failed to induce cytotoxic T lymphocytes.

Major sources of exotoxins are, as already mentioned, *S. Aureus* and *S. Pyogenes*. The flesh-eating bacteria, *S. Pyogenes*, produce a family of different toxins with closely similar mode of action: excessive activation of T cells. *S. Aureus* produces next to SEB as major component, also SEA, SECs, SEE and TSST-1 (toxic shock syndrome toxin 1) and *S. Pyogenes* produces SPE A as major toxin, as well as other pyrogenic exotoxins. Hence, in staphylococcal food poisonings and, more seriously, in biological warfare or in toxic shock caused by *S. pyogenes*, mixtures of toxins are encountered. The composition of such mixtures cannot be anticipated with certainty. The worst scenarios of biological warfare entail not the use of a single, purified pyrogenic exotoxin, as favored for immunological studies, but rather readily attainable, crude natural mixtures of such toxins, as produced, for example, by culturing *S. Aureus*.

Clearly, this complexity demands the development of broad-spectrum antagonists of pyrogenic exotoxins as well as broad-spectrum vaccines.

There exists, therefore, a long-felt need to design a SEB vaccine that is free of sensitizing potential, yet is capable of protecting test animals or humans against lethal doses of toxin. Even greater value would be a vaccine that can afford protection not only against SEB, but also against a wider spectrum of the SE toxin family, including, for example, SEA, SEC, TSST-1, etc.

Moreover, currently, there is no prophylaxis available against SEB or any other pyrogenic exotoxin, nor treatment of exposed persons. There exists, therefore, also a long-felt need to design agents that antagonize the action of SEB, as well as any other pyrogenic exotoxin. Such antidotes will have great value, both in the medical treatment of acute food poisoning and in saving lives in cases of toxic shock and related pathological conditions.

There exists therefore a need for an antagonist against pyrogenic exotoxins, for use in immediate treatment, or short term prevention and rapid prophylaxis, of acute toxic shock and of the harmful effects of such toxins which may be due to, for example, accidental food poisoning, and for a vaccine for immunization against intoxication by pyrogenic exotoxins, for long term protection thereagainst.

In addition, currently there is no way by which to assess the efficacy of vaccination of humans against pyrogenic toxins, since humans cannot be challenged with the toxin in order to check whether they have been conferred the desired immunity. There exists therefore a need for a clinical test for assessing the efficacy of vaccination of humans against pyrogenic toxins which employs surrogate markers.

The inventors have designed a series of peptide antagonists, in particular a 12-mer peptide and a 14-mer peptide, which block the action of pyrogenic exotoxins on the human immune response in vitro, severely inhibiting toxin-mediated induction of IL-2, IFN-γ and TNF-β mRNA. It is clear that these peptides could be used for treatment of acute toxic shock and of harmful effects which may be due to, for example, accidental food poisoning induced by pyrogenic exotoxins. In addition, antibodies raised against individual peptides protect against many pyrogenic exotoxin-mediated responses, suggesting the potential development as broad-spectrum vaccines.

SUMMARY OF THE INVENTION

In a first aspect, the present invention relates to an isolated and purified peptide having an amino acid sequence homologous to an amino acid sequence of a domain of a pyrogenic exotoxin, which domain forms a central turn in the exotoxin starting within β-strand 7 and connecting the β-strand 7, via short β-strand 8, to α-helix 4, and ending within v-helix 4, based on the domain numbering of SEB, and any functional fragments or derivatives of said peptide, wherein said isolated peptide does not have toxin agonist activity and is capable of antagonizing toxin-mediated activation of T lymphocytes, and/or of eliciting protective immunity against toxic shock induced by a pyrogenic exotoxin or by a mixture of pyrogenic exotoxins and protecting against toxic shock induced by a pyrogenic exotoxin or by a mixture of pyrogenic exotoxins.

In one embodiment of the first aspect, the isolated and purified peptide of the invention may comprise an amino acid sequence selected from the group consisting of SEQ ID NO:1 to SEQ ID NO: 11 and SEQ ID NO: 13 to SEQ ID NO:15. Preferably, the peptide of the invention has the amino acid sequence of any one of SEQ ID NO: 2, SEQ ID NO: 13 and any derivatives thereof.

The isolated and purified peptides of the invention and their derivatives are capable of antagonizing toxin-mediated activation of T cells and of protecting against toxic shock induced by a pyrogenic exotoxin or by a mixture of pyrogenic exotoxins.

The peptides of the invention may comprise an amino acid sequence homologous to the amino sequence of a domain of a pyrogenic exotoxin, e.g. SEB, SEA, SEC, TSST-1, SPEA, SPEC, SED, SEE, SEH, SEC1, SEC2, SEC3, etc. See Table 1.

The pyrogenic exotoxin is particularly a bacterial exotoxin produced by Staphylococcus aureus or Streptococcus pyogenes.

According to the invention, the peptides may be further linked through their N-terminus to a lauryl-cysteine (LC) residue and/or through their C-terminus to a cysteine (C) residue, or to other residue/s suitable for linking said peptide to adjuvant/s for immunization.

Further, the peptides may be in the form of a dimer, a multimer or in a constrained conformation, in which the constrained conformation is obtained by internal bridges, short-range cyclizations, extension or other chemical modification.

The peptides of the invention are capable of inhibiting expression of pyrogenic toxin-induced mRNA encoded by the IL-2, IFN-γ or TNF-β genes.

In addition, the peptides of the invention are capable of eliciting in immunized individuals, in the presence of a suitable immunization adjuvant, the production of antibodies that block T-cell pyrogenic toxin-mediated activation.

In a second aspect the present invention relates to a composition which inhibits pyrogenic exotoxin-mediated activation of T-lymphocytes and protects against toxic shock induced by a pyrogenic exotoxin or by a mixture of pyrogenic exotoxins. The composition of the invention comprises as an active ingredient an isolated and purified peptide, in an amount effective to inhibit exotoxin-induced expression of an RNA encoded by the IL-2, INF-γ and/or TNF-β genes, wherein said peptide has an amino acid sequence homologous to an amino acid sequence of a domain of a pyrogenic exotoxin which domain forms a central turn in the exotoxin starting within β-strand 7 and connecting the β-strand 7, via short β-strand 8, to α-helix 4, and ending within α-helix 4, based on the domain numbering of SEB, which peptide does not have toxin agonist activity. Such composition optionally further comprises pharmaceutically acceptable carrier, diluent, adjuvant and/or excipient.

The invention further provides for an immunogenic composition for eliciting antibodies that block pyrogenic exotoxin mediated activation of T-lymphocytes. Such immunogenic composition comprises as an active ingredient in an amount effective to elicit said antibodies, an isolated and purified peptide as defined by the invention.

Still further, the invention provides for a pharmaceutical composition for the treatment of incapacitation induced by at least one pyrogenic exotoxin comprising an isolated and purified peptide according to the invention.

In addition, a pharmaceutical composition is provided, for the treatment or short term prophylaxis of toxin-mediated activation of T cells, comprising as active ingredient a therapeutically effective amount of at least one peptide according to the invention or a derivative thereof. The peptides of the invention are capable of protecting against toxic shock induced by a pyrogenic exotoxin or by a mixture of pyrogenic exotoxins.

Additionally, the invention provides a vaccine for conferring long term immunity against toxic shock induced by at least one pyrogenic exotoxin, comprising as active ingredient an immunologically effective amount of at least one peptide according to the invention, or derivative thereof.

In a further aspect, the invention relates to a method of inhibiting pyrogenic exotoxin-mediated activation of T-lymphocytes and protecting against toxic shock induced by a pyrogenic exotoxin or by a mixture of pyrogenic exotoxins, in a patient in need of such treatment comprising administering to said patient an inhibitory effective amount of an isolated and purified peptide of the invention or of a composition comprising the same.

In yet another example of said aspect, the invention relates to a method of eliciting protective immunity against a toxic shock induced by a pyrogenic exotoxin in a patient in need of such treatment. This method comprises administering to said patient an isolated and purified peptide of the invention or an immunogenic composition comprising the same.

Still further, the invention provides for a method of preventing and/or treating incapacitation induced by at least one pyrogenic exotoxin comprising administering to a patient in need of such treatment at least one therapeutically effective dose of an isolated and purified peptide of the invention or of a composition comprising the same.

Also provided by the invention is a method for the immediate treatment or short term prevention of acute toxic shock and of the harmful effects which may be due to, for example, accidental food poisoning induced by at least one pyrogenic exotoxin, the method comprising administering to a patient in need of such treatment a therapeutically effective amount of the pharmaceutical composition of the invention or a therapeutically effective amount of at least one peptide of the invention.

Additionally, the invention provides a method for conferring long term immunity to toxic shock induced by a pyrogenic exotoxin or a mixture of pyrogenic exotoxins, comprising administering to a patient an effective immunizing amount of a vaccine of the invention.

In addition, the invention relates to antibodies directed against a peptide according to the invention which are capable of blocking T-cell activation by a pyrogenic exotoxin or a mixture of pyrogenic exotoxins, which may be mono- or polyclonal antibodies.

In yet a further aspect, the invention relates to an antiserum containing antibodies directed against at least one peptide of the invention, which peptide can elicit the production of the antibodies. The antiserum is capable of alleviating toxic shock induced by a pyrogenic exotoxin.

In addition, the invention provides for a method for assessing the efficacy of a vaccine for conferring immunity against one or more pyrogenic toxins comprising determining the ability of serum from an immunized individual to antagonize toxin-mediated activation of T cells. A kit for assessing the efficacy of a vaccine for conferring immunity against one or more pyrogenic toxins comprising determining the ability of serum from an immunized individual to antagonize toxin-mediated activation of T cells by the method of the invention is also provided.

DESCRIPTION OF THE FIGURES

(FIG. 7A) Aliquots of $4\times10^6$ PBMC were induced with 100 ng/ml of SEB alone (open circles), or with SEB in the presence of p12(150–161) monomer (filled circles), dimer (filled squares) or trimer (filled triangles); molar excess of each peptide over SEB was 420-fold. (FIG. 7B) Dose response to dimer in the same experiment. Dimer was used at a concentration as in (FIG. 7A) (large filled squares) or diluted 1:10 (medium filled squares) or 1:100 (small filled squares). At times indicated [T(h)], total RNA was extracted and serial twofold dilutions were subjected to dot blot hybridization analysis with $^{32}$P-labeled IFN-γ antisense RNA probe. Autoradiograms were subjected to micro-densitometry at 630 nm; $A_{630}$ is plotted.

In FIGS. 8A and 8C, p12(150–161) was used. In FIGS. 8B and 8D, Cys-p12 (150–161) was used, which is p12(150–161) carrying a Cys residue at both N- and C-termini. At times indicated [T(h)], total RNA was extracted and serial twofold dilutions were subjected to dot blot hybridization analysis with $^{32}$P-labeled IL-2 (FIGS. 8A and 8B), or IFN-γ (FIGS. 8C and 8D) antisense RNA probe. Autoradiograms were subjected to micro-densitometry at 630 nm; $A_{630}$ is plotted.

FIG. 22 shows the protection of mice from SEB-induced lethal shock by antagonist peptides p12A and p14A. Groups of 10 BALB/c mice were challenged with SEB (Sigma) by intraperitoneal injection of 5 μg of the toxin together with 20 mg D-galactosamine. Where indicated, an amount of 25 μg of either p12A or p14A was injected intraperitoneally at 30 minutes before SEB. Survival was monitored.

5. activity of a vaccine, such as anti-SEB vaccine, assayed by the ability of a peptide to protect immunized animals, in the D-galactosamine mouse model, against lethal doses of SEB whether administered via the intramuscular or intranasal route.

The inventors have obtained peptides that meet each of these five criteria. In a specific embodiment of the invention, 12- and 14-mer peptide antagonists were designed. These peptides block the action of SEB as well as other pyrogenic exotoxins on the human immune response in vitro, severely inhibiting toxin-mediated induction of IL-2, IFN-γ and TNF-β mRNA. It is clear that these peptides could be used for treatment of acute toxic shock and of harmful effects which may be due to, for example, accidental food poisoning induced by pyrogenic exotoxins.

In a first aspect, the present invention relates to an isolated and purified peptides having an amino acid sequence homologous to an amino acid sequence of a domain of a pyrogenic exotoxin, which domain forms a central turn in the exotoxin starting within β-strand 7 and connecting the β-strand 7, via short β-strand 8, to α-helix 4, and ending within α-helix 4, based on the domain numbering of SEB, and any functional fragments or derivatives of said peptide, wherein said isolated peptide does not have toxin agonist activity and is capable of antagonizing toxin-mediated activation of T lymphocytes, and/or of eliciting protective immunity against toxic shock induced by a pyrogenic exotoxin or by a mixture of pyrogenic exotoxins and protecting against toxic shock induced by a pyrogenic exotoxin or by a mixture of pyrogenic exotoxins. The homology between any peptide of the present invention and the corresponding region within pyrogenic exotoxin may range between 10% to 100% homology, preferably, 20% to 90% homology, and most preferably, between 28% to 90% homology. The p12 and p14 peptides of the present invention, are both non-limiting examples of peptides possessing significant antagonist activity, although they have less than 30% homology with the corresponding region in other pyrogenic exotoxins such as TSST-1. As exemplified in Table 1, p12 shares 4 out of 12 amino acid residues with TSST-1 (~33%), and p14 shares 4 out of 14 amino acid residues with TSST-1 (~28.5%).

Figure 30:
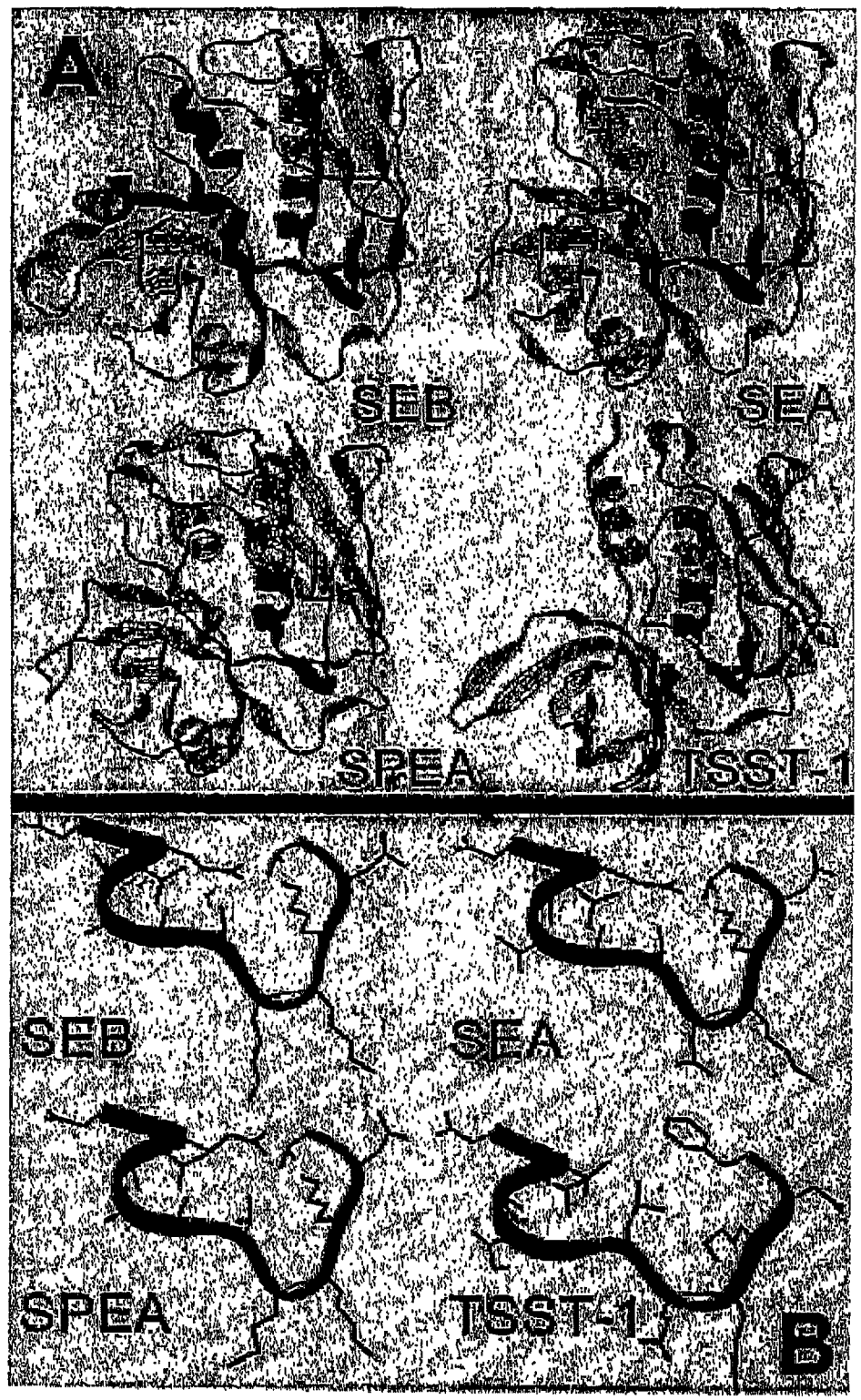

As stated above, the peptides of the present invention comprise an amino acid sequence which is homologous to an amino acid sequence of a three dimensional structural domain of a pyrogenic exotoxin. The structure of this domain is shown in FIG. 30 and is well conserved even among pyrogenic exotoxins which share relatively low homology (e.g. compare the three dimensional structure of SEB and TSST-1 in FIG. 30 and note that the amino acid sequence for these regions shares only ~33% homology.)

The present invention demonstrates that this three-dimensional structural domain of pyrogenic exotoxins may provide a basis for identifying peptides with a common functional activity. In fact, it is well known in the art that three-dimensional structural domains often relate to a particular activity of a protein. This is discussed in detail, e.g. in Molecular Biology of the Gene, Watson, Hopkins, Roberts, Steitz and Weiner, Fourth Edition, The Benjamin/Cummings Publishing Company, Inc. (1987) (pp. 144–146; 162, attached hereto as Exhibit 1), where a domain is described as: "a compact, folded part of the structure, that appears separate from the rest, as if it would be stable in solution on its own (which is often demonstrated to be the case)". The structure-function relatedness is a most important factor.

To give a specific example, DNA binding and tetramerization domains of p53 were defined by proteolytic digestion of p53 [Pavletich et al., *Genes Dev.* 7:2556–2464 (1993)]. Furthermore, Pavletich confirmed that these were structural domains by determining the three-dimensional structure of the domains. The x-ray crystallographic three-dimensional structure of the DNA binding domain elucidated how the domain bound to DNA [Cho et al., *Science* 265:346–355 (1994)]. In addition, the three-dimensional structure of the tetramerization domain showed that in fact, this domain is in the form of a tetramer (tetramerization is known to be required for activity) [Jeffrey et al., *Science* 267:1498–1502 (1995)].

It is also well understood that structural and functional conservation of protein families is not always directly related to sequence conservation. For example, cyclin A and H are not highly conserved in amino acid sequence homology, in fact they are quite divergent. However, they are structurally and functionally conserved. For example, in vitro they can bind to an activate each other's cyclin dependent kinase partner [Anderson et al. EMBO J. 16:958–67 (1998)]. While the sequence of cyclin A and cyclin H is not highly conserved, their respective three-dimensional structures, as well as the structures of several other cyclins, indicates that there are key amino acid sequences which are important for secondary and tertiary structural interactions and also for interactions with other molecules (such as cyclin-dependent kinases) that are highly conserved. It is also well known that small peptides can have secondary structure. For example, the structure of MDM2 oncoprotein bound to a 15-amino acid transactivation domain peptide of p53 shows that the p53 peptide binds as an α-helix [Kussie et al., *Science* 8:948–953 (1996)]. Similarly, while the peptides of the present invention may share little sequence homology (see Table 1 below), there is striking conservation of the corresponding structural domains comprising these peptides (see FIG. 30, Example 18). Furthermore, the peptides themselves, when not part of the full length protein may have secondary structure.

In one embodiment of the present aspect, the isolated and purified peptide of the invention may comprise the amino acid sequence selected from the group consisting of any one of SEQ ID NO:1 to SEQ ID NO: 1 and SEQ ID NO: 13 to SEQ ID NO:15. Preferably, the peptide of the invention has the amino acid sequence selected from the group consisting of any one of SEQ ID NO:1 to SEQ ID NO: 11 and SEQ ID NO: 13 to SEQ ID NO:15.

In yet another preferred embodiment, the peptide of the present invention comprises the amino acid sequence of SEQ ID NO:2, and preferably, has the amino acid sequence of SEQ ID NO:2.

Alternatively, the peptide of the present invention may comprise the amino acid amino acid sequence of SEQ ID NO:13. Preferably, the isolated and purified peptide of the invention has the amino acid sequence of SEQ ID NO:13.

The present invention further provides for an isolated and purified peptide comprising the amino acid sequence selected from the group consisting of any one of SEQ ID NO:1 to SEQ ID NO:11 and SEQ ID NO:13 to SEQ ID NO:15. More preferably, the peptide of the invention may have any of the amino acid sequence selected from the group consisting of any one of SEQ ID NO:1 to SEQ ID NO:11 and SEQ ID NO:13 to SEQ ID NO:15.

In a particular example, the peptide may comprise the amino acid sequence according to SEQ ID NO:2. Preferably, such peptide has the amino acid sequence according to SEQ ID NO:2.

In yet another particular example, the invention relates to an isolated and purified peptide comprising the amino acid sequence according to SEQ ID NO:13. More preferably, the isolated and purified peptide may have the amino acid sequence according to SEQ ID NO:13.

Still further, the invention relates to an isolated and purified peptide comprising any one of the following consensus sequences:

(1) $Xaa_{(n)}KXaa_{(8)}D$ (SEQ ID NO:54);
(2) $Xaa_{(n)}KXaa_{(3)}TXaaQEXaaD$ (SEQ ID NO:55);
(3) $Xaa_{(n)}KKXaa_{(6)}LD$ (SEQ ID NO:56); and
(4) $Ch.aa-Xaa_{(2)}-Hb.aa-X-Hb.aa-Po.aa-Po.aa-Hb.aa-D$ (SEQ ID NO:57), wherein Xaa is an amino acid, n is zero or an integer of from 1 to 10, Ch.aa is a charged amino acid, Hb.aa is a hydrophobic amino acid and Po.aa is a polar amino acid and wherein said peptide does not have toxin agonist activity.

In a preferred embodiment, such peptide having any of the above mentioned consensus sequences, comprises the amino acid sequence selected from the group consisting of any one of SEQ ID NO:1 to SEQ ID NO:4 and SEQ ID NO:13 and any derivatives thereof. More preferably, such peptide according to this embodiment has the amino acid sequence selected from the group consisting of any one of SEQ ID NO:1 to SEQ ID NO:4 and SEQ ID NO:13 and any derivatives thereof. Non-limiting examples of derivatives for these peptides, may comprise or preferably have, the amino acid sequences according to SEQ ID NO:5 to SEQ ID NO:11, SEQ ID NO:14 and SEQ ID NO:15.

In a particular embodiment, wherein n is zero, the peptide has the amino acid sequence according to SEQ ID NO: 4 (also referred to as p10) or any derivative thereof. For example, the peptide of SEQ ID NO:5 is a derivative of p10.

In a most preferred embodiment, wherein n is 2, said peptide has the amino acid sequence of SEQ ID NO:2, or any derivatives thereof, such as the derivatives exemplified by any of the SEQ ID NO:6 to SEQ ID NO:11.

In yet another most preferred embodiment, wherein n is 4, the peptide of the invention may have the amino acid sequence of SEQ ID NO:13 or of any derivatives thereof, such as peptides having the amino acid sequences of any one of SEQ ID NO:14 or SEQ ID NO:15.

As mentioned above, support for the consensus amino acid sequences are found in the peptides of the present invention (p10, p12 and p14 having the amino acid sequences of SEQ ID NO:2, SEQ ID NO:4 and SEQ ID NO:13, respectively). The specification clearly provides that the peptides have KK and QELD motifs that are common to SEB, as well as to the related toxins SEA, SEC1, SEC2 and S. pyogenes exotoxin A (SPE A) as indicated on Table 1. Table 1 is an alignment of the SEB domains from known pyrogenic exotoxins and provides a basis for the consensus sequences described above.

In another embodiment, peptide antagonists of the present invention can elicit antibodies that protect human lymphoid cells against SEB, SEA, and TSST-1, indicating that they may confer wider protective immunity against pyrogenic toxins. However, antibodies raised against peptides derived from certain other SEB protein domains actually enhanced the response of human PBMC to SEB and SEA, as expressed by greater induction of IL-2 and IFN-γ mRNA, rather than protect against the toxins. Immunization of mice with these SEB antagonist peptides elicited protection against lethal doses of SEB, resulting in survival of test animals. It is clear that these peptides may also be used for conferring long-term immunity against toxic shock induced by pyrogenic exotoxins.

TABLE 1

Alignment of SEB domain among pyrogenic toxins

| PEPTIDE | SEQUENCE | SEQ ID NO: |
|---------|----------|------------|
| p12 | YNKKKATVQELD | 2 |
| p14 | VQYNKKKATVQELD | 13 |
| SPEA | IETNKKMVTAQELD | 26 |
| SPEA1* | IETNKKMVTAQELD | 27 |
| SPEC | IILEKDIVTFQEID | 28 |
| SPEG | VRIKKKQFTLQEFD | 29 |
| SPEH | ITVNKPKVTAQEVD | 30 |
| SPET | VSTDKKEVTTQELD | 31 |
| SPEJ | IKIDKPIFTIQEFD | 32 |
| smeZ | ISTNKTTVTAQEID | 33 |
| SPEGG | ILIKHKQFTLQEFD | 34 |
| SEA | VKTNKKNVTVQELD | 35 |
| SEB | VQTNKKKVTAQELD | 36 |
| SEC1 | VQTDKKSVTAQELD | 37 |
| SEC2 | VQTDKKSVTAQELD | 37 |
| SEC3 | VQTDKKSVTAQELD | 37 |
| SED | VQTDKKNVTVQELD | 38 |
| SEE | VKTSKKEVTVQELD | 39 |
| SEG | ITTNKNMVTIQELD | 40 |
| SEH | IRTNKKNVTLQELD | 41 |
| SEI | IATNKKLVTAQEID | 42 |
| SEJ | VKTNKKKVTIQELD | 43 |
| SEL | TDTDKKMVTAQEID | 44 |
| SEM | VSTNKKLVTAQEID | 45 |
| SEN | IKTKKAKVTVQELD | 46 |
| SEO | VTTDKKKVTAQELD | 47 |
| SEP | VKTNKKEVTVQELD | 48 |
| TSST-1 | PKFDKKQLAISTLD | 49 |

Thus, according to the present aspect, the invention relates to peptides comprising an amino acid sequence homologous to the amino sequence of a domain of a pyrogenic exotoxin, and to functional derivatives of such peptides, wherein said isolated and purified peptide does not have toxin agonist activity and is capable of eliciting protective immunity against toxic shock induced by the exotoxins and/or capable of antagonizing toxin-mediated activation of T cells. Still further, the peptides of the invention are capable of protecting against toxic shock induced by a pyrogenic exotoxin or by a mixture of pyrogenic exotoxins.

The terms derivatives and functional derivatives as used herein mean peptides with any insertions, deletions, substitutions and modifications to the peptide that do not interfere with the peptides ability to elicit protective immunity against toxic shock induced by the exotoxins and/or of antagonizing toxin-mediated activation of T cells (hereafter referred to as "derivative/s"). A derivative should maintain a minimal homology to said domain, e.g. even less than 30%. Examples for such derivatives may be found in any one of SEQ ID NO:5 to SEQ ID NO:11, SEQ ID NO:14 and SEQ ID NO:15.

The pyrogenic exotoxin is usually a bacterial exotoxin, specifically an exotoxin produced by *Staphylococcus aureus* or by *Streptococcus pyogenes*.

In a preferred embodiment of said aspect of the invention, the invention relates to a peptide comprising an amino acid sequence homologous to the amino sequence of a domain of *Staphylococcal aureus* enterotoxin B (SEB).

In a specifically preferred embodiment, the invention relates to isolated and purified peptides comprising the amino acid sequence shown in SEQ ID NO:1 (positions 150 to 161 of the sequence of the naturally occurring SEB protein shown in SEQ ID NO:12), and functional derivatives thereof, capable of eliciting protective immunity against toxic shock induced by at least one pyrogenic exotoxin and/or of antagonizing toxin-mediated activation of T cells. These peptides are also capable of protecting against toxic shock induced by a pyrogenic exotoxin or by a mixture of pyrogenic exotoxins. These peptides can therefore be used for both immediate treatment of acute toxic shock and of the harmful effects which may be due to, for example, accidental food poisoning, induced by the pyrogenic exotoxins and for conferring long-term immunity against such toxic shock.

A particular example may be a peptide having the amino acid sequence shown in SEQ ID NO:1 (hereafter also referred to as pSEB (150–161)) and functional derivatives thereof. In a preferred embodiment, the derivative maintains at least 30% homology to SEQ ID NO:1. This peptide is capable of eliciting protective immunity against toxic shock induced by at least one pyrogenic exotoxin and/or of antagonizing toxin-mediated activation of T cells.

In another particularly preferred embodiment, the invention relates to isolated and purified peptides comprising the amino acid sequence shown in SEQ ID NO:2 and to derivatives thereof, capable of eliciting protective immunity against toxic shock induced by at least one pyrogenic exotoxin and/or of antagonizing toxin-mediated activation of T cells. Also these peptides can be used for both immediate treatment of acute toxic shock and of the harmful effects which may be due to, for example, accidental food poisoning induced by the pyrogenic exotoxins and for conferring long-term immunity against such toxic shock. A particular example may be a peptide having the amino acid sequence shown in SEQ ID NO:2 (hereinafter also referred to as p12(150–161)) and derivatives thereof capable of eliciting protective immunity against toxic shock induced by at least one pyrogenic exotoxin and/or of antagonizing toxin-mediated activation of T cells.

In a further embodiment, the invention relates to isolated and purified peptides comprising the amino acid sequence shown in SEQ ID NO:3 (positions 152 to 161 of the sequence of the naturally occurring protein shown in SEQ ID NO:12) and to functional derivatives thereof, capable of eliciting protective immunity against toxic shock induced by at least one pyrogenic exotoxin and/or of antagonizing toxin-mediated activation of T cells. Also these peptides can be used for both immediate treatment of acute toxic shock and of the harmful effects which may be due to, for example, accidental food poisoning induced by the pyrogenic exotoxins and for conferring long-term immunity against such toxic shock.

Particular example for functional fragment of SEQ ID NO:1 may be a peptide having the amino acid sequence shown in SEQ ID NO:3 (hereinafter also referred to as pSEB(152–161)) and derivatives thereof. Such peptide is capable of eliciting protective immunity against toxic shock induced by a pyrogenic exotoxin or a mixture of pyrogenic exotoxins and/or of antagonizing toxin-mediated activation of T cells.

Still further, the invention relates to isolated and purified peptides comprising the amino acid sequence shown in SEQ ID NO:4 and to functional derivatives thereof, capable of eliciting protective immunity against toxic shock induced by at least one pyrogenic exotoxin and/or of antagonizing toxin-mediated activation of T cells. Also these peptides can be used for both immediate treatment of acute toxic shock and of the harmful effects which may be due to, for example, accidental food poisoning induced by the pyrogenic exotoxins and for conferring long-term immunity against such toxic shock.

A particular example may be a peptide having the amino acid sequence shown in SEQ ID NO:4 (hereinafter also referred to as p10(152–161)) and functional derivatives thereof, capable of eliciting protective immunity against toxic shock induced by a pyrogenic exotoxin or a mixture of pyrogenic exotoxins and/or of antagonizing toxin-mediated activation of T cells.

The peptide of the invention may contain amino acid insertions or deletions within the peptide or at its N- or C-terminus as demonstrated by p14 (SEQ ID NO:13). p14 contains two additional amino acids residues (valine and glutamine) at the N-terminus of pSEB(150–161) preceding the sequence of YNKKKATVQELD of p12 (SEQ ID NO: 2), and is homologous to positions 148 to 161 of the sequence of the naturally occurring protein shown in SEQ ID NO:12 in 11 out of its 14 amino acid residues. It is to be appreciated that any suitable amino acid residues may be added in a similar manner in order to obtain a potent antagonist.

Thus, in a particularly preferred embodiment, the invention relates to isolated and purified peptides comprising the amino acid sequence shown in SEQ ID NO:13 (hereinafter also referred to as p14(148–161) and to functional derivatives thereof. As mentioned above, SEQ ID NO:13 corresponds to positions 148 to 161 of the sequence of the naturally occurring protein shown in SEQ ID NO:12. The p14 peptide of the invention is capable of eliciting protective immunity against toxic shock induced by a pyrogenic exotoxin or a mixture of pyrogenic exotoxins and/or of antagonizing toxin-mediated activation of T cells. Also these peptides can be used for both immediate treatment of acute toxic shock and of the harmful effects which may be due to, for example, accidental food poisoning induced by the pyrogenic exotoxins and for conferring long-term immunity against such toxic shock.

As mentioned, pSEB(150–161) corresponds to the natural amino acid sequence in SEB between positions 150–161, while p12(150–161) differs from the corresponding natural amino acid sequence of SEB in 3 out of the 12 positions, yet possesses even greater toxin antagonist activity. It is thus possible to design a pyrogenic exotoxin antagonist and/or vaccine through use of short peptides homologous, but not necessarily identical to, domains within the SEB toxin molecule. Furthermore, the p12(150–161) peptide also possesses toxin antagonist activity against TSST-1 but is only approximately 30% homologous to the corresponding region in TSST-1. Moreover, as further shown by FIG. 23, the p14 peptide, which shares less than 30% homology to the corresponding region in TSST-1 (sharing 4 out of 14 amino acid residues), exhibits even more potent antagonistic activity compares to p12.

The lack of structure of linear peptides renders them vulnerable to proteases in human serum and acts to reduce their affinity for target sites, because only few of the possible conformations may be active. Therefore, it is desirable to optimize antagonist peptide structure, for example by creating different derivatives of the various peptides of the invention.

In order to improve peptide structure, the peptides of the invention can be coupled through their N-terminus to a lauryl-cysteine (LC) residue and/or through their C-terminus to a cysteine (C) residue, or to other residue/s suitable for linking the peptide to adjuvant/s for immunization, as will be described in more detail hereafter.

Accordingly, in a further embodiment, the invention relates to a peptide having the amino acid sequence shown in SEQ ID NO:5 (hereinafter also referred to as pSEBLC (150–161) and functional derivatives thereof, capable of eliciting protective immunity against toxic shock induced by pyrogenic exotoxins and/or of antagonizing toxin-mediated activation of T cells. These peptides can also be used for both immediate treatment of acute toxic shock and of the harmful effects which may be due to, for example, accidental food poisoning induced by the pyrogenic exotoxins and for conferring long-term immunity against such toxic shock.

In yet another embodiment, the invention relates to a peptide having the following amino acid sequence shown in SEQ ID NO:6 (hereinafter also referred to as p12LC (150–161)) and functional derivatives thereof capable of eliciting protective immunity against toxic shock induced by pyrogenic exotoxins and/or of antagonizing toxin-mediated activation of T cells.

Evidently, such peptides can also be used for both immediate treatment of acute toxic shock and of the harmful effects which may be due to, for example, accidental food poisoning induced by the pyrogenic exotoxins and for conferring long-term immunity against such toxic shock.

The peptides of the invention, as well as derivatives thereof may all be positively charged, negatively charged or neutral and may be in the form of a dimer, a multimer or in a constrained conformation.

A constrained conformation can be attained by internal bridges, short-range cyclizations, extension or other chemical modification.

Peptides in the form of a dimer or trimer can have, for example, the amino acid sequences shown in SEQ ID NOS. 7 and 8, respectively (hereinafter also referred to as Dimer and Trimer, receptively) and functional derivatives thereof, capable of eliciting protective immunity against toxic shock induced by pyrogenic exotoxins and/or of antagonizing toxin-mediated activation of T cells. As with other peptides of the invention, these peptides can also be used for both immediate treatment of acute toxic shock and of the harmful effects caused thereby and for conferring long-term immunity against such toxic shock.

Further, the peptides of the invention may be extended at the N-terminus and/or C-terminus thereof with various identical or different amino acid residues. As an example for such extension, the peptide may be extended at the N-terminus and/or C-terminus thereof with identical or different hydrophobic amino acid residue/s which may be naturally occurring or synthetic amino acid residue/s. A preferred synthetic amino acid residue is D-alanine.

Particular examples for peptides extended with synthetic amino acid residues are the peptides having the amino acid sequence shown in SEQ ID NO:10 (hereinafter also referred to as D-Ala or p12A) or SEQ ID NO:14 (hereinafter also referred to as p14A) and functional derivatives thereof, capable of eliciting protective immunity against toxic shock induced by pyrogenic exotoxins and/or of antagonizing toxin-mediated activation of T cells. In a specifically preferred embodiment, p12A and p14A carrying a D-Ala residues at both their N-terminus and C-terminus, and therefore the most preferred peptides of the present invention may be any one of p12A and p14A.

An additional example for such an extension is provided by peptides extended both at the N-terminus and/or C-terminus thereof with a cysteine residue. Naturally, such an extension may lead to a constrained conformation due to Cys—Cys cyclization resulting from the formation of a disulfide bond. A particular such peptide has the amino acid sequence shown in SEQ ID NO:9 (hereinafter also referred to as Cys-p12(150–162)) and functional derivatives thereof, capable of eliciting protective immunity against toxic shock induced by pyrogenic exotoxins and/or of antagonizing toxin-mediated activation of T cells. According to one embodiment of the invention, the Cys-p12(150–162)) is a cyclic peptide having a disulfide bond via the terminal cysteine residues. Nevertheless, the Cys-p12(150–162) peptide may be linear.

Another example is the incorporation of an N-terminal lysyl-palmitoyl tail, the lysine serving as linker and the palmitic acid as a hydrophobic anchor, to generate the derivative p14A-LP (SEQ ID NO:15).

In addition the peptides may be extended by aromatic amino acid residue/s, which may be naturally occurring or synthetic amino acid residue/s. A preferred aromatic amino acid residue is tryptophan. Alternatively, the peptides can be extended at the N-terminus and/or C-terminus thereof with amino acids present in corresponding positions of the amino acid sequence of the naturally occurring pyrogenic exotoxin.

Nonetheless, according to the invention, the peptides of the invention may be extended at the N-terminus and/or C-terminus thereof with various identical or different organic moieties which are not a naturally occurring or synthetic amino acids. As an example for such extension, the peptide may be extended at the N-terminus and/or C-terminus thereof with an N-acetyl group. A particular example for such an extension is the peptide having the amino acid sequence shown in SEQ ID NO:11 (hereinafter also referred to as Ac-p12(150–161)) and functional derivatives thereof, capable of eliciting protective immunity against toxic shock induced by pyrogenic exotoxins and/or of antagonizing toxin-mediated activation of T cells.

These extended peptides, as other peptides of the invention, can also be used for both immediate treatment of acute toxic shock and of the harmful effects caused thereby and for conferring long-term immunity against such toxic shock.

The peptides of the invention are capable of inhibiting expression of pyrogenic toxin-induced mRNA encoded by the IL-2, IFN-γ or TNF-β genes, as will be shown in the following Examples.

In addition, the peptides of the invention are capable of eliciting the production of antibodies that block T-cell activation in immunized individuals. The production of antibodies will be enhanced in the presence of a suitable immunization adjuvant. Preferred adjuvants may be keyhole limpet hemocyanin (KLH), proteosomes or alum.

As will be shown in the Examples, peptide p12(150–161), peptide p14 (148–161) and the specific derivatives thereof, i.e. the Dimer form, the Cys form (Cys-p12(150–161)) and/or D-Ala form exhibit antagonist activity against SEB as well as against other pyrogenic exotoxins. The amino acid sequence of these synthetic peptides having the sequence shown in SEQ ID NOS:2, 7, 9, 10, 13 and 14, differ in several positions from the corresponding sequence in SEB, T N KK K V T A QELD (SEQ ID NO:1), found in peptide pSEB(150–161) and V Q T N KK K V T A QELD (SEQ ID NO:50), found in peptide pSEB(148–161) The K K K and Q E L D motifs, features shared by peptides p12(150–161), pSEB(150–161), p10 (152–161), p14 (148–161), and their derivatives, are spaced equally in both and may be important for antagonist activity, with the triple-lysine motif K K K conferring 3 positive charges. Residues T150, K152, E159 and D161 of this SEB domain are conserved among all staphylococcal enterotoxins [Swaminathan et al. (1992) ibid.].

The 150–161 domain of SEB is highly conserved among certain pyrogenic toxins in general, with 10/12 identities for SEA, SEC1, SEC2, and *S. pyogenes* exotoxin A (SPE A) and 9/12 for SEE [Bohach and Schlievert, Mol Gen Genet 209:5 (1987); Couch et al., J Bacteriol 170:2954 (1988); Bohach and Schlievert, Infect Immun 57:2249 (1989)]. All of these toxins contain the residues underlined above, including the first 2 lysine residues (K K) and the Q E L D [Swaminathan et al. (1992) ibid.; Bohach and Schlievert (1987) ibid.; Couch et al. (1988) ibid.; Bohach and Schlievert (1989) ibid.]. Table 1 shows an alignment of these sequences. The superantigen, pep M5 protein, also contains a region with limited homology (<50%) to pSEB(150–161) located near its C-terminus [Wang et al., J Immunol 151:1419 (1993)].

Conservation of SEB domains among the pyrogenic toxin family is, however, not unique for amino acids 150–161. SEB domains covering amino acids 76–86, 113–124, 151–168 and 213–226 all show extensive conservation within this family [Hoffmann et al., Infect Immun 62:3396 (1994)]. Moreover, the relevance of the conservation of the above-mentioned motifs corresponding to part of the sequence in pSEB(150–161) is not clear, since this region does not contribute to mitogenicity [Wang et al. (1993) ibid.].

In a second aspect, the invention relates to pharmaceutical compositions for the treatment or prophylaxis of toxin-mediated activation of T cells, comprising as active ingredient a therapeutically effective amount of at least one peptide according to the invention or derivative thereof. As described above, the peptides comprise an amino acid sequence substantially homologous to the amino acid sequence of a fragment SEB. By substantially homologous, is meant, between 10% to 100% homology, preferably, between 20% to 90% homology, and most preferably, between 28% to 90% homology. However, the homology may be according to a preferred embodiment, as low as about 28.5% (4 out of 14 amino acid residues, as the homology between p14 and TSST-1). The pharmaceutical compositions of the invention are also useful in protecting against toxic shock induced by a pyrogenic exotoxin or by a mixture of pyrogenic exotoxins.

The term toxin-mediated activation as used throughout this application can mean activation of T cells mediated by a single pyrogenic exotoxin or a mixture of such toxins.

Examples 4, 5, 6 and most remarkably the in vivo murine experiments described in Example 9 to 12 and the experiments performed in pigs in Example 17, show that it is possible to design an effective pyrogenic exotoxin antagonist pharmaceutical composition, which contains as active ingredient a peptide according to the invention, and acts as a broad-spectrum antagonist of pyrogenic exotoxins. Thus, for example, the p12(150–161) or the p14(148–161) peptides carrying D-Ala residues at both its N- and C-termini, which is SEB-related, afforded good antagonist activity not only against SEB-induced toxic shock, but also against toxic shock induced by the remotely homologous TSST-1.

Examples 10–16 show that the short peptide composed of 14 amino acids (p14 or p14A, corresponding to positions 148–161 of the sequence of the naturally occurring SEB protein shown in SEQ ID NO:12) demonstrates highly effective antagonist activity against SEB-induced and TSST-1, induced toxic shock in mice, even though there is relatively low sequence homology to the corresponding TSST-1 (less than 30%). Furthermore, p14A was capable of eliciting protective immunity against toxic shock when administered as late as 7 hours after SEB challenge. In addition, p14A allowed the challenged mice to quickly develop broad spectrum resistance.

Thus, the present invention relates to a composition which inhibits pyrogenic exotoxin-mediated activation of T-lymphocytes and protects against toxic shock induced by a pyrogenic exotoxin or by a mixture of pyrogenic exotoxins. The composition of the invention comprises as an active ingredient an isolated and purified peptide, in an amount effective to inhibit exotoxin-induced expression of an RNA encoded by the IL-2, INF-γ and/or TNF-β genes, wherein said peptide has an amino acid sequence homologous to an amino acid sequence of a domain of a pyrogenic exotoxin which domain forms a central turn in the exotoxin starting within β-strand 7 and connecting the β-strand 7, via short β-strand 8, to α-helix 4, and ending within α-helix 4, based on the domain numbering of SEB, which peptide does not have toxin agonist activity. Such composition optionally further comprises pharmaceutically acceptable carrier, diluent, adjuvant and/or excipient.

In a preferred embodiment, which composition comprises as an active ingredient an isolated and purified peptide having an amino acid sequence selected from the group consisting of any one of SEQ ID NO:1 to SEQ ID NO:11 and SEQ ID NO:13 to SEQ ID NO:15 and any combination or mixture thereof and optionally further comprises pharmaceutically acceptable carrier, diluent, adjuvant and/or excipient.

In one specifically preferred embodiment, the composition of the invention comprises as an active ingredient, a peptide which has the amino acid sequence of SEQ ID NO:2, or of any derivatives thereof. Such derivatives may be for example any of the peptides having the amino acid sequences according to any one of SEQ ID NO:6 to SEQ ID NO:11.

In yet another specifically preferred embodiment, the composition of the invention may comprises as an active ingredient, a peptide which has the amino acid sequence of SEQ ID NO:13, or of any derivatives thereof. Such derivatives may be for example any of the peptides having the amino acid sequences according to any one of SEQ ID NO:14 and SEQ ID NO:15.

Generally, the composition of the invention may comprise as an active ingredient, any of the isolated and purified peptides as defined by the invention and optionally further comprises pharmaceutically acceptable carrier, diluent, adjuvant and/or excipient.

The invention further provides for an immunogenic composition for eliciting antibodies that block pyrogenic exotoxin mediated activation of T-lymphocytes. Such immunogenic composition comprises as an active ingredient in an amount effective to elicit said antibodies, an isolated and purified peptide having an amino acid sequence homologous to an amino acid sequence of a domain of a pyrogenic exotoxin, which domain forms a central turn in the exotoxin starting within β-strand 7 and connecting the β-strand 7, via short β-strand 8, to α-helix 4, and ending within α-helix 4, based on the domain numbering of SEB, wherein said peptide does not have toxin agonist activity, which composition optionally further comprises pharmaceutically acceptable carrier, diluent, adjuvant and/or excipient.

The immunogenic composition according to a preferred embodiment, may comprise as an active ingredient an isolated and purified peptide having the amino acid sequence selected from the group consisting of SEQ ID NO:1 to SEQ ID NO:11 and SEQ ID NO:13 to SEQ ID NO:15 and any combination or mixture thereof, and optionally further comprises pharmaceutically acceptable carrier, diluent, adjuvant and/or excipient.

In one specifically preferred embodiment, the immunogenic composition of the invention comprises as an active ingredient, a peptide which has the amino acid sequence of SEQ ID NO:2, or of any derivatives thereof. Such derivatives may be for example any of the peptides having the amino acid sequences according to any one of SEQ ID NO:6 to SEQ ID NO:11.

In yet another specifically preferred embodiment, the immunogenic composition of the invention comprises as an active ingredient, a peptide which has the amino acid sequence of SEQ ID NO:13, or of any derivatives thereof. Such derivatives may be for example any of the peptides having the amino acid sequences according to any one of SEQ ID NO:14 and SEQ ID NO:15.

Generally, the immunogenic composition of the invention may comprise as an active ingredient, any of the isolated and purified peptides as defined by the invention and optionally further comprises pharmaceutically acceptable carrier, diluent, adjuvant and/or excipient.

The pharmaceutically 'effective amount' for purposes herein is that determined by such considerations as are known in the art. The amount must be sufficient to antagonize toxin-mediated activation of T cells.

The pharmaceutical composition of the invention can be prepared in dosage units forms and may be prepared by any of the methods well-known in the art of pharmacy. In addition, the pharmaceutical compositions of the invention may further comprise pharmaceutically acceptable additives such as pharmaceutical acceptable carrier, excipient or stabilizer, and optionally other therapeutic constituents. Naturally, the acceptable carriers, excipients or stabilizers are non-toxic to recipients at the dosages and concentrations employed.

The magnitude of therapeutic dose of the composition of the invention will of course vary with the group of patients (age, sex, etc.), the nature of the condition to be treated and with the route administration and will be determined by the attending physician.

In yet a further embodiment, the invention relates to vaccines for conferring immunity against toxic shock induced by pyrogenic exotoxins, comprising as active ingredient an immunologically effective amount of at least one peptide according to the invention or derivatives thereof and may contain mixtures of such peptides and derivatives.

By the term 'immunologically effective amount' is meant any amount sufficient to enhance the production of antibodies that block T cell activation induced by pyrogenic exotoxins, and confer immunity against toxic shock induced by a pyrogenic exotoxin or by a mixture of pyrogenic exotoxins.

The vaccines of the invention may optionally further comprise suitable immunization adjuvants or mixtures thereof. Suitable adjuvants may be proteosomes, KLH and alum, as well as combinations of proteosomes with alum and of KLH with alum.

As will be shown in the following Examples, the vaccines according to the invention are capable of enhancing production of antibodies that block T-cell activation induced by pyrogenic exotoxins.

Efforts to develop antidotes for use against toxic shock symptoms have concentrated on blocking downstream phenomena in the toxicity cascade, mainly by inhibiting the action of TNF with monoclonal antibodies or soluble receptors. The high levels of cytokines produced in response to toxins render this approach ineffective. The present invention shows that it is possible to block the action of a pyrogenic exotoxin by an altogether different strategy, using antagonists that inhibit toxin action at the top of the toxicity cascade, before activation of T cells takes place.

The examples describe in detail molecular methods, analysis of pyrogenic exotoxin-mediated activation of the human cellular immune response through expression of IL-2, IFN-γ and TNF-β genes in PBMC, to evaluate toxin antagonist activity. Studies in human PBMC were combined with animal tests to evaluate immunogenic properties and vaccine efficacy and it will be shown that these methods are applicable in devising agents that counteract or protect human PBMC also against other members of the family of pyrogenic exotoxins.

Because humans are far more sensitive to pyrogenic exotoxins than mice, while primate models poses other limitations such as cost, there is a need for a human in vitro system, capable of analyzing the mechanisms of toxin-mediated activation and suppression of the immune response. The present invention provides such a system, which offers major advantages:

(1) freshly prepared human lymphoid cell populations that preserve cell—cell interactions involved in regulation of cytokine production and are as close as possible to the peripheral immune system of the body;

(2) early events of the immune response can be analyzed precisely and directly by following the transient and highly regulated expression of IL-2, IFN-γ and TNF-β mRNA;

(3) expression of IL-2, IFN-γ and TNF-β genes is exquisitely sensitive to activation elicited by SEB;

(4) a molecular approach which is far more direct and specific than measurement of biological responses, such as cell proliferation or antibody production, that are the cumulative result of a sequence of events; and (5) a tool for mapping functional domains in SEB essential for activation of human IL-2, IFN-γ and TNF-β genes, which can serve to facilitate both antagonist and vaccine development.

In a further aspect, the invention relates to a method of inhibiting pyrogenic exotoxin-mediated activation of T-lymphocytes and protecting against toxic shock induced by a pyrogenic exotoxin or by a mixture of pyrogenic exotoxins, in a patient in need of such treatment comprising administering to said patient an inhibitory effective amount of an isolated and purified peptide or of a composition comprising the same. Such peptide has an amino acid sequence homologous to an amino acid sequence of a domain of a pyrogenic exotoxin which domain forms a central turn in the exotoxin starting within β-strand 7 and connecting the β-strand 7, via short β-strand 8, to α-helix 4, and ending within α-helix 4, based on the domain numbering of SEB, and does not have toxin agonist activity.

According to a preferred embodiment, the peptide utilized by the method of the invention may be selected from any peptide having the amino acid sequence of any one of SEQ ID NO:1 to SEQ ID NO:11, SEQ ID NO:14 and SEQ ID NO:15. It is to be appreciated that the method of the invention may also use any mixture of said peptides. More particularly, the peptide used by the method of the invention may be a peptide as defined by the invention.

In yet another example of said aspect, the invention relates to a method of eliciting protective immunity against a toxic shock induced by a pyrogenic exotoxin in a patient in need of such treatment. This method comprises administering to said patient an isolated and purified peptide or an immunogenic composition comprising the same. The peptide used by this method has an amino acid sequence homologous to an amino acid sequence of a domain of a pyrogenic exotoxin which domain forms a central turn in the exotoxin starting within β-strand 7 and connecting the β-strand 7, via short β-strand 8, to α-helix 4, and ending within α-helix 4, based on the domain numbering of SEB, and does not have toxin agonist activity.

In a preferred embodiment, the peptide utilized by this method of the invention, may be selected from any peptide having the amino acid sequence of any one of SEQ ID NO:1 to SEQ ID NO:11, SEQ ID NO:14 and SEQ ID NO:15. Generally, the peptide used by the method of the invention may be any peptide as defined by the invention. It is to be appreciated that any mixture of said peptides may also be used by the method of the invention.

Thus, the invention also relates to a method for treating toxic shock induced by a pyrogenic exotoxin or a mixture of pyrogenic exotoxins. The method comprises administering to a patient in need of such treatment a therapeutically effective amount of the pharmaceutical composition of the invention or a therapeutically effective amount of at least one peptide of the invention, or functional derivative thereof.

In a further embodiment there is provided a method for preventing toxic shock induced by a pyrogenic exotoxin or a mixture of pyrogenic exotoxins comprising administering to a patient in need of such treatment a therapeutically effective amount of a composition of the invention or of a therapeutically effective amount of at least one peptide of the invention or functional derivative thereof.

The invention also relates to a method for immunizing a patient against toxic shock induced by pyrogenic exotoxin, comprising administering to a patient an effective immunizing amount of the vaccine of the invention or of at least one peptide of the invention or functional derivative thereof.

The magnitude of therapeutic dose of the peptide or of the vaccine of the invention will of course vary with the group of patients (age, sex, etc.), the nature of the condition to be treated and with the route administration and will be determined by the attending physician.

The peptides and the vaccines of the invention can be administered and dosed in accordance with good medical practice. In particular, the immunization method of the invention comprises a single administration of the peptides or vaccines of the invention. Administration may be carried out in various ways, including intravenous, intramuscular or subcutaneous injection. However, other methods of administration such as intranasal administration are also possible.

As shown hereafter, antibodies raised against peptides derived from certain SEB protein domains actually enhance the response of human PBMC to SEB and SEA, as expressed by induction of IL-2 and IFN-γ mRNA, rather than protect against these toxins. This would provide a tool for detecting such potential exacerbation by any pyrogenic exotoxin vaccine even before trials with humans are conducted. Design of pyrogenic exotoxin antagonist peptides as described herein may find novel applications not only in hitherto neglected areas, prophylaxis against pyrogenic exotoxins and treatment of toxin-exposed individuals but also may facilitate the development of a safer pyrogenic exotoxin vaccine. A defined peptide vaccine, free of exacerbating properties, would be superior to a toxoid vaccine.

Thus, the invention also relates to antibodies directed against a peptide of the invention, which are capable of blocking T-cell activation by a pyrogenic exotoxin or a mixture of pyrogenic exotoxins, which may be mono- or polyclonal antibodies.

In humans, toxic shock resulting from exposure to pyrogenic exotoxins has two distinct components: (1) incapacitation and (2) death. Even at concentrations several logs below lethal ones, pyrogenic exotoxins severely incapacitate, causing high morbidity [USAMRIID Manual, (1998) Eitzen E, Pavlin J, Cieslak T, Christopher G, Culpepper R, eds. Medical Management of Biological Casualties Handbook. 3rd ed. Fort Detrick, Md.: United States Army Medical Research Institute of Infectious Diseases, 1998]. Incapacitation response observed, e.g. in food poisonings, which may be mass poisonings, affects large numbers of people. Moreover, the incapacitation response may be a military threat and a national security threat. With respect to protection against death, the inventors have shown that peptide antagonists p12A and p14A block toxin-induced death in mice. No symptoms of incapacitation in mice, such as vomiting or diarrhea. Experiments of preventing and/or treating incapacitation were conducted in pigs (Example 17).

Emesis that is, nausea, vomiting, and anorexia are typically a set of neurological symptoms controlled by the midbrain (medulla). Vasomotor and respiratory centers, as well as reflex centers for swallowing and vomiting, are located in the medulla. The vomiting center in the medulla oblongata is the origin of the final common pathway that induces emesis; tweaking the medulla causes vomiting [Hamilton, (1956) Textbook of human anatomy. McMillan & Co Ltd, London]. The vomiting center is actually an intertwined neural network that controls patterns of motor, respiratory, vascular, and salivation processes involved in vomiting. The true vomiting center may be stimulated via several neurological pathways, through distinct types of neurotransmitter receptors in the medulla that respond to dopamine, histamine, acetylcholine, serotonin (5HT), norepinephrine, and glutamine. Anti-emetics (mainly dopamine and serotonin antagonists) work by blocking these receptors.

The effect of these multiple pathways upon the true vomiting center is complex. Within hours of oral exposure of mice to SEB, strong expression of IL-2 and IFN-γ genes is induced in T cells present in the intestinal mucosa [Spiekermann and Nagler-Anderson, (1998) Spiekermann G M, Nagler-Anderson C (1998) J Immunol 161:5825–5831]. The resulting activation of mucosal T cells and the response of other cells in the intestinal mucosa to high levels of Th1 cytokines may thus trigger neurotransmitter release to the brain, to support an essential role of the visceral sensory system. It should be noted that for vomiting, no stimulus is needed from the stomach. The stomach acts as effector of the vomiting reflex, upon receipt of signals from the medulla that are produced in response to a variety of stimuli as explained above. As the irritation of the large intestine moves to the small intestine and finally reaches the anus, diarrhea results.

As will be shown in the following Examples (particularly Example 17 and FIGS. 28 and 29), the inventors have found, and this is an object of the invention, that a pyrogenic exotoxin antagonist strongly reduces toxin-mediated symptoms of incapacitation (resembling the human response to SE intoxication and to early lethal shock). It is likely that the toxins act by targeting the cellular immune response to elicit induction and release of Th1 cytokines that then activate, directly or indirectly, neurons in the medulla to trigger symptoms of incapacitation. Thus, a unitary mode of action of the pyrogenic exotoxin antagonist, blocking the activation of T cells, will account for its ability to prevent both death and incapacitation. The data of FIGS. 28 and 29 establish the reliability of the protective effect of antagonist against toxin incapacitation in the pig model, an animal close to humans in immune response to pyrogenic exotoxins.

The invention thus further relates to a pharmaceutical composition for the treatment of incapacitation induced by at least one pyrogenic exotoxin comprising an isolated and purified peptide having an amino acid sequence homologous to an amino acid sequence of a domain of a pyrogenic exotoxin, which domain forms a central turn in the exotoxin starting within β-strand 7 and connecting the β-strand 7, via short β-strand 8, to α-helix 4, and ending within α-helix 4, based on the domain numbering of SEB. The peptide of the invention comprised within said composition does not have toxin agonist activity. The composition of the invention optionally further comprises pharmaceutically acceptable carrier, diluent, adjuvant and/or excipient.

In one embodiment, the pharmaceutical composition of the invention for the treatment of incapacitation, may comprise as an active ingredient an isolated and purified peptide having the amino acid sequence selected from the group consisting of SEQ ID NO:1 to SEQ ID NO:11 and SEQ ID NO:13 to SEQ ID NO:15 and any combination or mixture thereof, and optionally further comprises pharmaceutically acceptable carrier, diluent, adjuvant and/or excipient.

In one specifically preferred embodiment, this composition of the invention comprises as an active ingredient, a peptide which has the amino acid sequence of SEQ ID NO:2, or of any derivatives thereof. Such derivatives may be for example any of the peptides having the amino acid sequences according to any one of SEQ ID NO: 6 to SEQ ID NO: 11.

In yet another specifically preferred embodiment, the composition for the treatment of incapacitation comprises as an active ingredient, a peptide which has the amino acid sequence of SEQ ID NO:13, or of any derivatives thereof. Such derivatives may be for example any of the peptides having the amino acid sequences according to any one of SEQ ID NO:14 and SEQ ID NO:15.

The composition for the treatment of incapacitation, may comprise as an active ingredient, any of the isolated and purified peptides as defined by the invention and optionally further comprises pharmaceutically acceptable carrier, diluent, adjuvant and/or excipient.

Still further, the invention provides for a method of preventing and/or treating incapacitation induced by at least one pyrogenic exotoxin comprising administering to a patient in need of such treatment at least one therapeutically effective dose of an isolated and purified peptide or of a composition comprising the same. The peptide used by this method has an amino acid sequence homologous to an amino acid sequence of a domain of a pyrogenic exotoxin which domain forms a central turn in the exotoxin starting within β-strand 7 and connecting the β-strand 7, via short β-strand 8, to α-helix 4, and ending within α-helix 4, based on the domain numbering of SEB, and does not have toxin agonist activity.

More particularly, the peptide used by the method of the invention may be a peptide as defined by the invention. Specifically, the peptide utilized by this method of the invention, may be selected from any peptide having the amino acid sequence of any one of SEQ ID NO:1 to SEQ ID NO:11, SEQ ID NO:14 and SEQ ID NO:15. It is to be appreciated that any mixture of said peptides may also be used by the method of the invention. The effective dose of the isolated peptide or composition comprising the same may administered to said patient repeatedly, at predetermined periods of time. Since when entering toxic shock patients are usually given an infusion of salts, admixing the antagonist peptide, readily soluble in water, with said infusion, would allow for its sustained administration over the crisis period, to offset clearance. This may be a preferred and very fast route for the administration of the antagonist. The route of administration, dosage, number and frequency of treatments will be determined by the attending physician.

In addition, the invention also relates to antisera containing antibodies directed against peptides of the invention. For example, peptides such as pSEBLC(150–161) or p12LC (150–161) can be linked through the lauryl cysteine residue to proteosomes. Alternatively, peptides such as those coupled through their C-terminus to a cysteine (C) residue, as described above, can be linked through the cysteine residue to KLH. KLH and proteosomes are known adjuvants for immunization and the peptides so linked are capable of eliciting the production of antibodies.

It is also known in the art that aluminum hydroxide (alum) may be used as an immunization adjuvant directly, with non-linked peptides, or after linking a peptide to proteosomes or to KLH [Lowell et al., (1996) ibid.] or other suitable adjuvants. Therefore, the invention also relates to antisera containing antibodies directed against peptides of the invention, or functional derivatives thereof. The antisera of the invention are capable of alleviating toxic shock induced by a pyrogenic exotoxin. An antiserum according to the invention can be a domestic animal antiserum, for example rabbit, sheep, bovine, equine, porcine or goat antiserum.

For some purposes, for example the in vitro use mentioned above, human sera from immunized individuals can be used.

As already mentioned above, at present there exists no tool for assessing the efficacy of a vaccine against pyrogenic toxins in conferring immunity thereagainst. The present invention provides for such a method and thus, in a further aspect the invention relates to a method for assessing the efficacy of a vaccine for conferring immunity against one or more pyrogenic toxins comprising determining the ability of serum from an immunized individual to antagonize toxin-mediated activation of T cells.

The ability of serum from an immunized individual to antagonize toxin-mediated activation of T cells can be determined by measuring the inhibition of expression of pyrogenic toxin-induced mRNA encoded by the IL-2, IFN-γ, or TNF-β genes. Reference may be made to Example 7 and FIGS. 13 to 15.

A kit for assessing the efficacy of a vaccine for conferring immunity against one or more pyrogenic toxins comprising determining the ability of serum from an immunized individual to antagonize toxin-mediated activation of T cells by the method of the invention is also provided.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Materials and Methods

Cell Culture and Induction of Human Cytokine Gene Expression

PBMC from healthy human donors were separated on Ficoll Paque (Pharmacia), washed twice with 50 ml of RPMI 1640 medium, resuspended at a density of $4 \times 10^6$/ml and cultured in this medium supplemented with 2% fetal calf serum, 2 mM glutamine, 10 mM MEM nonspecific amino acids, 100 mM Na-pyruvate, 10 mM Hepes pH 7.2, $5 \times 10^{-5}$ M 2-mercapto-ethanol, 100 µg/ml penicillin, 100 µg/ml streptomycin and 5 µg/ml nystatin. SEB (lot 14–30, from the Department of Toxicology, U.S. Army Medical Research Institute of Infectious Diseases), SEA or TSST-1 (Sigma) were added to 100 ng/ml.

RNase Protection Analysis

Total RNA was extracted with guanidinium isothiocyanate [Chomczynski and Sacchi, Anal Biochem 162:156 (1987)]. RNase protection analysis was done [Arad et al. (1995) ibid.] using genomic antisense RNA probes transcribed with [$\alpha$-$^{32}$P]UTP in vitro from DNA inserted into pBS (Promega). The IL-2 probe (600 nucleotides (nt)), transcribed from the T7 promoter, is complementary to the third exon and a portion of the third intron of the IL-2 gene; in 8 M urea-polyacrylamide gels, it yields an RNA fragment of 117 nt protected by IL-2 mRNA. The IFN-γ probe (274 nt), transcribed from the T3 promoter, is complementary to the third exon and a portion of the third intron of the IFN-γ gene and yields an RNA fragment of 183 nt protected by IFN-γ mRNA. The TNF-γ probe (700 nt), transcribed from the T3 promoter, is complementary to part of exon 1, exon 2, exon 3, and portions of intron 3 and exon 4; TNF-β mRNA protects 2 fragments of 274 and 263 nt. Sense RNA transcripts yielded no detectable signal upon hybridization. Antisense RNA probes for 18S rRNA (protecting 90 nt) or β-actin (protecting 415 nt) served as loading controls.

Quantitative Dot Blot Hybridization of IL-2 and IFN-γ RNA

PBMC from 1-ml cultures were collected and lysed in 7.5 M guanidinium-HCl. RNA, precipitated overnight in ethanol at −20° C., was dissolved into formaldehyde and incubated for 15 min at 60° C. Four serial 2-fold dilutions, made in 10× saline sodium citrate, were applied in duplicate to nitrocellulose sheets, using a 96-well dot blot apparatus. After baking in a vacuum oven at 80° C., sheets were hybridized separately with $^{32}$P-labeled antisense RNA probes for human IL-2 and IFN-γ, respectively. Exposed autoradiograms were scanned at 630 nm in an ELISA reader. RNA levels are expressed in units of $A_{630}$. Serial twofold dilutions of a given RNA sample yield a linear optical density response over a 200-fold range of intensities of gene expression that is proportional to the concentration of specific RNA present in each sample [Arad et al. (1995) ibid.; Gerez et al., Clin Immunol Immunopathol 58:251 (1991); Kaempfer et al., J Clin Oncol 14:1778 (1996)].

Synthesis of SEB-Related Peptides

Figure 3:
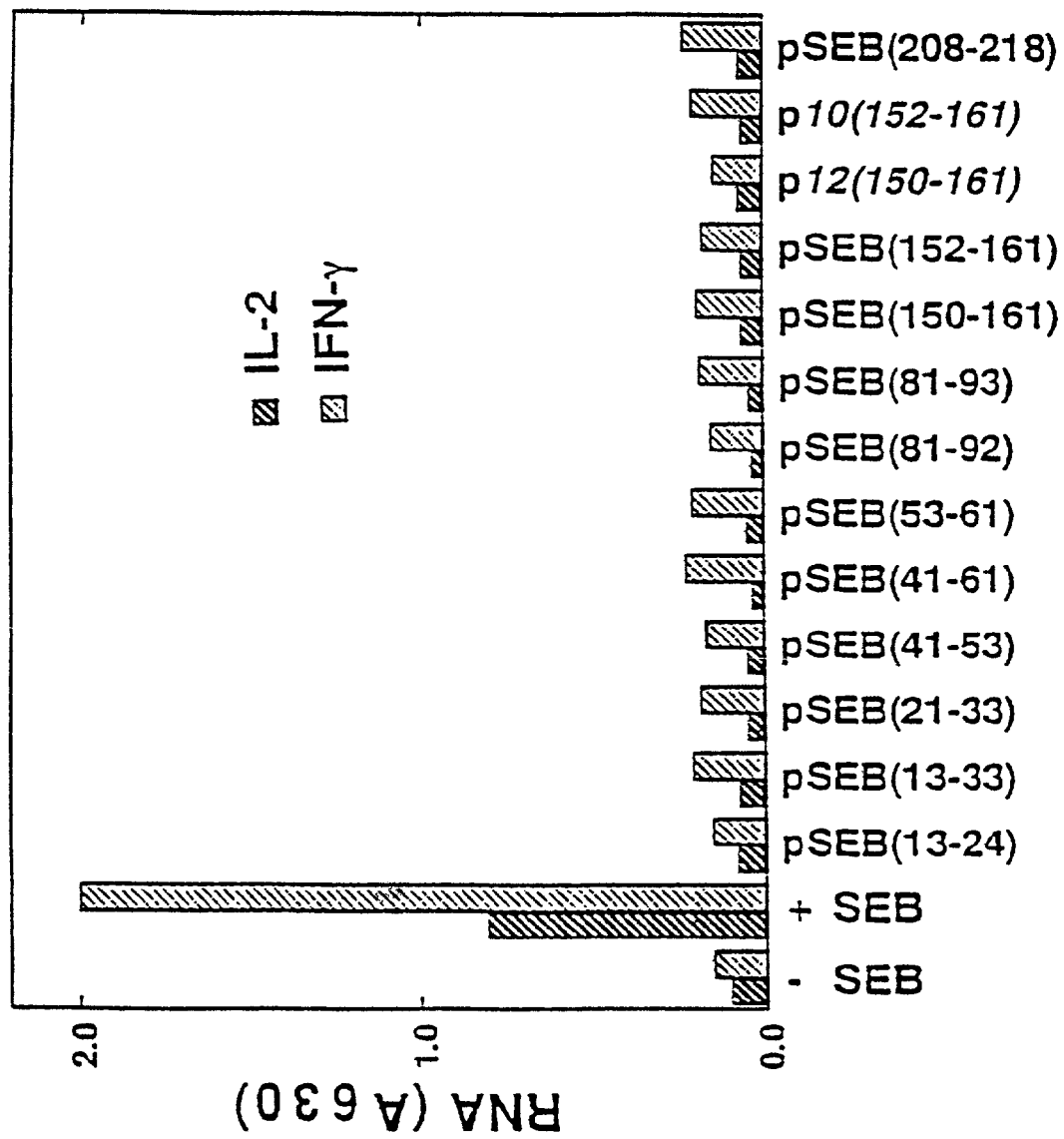
FIG. 3 is a graph showing the lack of SEB agonist activity of SEB-derived peptides. Aliquots of $4\times10^6$ PBMC were induced without inducer (−SEB), with SEB (+SEB), or with 1 μg/ml of one of the indicated SEB-related peptides (Table 2) as sole inducer. Total RNA was extracted after 4 h of induction and serial twofold dilutions were subjected to dot blot hybridization analysis with $^{32}$P-labeled IL-2 and IFN-γ anti-sense RNA probes. Autoradiograms were subjected to microdensitometry at 630 nm; $A_{630}$ is plotted.
Figure 4:
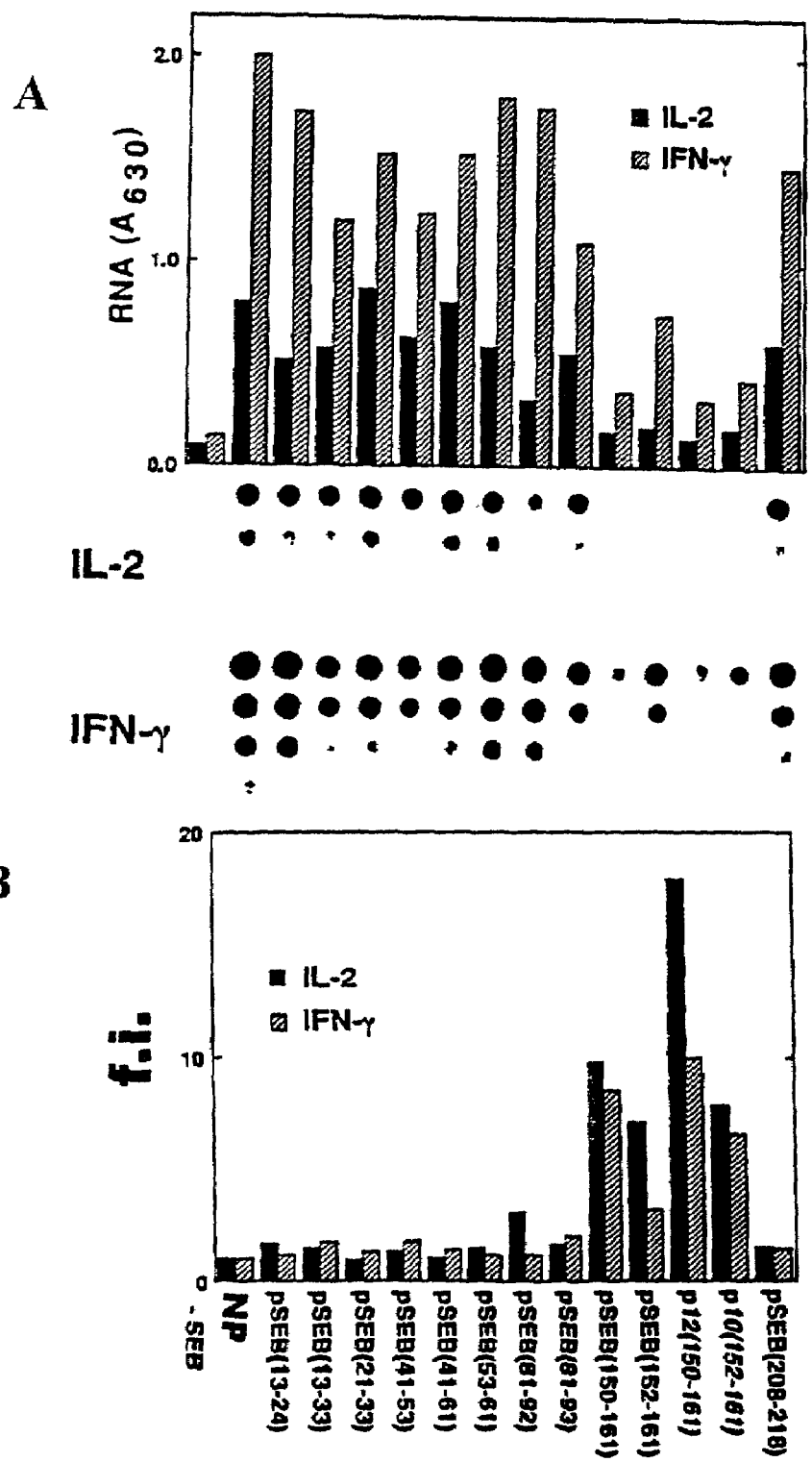
FIGS. 4A–4B are graphs showing the antagonist activity of SEB-related peptides. Aliquots of $4\times10^6$ PBMC were induced without inducer (−SEB), with SEB in the presence of no peptide (NP), or with SEB in the presence of 1 μg/ml of one of the indicated SEB-related peptides (sequences shown in Table 2). Total RNA was extracted after 4 hrs of induction and serial twofold dilutions (vertical rows) were subjected to dot blot hybridization analysis with $^{32}$P-labeled IL-2 and IFN-γ anti-sense RNA probes. Autoradiograms shown were quantitated by densitometry at 630 nm, plotted in (FIG. 4A). Fold inhibition (f.i.) of IL-2 and IFN-γ mRNA expression induced by SEB (FIG. 4B) was calculated from data as shown in (FIG. 4A), by subtracting basal levels of mRNA expressed (−SEB) and dividing extent of mRNA expression induced by SEB alone (NP) by that obtained with SEB in the presence of the indicated SEB-related peptide.
Figure 5:
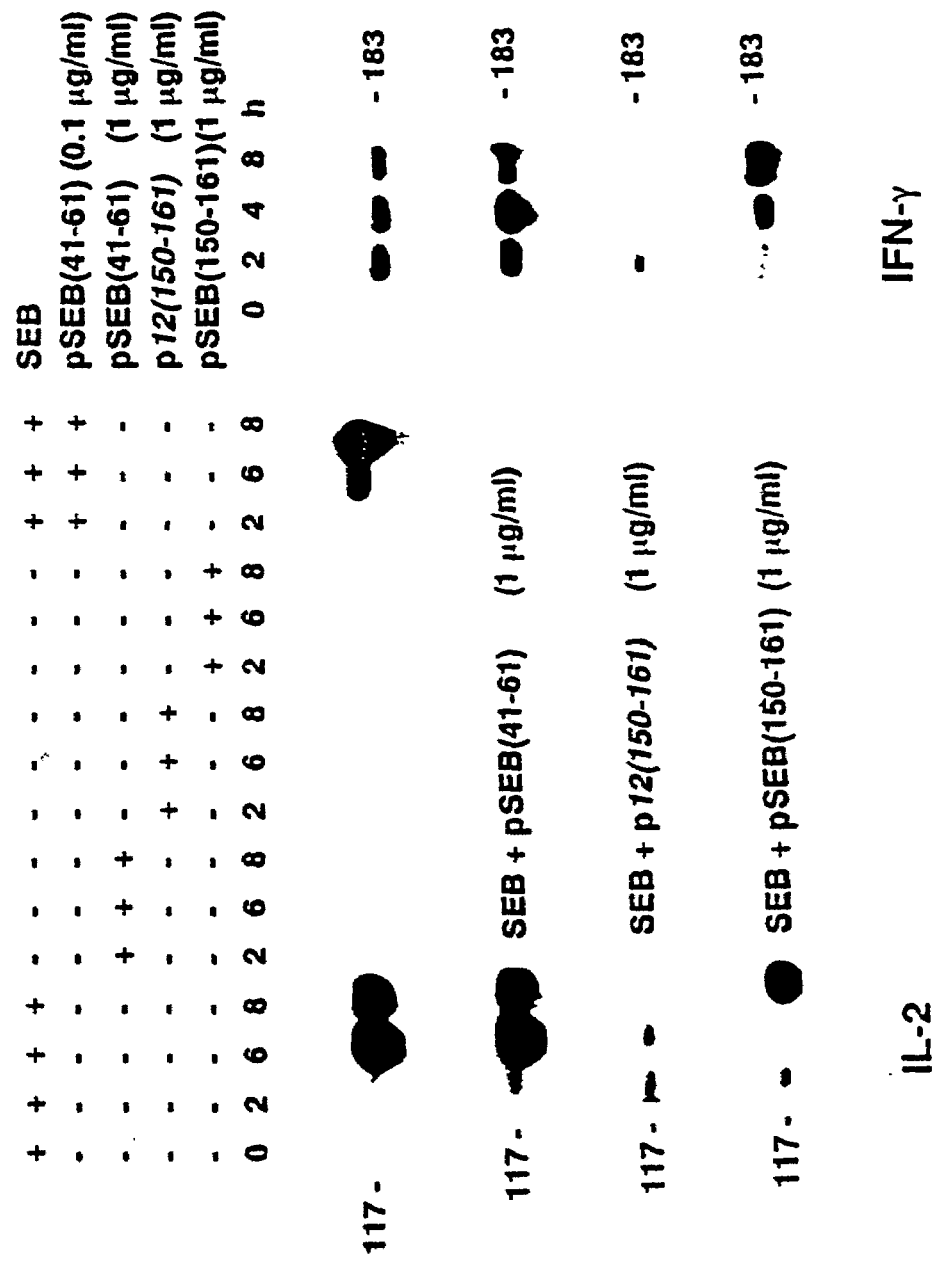
FIG. 5 shows the inhibition of SEB-mediated induction of IL-2 and IFN-γ mRNA by p12(150–161). Aliquots of $3\times10^7$ PBMC were induced with SEB, SEB-related peptides as indicated, or both. At times shown, total RNA was extracted and subjected to RNase protection analysis, using a $^{32}$P-labeled IL-2 or IFN-γ antisense RNA probe as for FIG. 1D. Autoradiograms are shown. Data for IL-2 and IFN-γ are derived from separate experiments.
Figure 6:
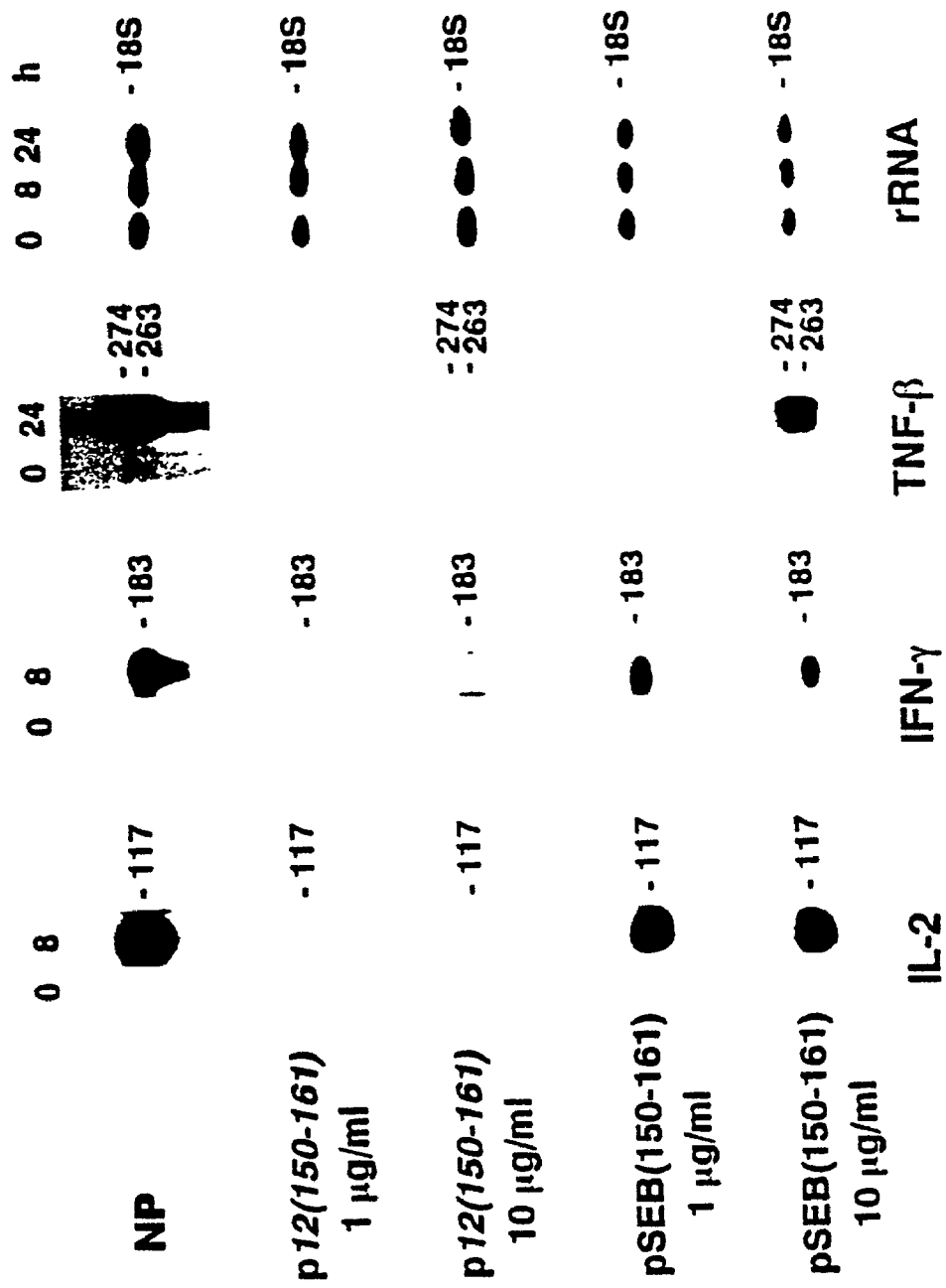
FIG. 6 shows the inhibition of SEB-mediated induction of IL-2, IFN-γ and TNF-β mRNA by p12(150–161). Aliquots of $3\times10^7$ PBMC were induced with SEB, in the presence of no peptide (NP) or of SEB-related peptides as indicated. At times shown, total RNA was extracted and subjected to RNase protection analysis, using a $^{32}$P-labeled IL-2, IFN-γ or TNF-β antisense RNA probe as for FIGS. 1D and 1E. rRNA served as loading control. Autoradiograms are shown.

Peptides were synthesized in the Peptide Synthesis Unit of The Hebrew University-Hadassah Medical School, Jerusalem. tBOC chemistry (tertiary butoxycarbonyl protection of amino termini) was used to prepare one batch of peptides, used for FIGS. 3–5, Table 3, and trials 2 and 3 in Table 4; peptides were cleaved, and the side chain deprotected, with fluoric acid and then solubilized with 10% dimethylsulfoxide. The same amount of dimethylsulfoxide was added to control cell cultures. Fluoronylmethoxycarbonyl (FMOC) chemistry was used to prepare a second batch of peptides, used for FIGS. 6 and 7 and trial 1 in Table 3; peptides were cleaved, and the side chain deprotected, with triflouroacetic acid. Triflouroacetic acid-peptide salts were soluble in culture medium. In the experiment of FIG. 6, corresponding peptides from both batches were also compared and found to have equal antagonist activity. N-terminal laurylcysteine (LC-) and C-terminal cysteine (-C) were added under the same conditions used for the other amino acids. Peptides were >95% purity by HPLC.

Proteosome or KLH Coupling of Peptides

Outer membrane proteosome preparations were stored at −70° C. after purification, as described [Mallett et al., Infect Immun 63:2382–1995)], from group B type 2 *Neisseria meningitidis* by extraction of a paste of phenol-killed bacteria with a solution of 6% Empigen BB (Albright and Wilson, Whitehaven, Cumbria, UK) in 1 M calcium chloride, followed by precipitation with ethanol, solubilization in Tris-buffered saline with EDTA and 1% Empigen BB, reprecipitation with ammonium sulfate, and then resolubilization in the Tris buffer with 1% Empigen BB [Lowell et al (1996) ibid.]. LC-peptides were coupled to proteosomes as described by Lowell et al [Lowell et al. (1996) ibid.]. Maleimide-activated keyhole limpet hemocyanin (KLH) was coupled to C-terminal C residues following instructions of the supplier (Pierce).

Immunization

Rabbits were immunized intramuscularly with 100 µg of proteosome- or KLH-coupled peptides, at 0 and 3 weeks. Three bleeds were performed; data for the third bleed are shown in Table 3. BALB/c mice were immunized with 50–100 µg of proteosome- or KLH-coupled peptides, via the parenteral (intramuscular) or intranasal routes as described by Lowell et al. [Lowell et al. (1996) ibid.]. Blood was collected periodically from rabbits from the ear vein, and from mice from the retroorbital plexus at 3 weeks before challenge with SEB. SEB-specific IgG was assayed by ELISA as [Lowell et al. (1996) ibid.].

SEB Challenge Assays of Vaccine Efficacy In Vivo

Groups of 10 female, BALB/c mice (Harlan, Jerusalem, Israel), aged 10–12 weeks, were sensitized by intraperitoneal (i.p.), parenteral (IM), or intranasal (IN) injection with 20 mg D-galactosamine (Sigma) at the time of challenge with a toxin, as described [Lowell et al. (1996)]. Except for SEB (Sigma), sources of superantigens for murine trials were as detailed for induction of cytokine-gene expression. Lot 14–30 SEB was used for challenge. When present, antagonist peptide was injected i.p. Survival was monitored.

Protection of Mice Against Toxic Shock

Groups of 10 female BALB/c mice (Harlan, Jerusalem, Israel) aged 10–12 weeks were sensitized by intraperitoneal (i.p.) injection with 20 mg D-galactosamine (Sigma) at the time of challenge with a toxin, injected i.p.

Protection of Pigs Against Toxic Shock

Five-day old mixed breed pigs (mainly Yorkshire; 2.5 kg) in randomized groups of 6 piglets for each test condition, each group under its own sow, were injected IP with SEA (25 μg). Antagonist peptide was administered IP, 30 min before SEA, and at times as indicated in the Figures, up to 5 h post-SEA. Vomiting and diarrhea were scored at hourly intervals until 8 h and then every 3 h until 12 h, and again at 21 and 24 h.

Structural Analysis

Molecular modeling was based on the atomic coordinates derived by X-ray diffraction for SEB [Protein Data Bank (PDB) code 1SEB; Swaminathan, S. et al., Nature 359, 801–805 (1992); Jardetzky, T. S. et al., Nature 368, 711–718 (1994); Li, H. et al., Immunity 9, 807–816 (1998); Papageorgiou, A. et al., J Mol Biol 277, 61–79 (1998); Leder, L. et al., J Exp Med 187, 823–833 (1998)], SEA (PDB code 1SEA) [Schad, E. M. et al., EMBO J. 14, 3292–3301], and TSST-1 (PDB code 1TSS) [Prasad, G. S., et al., Biochemistry 32, 13761–13766 (1993)], and on the predicted atomic coordinates for SPEA (PDB code SPEA_STRPY).

Example 1

Induction of IL-2, IFN-γ and TNF-β Gene Expression by SEB

Peripheral blood mononuclear cells (PBMC) are used to provide a quantitative measure of the primary response of human T cells to an exotoxin, through expression of the Th1 type cytokine genes encoding IL-2, IFN-γ and TNF-β. Gene expression is analyzed within hours after stimulation, providing a more direct and immediate measure of the action of SEB than cell proliferation which results from a complex series of events.

Figure 1:
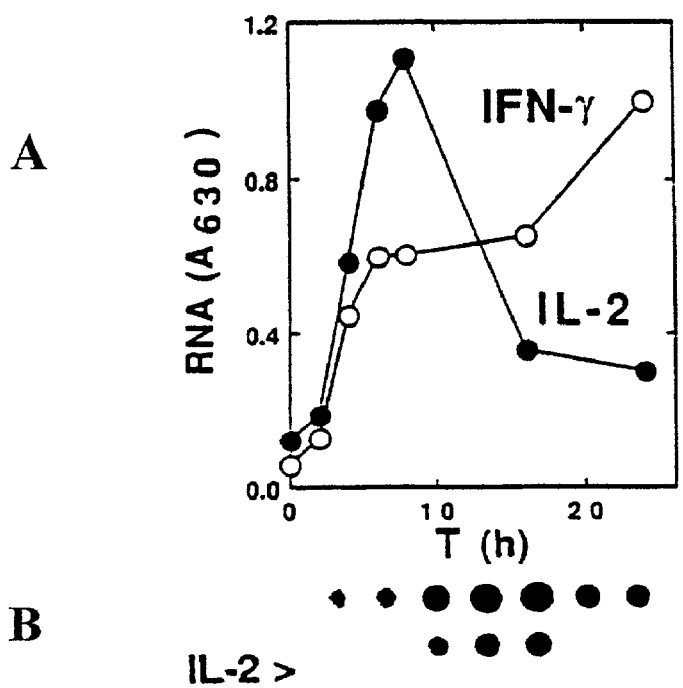
FIGS. 1A–1E show the induction of IL-2, IFN-γ and TNF-β gene expression by SEB. Aliquots of $4\times10^6$ human PBMC were induced with SEB. Total RNA was extracted at times indicated [T(h)] and serial twofold dilutions (vertical rows) were subjected to dot blot hybridization analysis with $^{32}$P-labeled IL-2 and IFN-γ anti-sense RNA probes; autoradiograms (FIGS. 1B, 1C) were quantitated by densitometry at 630 nm, plotted in FIG. 1A. In separate experiments, aliquots of $3\times10^7$ human PBMC were induced with SEB and total RNA was extracted at times indicated. IL-2, IFN-γ (FIG. 1D) and TNF-β mRNA (FIG. 1E) were quantitated by RNase protection analysis. IL-2 mRNA protects a fragment of 117 nt; IFN-γ mRNA protects a fragment of 183 nt; TNF-β mRNA protects 2 fragments of 274 and 263 nt. β-Actin RNA served as loading control.

Exposure of PBMC to SEB leads to induction of IL-2 and IFN-γ mRNA, shown by quantitative dot blot hybridization (FIGS. 1A–1C) and RNase protection analysis with a genomic antisense RNA probe (FIG. 1D). Both methods yield similar patterns of induction, characterized by a transient wave of IL-2 mRNA and more prolonged expression of IFN-γ mRNA. TNF-β mRNA was induced more gradually (FIG. 1E). Patterns of mRNA have thus been documented to reflect the expression of the active proteins.

Example 2

Design of SEB-Related Peptides

Figure 2:
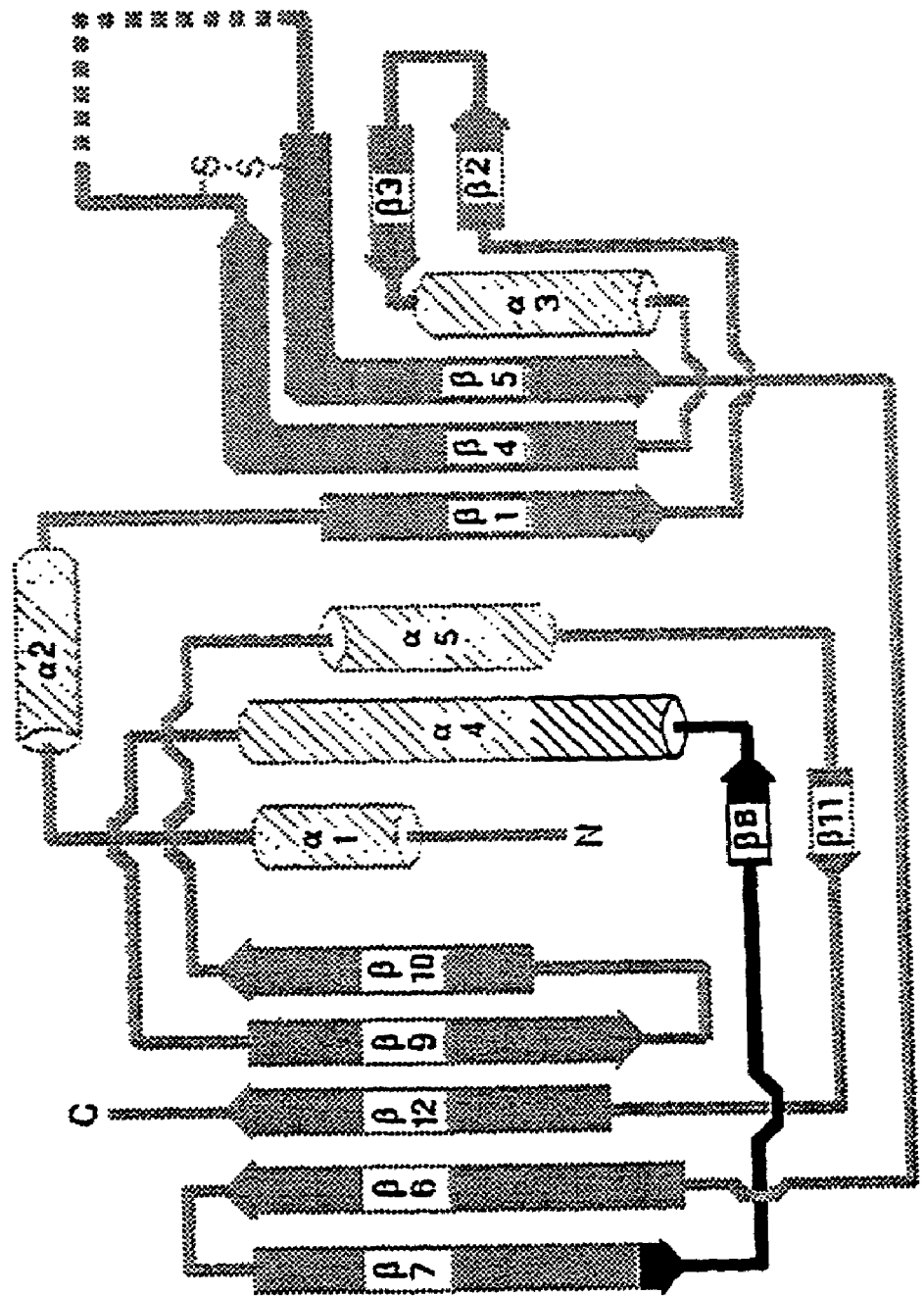
FIG. 2 shows the secondary structure domains within the SEB protein molecule. The two structural domains of the molecule are seen clearly. Cylinders and arrows represent α-helices and β-strands, respectively. The residues forming the secondary structural elements are: 13–17 (α1), 21–29 (α2), 33–39 (β1), 48–52 (β2)63–68 (β3), 70–78 (α3), 81–89 (β4), 112–120 (β5), 127–138 (β141–151 (β7), 154–156 (β8), 157–172 (α4), 182–190 (β9), 195–200 (β10), 210–217 (α5), 222–224 (β11), and 229–236 (β12). Black domain covers pSEB(150–161) and p12(150–161) (see Table 2). Adapted from Swaminathan et al. [Swaminathan et al., Nature 359:801 (1992)].

Fourteen peptides representing particular SEB domains were synthesized (Table 2; peptides were >95% purity by HPLC) and assayed for the ability to block SEB-mediated induction of IL-2, IFN-γ or TNF-β gene expression. Identification of such a peptide could be useful for developing a peptide vaccine against SEB and more directly, for preventing the harmful effects of SEB on the immune response. Multiple, widely separated regions within SEB interact with the TCR on one hand and with the MHC class II molecule on the other [Swaminathan et al. (1992) ibid.; Jardetzky et al., Nature 368:711 (1994)]. Domains chosen consist of amino acid residues 13–33, 41–61, 81–93 and 208–218, essential for binding to TCR and MHC class II; residues 21–29 and 48–61, essential for binding to the TCR; and residues 13–17 and 44–52, essential for binding to MHC class II [Swaminathan et al. (1992) ibid.]. A 12-amino acid SEB domain, made up of residues 150–161, is thought not to be involved in binding to TCR or MHC class II but forms a central turn starting within β-strand 7 and connecting β-strand 7, via short β-strand 8, to α-helix 4, and ending with α-helix 4 (Table 2 and FIG. 2). These sequences are found in the SEB molecule, except for two variants of that domain devised by the inventors: dodecamer p12(150–161) and decamer p10(152–161) (150–161* and 152–161* in Table 2, respectively).

To allow study of their immunogenicity and ability to elicit protective immunity against SEB, many of the peptides were synthesized also with an extra lauryl-cysteine residue at their N-terminus (LC-) or with an extra cysteine residue at their C-terminus (-C), as indicated in Table 2.

TABLE 2

SEB-related peptides prepared for this study

| Position | Amino acid sequence | LC- | -C | SEQ ID NO: |
|---|---|---|---|---|
| 13–24 | K S S K F T G L M E N M | + | − | 16 |
| 13–33 | K S S K F T G L M E N M K V L Y D D N H V | + | + | 17 |
| 21–33 | M E N M K V L Y D D N H V | + | + | 18 |
| 41–53 | I D Q F L Y F D L I Y S I | − | − | 19 |
| 41–61 | I D Q F L Y F D L I Y S I K D T K L G N Y | + | + | 20 |
| 51–61@ | Y S I K D T K L G N Y | − | + | 21 |
| 53–61 | I K D T K L G N Y | + | − | 22 |
| 81–92 | Y V D V F G A N Y Y Y Q | + | − | 23 |
| 81–93 | Y V D V F G A N Y Y Y Q C | − | − | 24 |
| 150–161 | T N K K K V T A Q E L D | + | − | 1 |

TABLE 2-continued

SEB-related peptides prepared for this study

| Position | Amino acid sequence | LC- | -C | SEQ ID NO: |
|---|---|---|---|---|
| 150–161* | <u>Y</u> N K K K <u>A</u> T <u>V</u> Q E L D | + | – | 2 |
| 152–161 | K K K V T A Q E L D | – | – | 3 |
| 152–161* | K K K <u>A</u> T <u>V</u> Q E L D | – | – | 4 |
| 208–218 | F D Q S K Y L M M Y N | + | + | 25 |

LC- Lauryl-cysteyl residue added at N-terminus
-C Cysteyl residue added at C-terminus
@Only the -C form was studied
*Variant of the natural SEB sequence

Example 3

Lack of SEB Agonist Activity of SEB-Derived Peptides

SEB agonist activity of peptides was examined by the ability to induce expression of IL-2 and IFN-γ genes. Even when present in 200-fold higher molar amounts than SEB, no peptide exhibited significant SEB agonist activity, defined as ≧2-fold increase in RNA over basal level (FIG. 3). When induction of mRNA for IL-2 (FIG. 5) or IFN-γ (not shown) was analyzed by RNase protection, pSEB(41–61), p12(150–161) and pSEB(150–161) again failed to show SEB agonist activity.

Example 4

Peptide p12(150–161) is an SEB Antagonist

Antagonist activity of SEB-related peptides was defined by the ability to block SEB-mediated induction of IL-2, IFN-γ and/or TNF-β gene expression in PBMC. A short, unstructured peptide would be expected to compete poorly with intact SEB whose binding is stabilized by multiple interactions with the TCR and MHC class II molecule [Swaminathan et al. (1992) ibid.; Jardetzky et al. (1994) ibid.]. However, an appropriate SEB-related peptide might compete with SEB for one of its cognate sites, preventing thereby a cooperative interaction with multiple sites.

Ability to antagonize induction of IL-2 or IFN-γ gene expression was assayed by exposing PBMC populations to SEB in the presence of a 100- to 200-fold molar excess of an individual peptide. The resulting hybridization patterns for IL-2 and IFN-γ RNA are shown and quantitated in FIG. 4A. Antagonist activity is seen more clearly in FIG. 4B where extent of inhibition is plotted. Most peptides failed to inhibit SEB-mediated IL-2 mRNA induction perceptibly but pronounced antagonist activity was exhibited by peptides pSEB(150–161), pSEB(152–161), p12(150–161) and p10 (152–161). Dodecapeptide p12(150–161) (SEQ ID NO:2) stands out as antagonist, inhibiting expression of IL-2 mRNA by 18-fold and that of IFN-γ mRNA by 10-fold. Peptide p10(152–161) (SEQ ID NO:4), which lacks the 2 N-terminal amino acids of p12(150–161), showed lower, yet still significant, antagonist activity. In >5 experiments, each performed with a distinct PBMC population, SEB antagonist activity of p12(150–161) ranged from 9- to 40-fold inhibition of IL-2 gene induction. Corresponding extent of inhibition by p10(152–161) was up to 8-fold, other peptides remaining well below this value.

PBMC cultured with either pSEB(150–161) or p12 (150–161) showed undiminished viability, as judged by trypan blue exclusion analysis and recovery of total cellular RNA. The SEB antagonist activity of these peptides thus does not result from a cytotoxic effect. Both peptides reproducibly failed to inhibit PHA-mediated induction of IL-2 and IFN-γ genes (not shown).

The natural homolog of p12(150–161), pSEB(150–161), was less active than the variant peptide as SEB antagonist (FIG. 4). Clear differences in antagonist activity between p12(150–161) and pSEB(150–161) are seen in FIGS. 5 and 6. Whereas pSEB(41–61), chosen as control, failed to block induction of IL-2 and IFN-γ mRNA by SEB, p12(150–161) yielded an almost complete inhibition (FIG. 5). pSEB (150–161) inhibited expression of IL-2 mRNA effectively at 6 hrs, but only partially at 8 hrs and reduced expression of IFN-γ mRNA by 2 hrs but not thereafter; a stimulatory effect seen at later times (FIG. 5) was not observed consistently (cf. FIG. 6). In the experiment of FIG. 6, p12(150–161) blocked induction of IL-2, IFN-γ and TNF-β mRNA completely, whereas pSEB(150–161) caused only partial inhibition. p12(1–161) was consistently more effective than pSEB(150–161) as SEB antagonist.

None of the peptides homologous to toxin domains involved in the interaction with T cell receptor and/or MHC class II molecule was able to inhibit the SEB-mediated induction of human IL-2, IFN-γ and TNF-β genes. By contrast, the inventors have identified 12-mer p12 (150–161), resembling a region well removed from these active sites which has the capacity to completely block expression of these cytokine genes upon their induction by SEB. The sequence of this potent antagonist peptide is man-made, deviating at various positions from the corresponding sequence in SEB; indeed, when a peptide with the natural SEB sequence was used, pSEB(150–161), it was less effective as antagonist. Antagonist activity decreased upon removal of 2 N-terminal amino acids. Despite its high degree of conservation, the charge of the corresponding sequence in SEA is neutral whilst that of pSEB(150–161) or of p12(150–161), is positive. Indeed, although SEB is 68% homologous with SEC, it shows only 27% homology with SEA [Betley and Mekalanos, J Bacteriol 170:34 (1995)].

The region covering amino acids 150–161 overlaps partially with a larger, 31-amino acid peptide, pSEB(130–160). When conjugated to KLH, pSEB(130–160) inhibited the SEB-induced proliferation of mixed cultures of human peripheral blood monocytes and lymphocytes by 2- to 4-fold but was not unique in this property, since peptides overlapping with other SEB domains, covering amino acids 1–30, 61–92, 93–112, 151–180, 171–200 and 191–220, had a similar inhibitory effect [Jett et al. (1994) ibid.]. Although pSEB(130–160) was able to inhibit binding of SEB to human lymphocytes [Jett et al. (1994) ibid., Komisar et al., Infect Immun 62:4775 (1994)] it was shown that a smaller overlapping peptide, pSEB(150–162), failed to inhibit binding of SEB to HUT-78 cells, a human T cell line, as studied by fluorescence, whereas another peptide, pSEB(90–114), inhibited by 2-fold. Wang et al. [(1993) ibid.] showed that a synthetic peptide encoding the carboxy-terminal 41 amino acids of the superantigenic pep M5 protein of *S. pyogenes* inhibited pep M5-mediated T cell proliferation. They commented with respect to pSEB(152–160) that "most studies seem to indicate that this region does not contribute to mitogenicity" while emphasizing in this context that "immunologic function is not determined solely by the primary amino acid structure of a particular region but is influenced by the context in which it is located" and indicating that the longer amino acid sequence may contribute to α-helix amphiphilicity. The lack of inductive activity of pSEB (150–161) or p12(150–161) is shown in FIG. 3 for the IL-2 and IFN-γ genes and again for the IL-2 gene in FIG. 5. Indeed, the N-terminal 138 amino acids of SEB, which exclude the domain of pSEB(150–161), are sufficient for mitogenic activity [Buelow et al., J Immunol 148:1 (1992); Kappler et al., J Exp Med 175:387 (1992)]. Thus, it would be expected from these earlier studies that short peptides, especially in the region of pSEB(150–161), will not inhibit the action of SEB. Contrary to this expectation, the results of FIGS. 4–6 show that pSEB(150–161) and the non-natural p12(150–161) are powerful SEB antagonists.

Example 5

Enhancement of SEB Antagonist Activity

Figure 7:
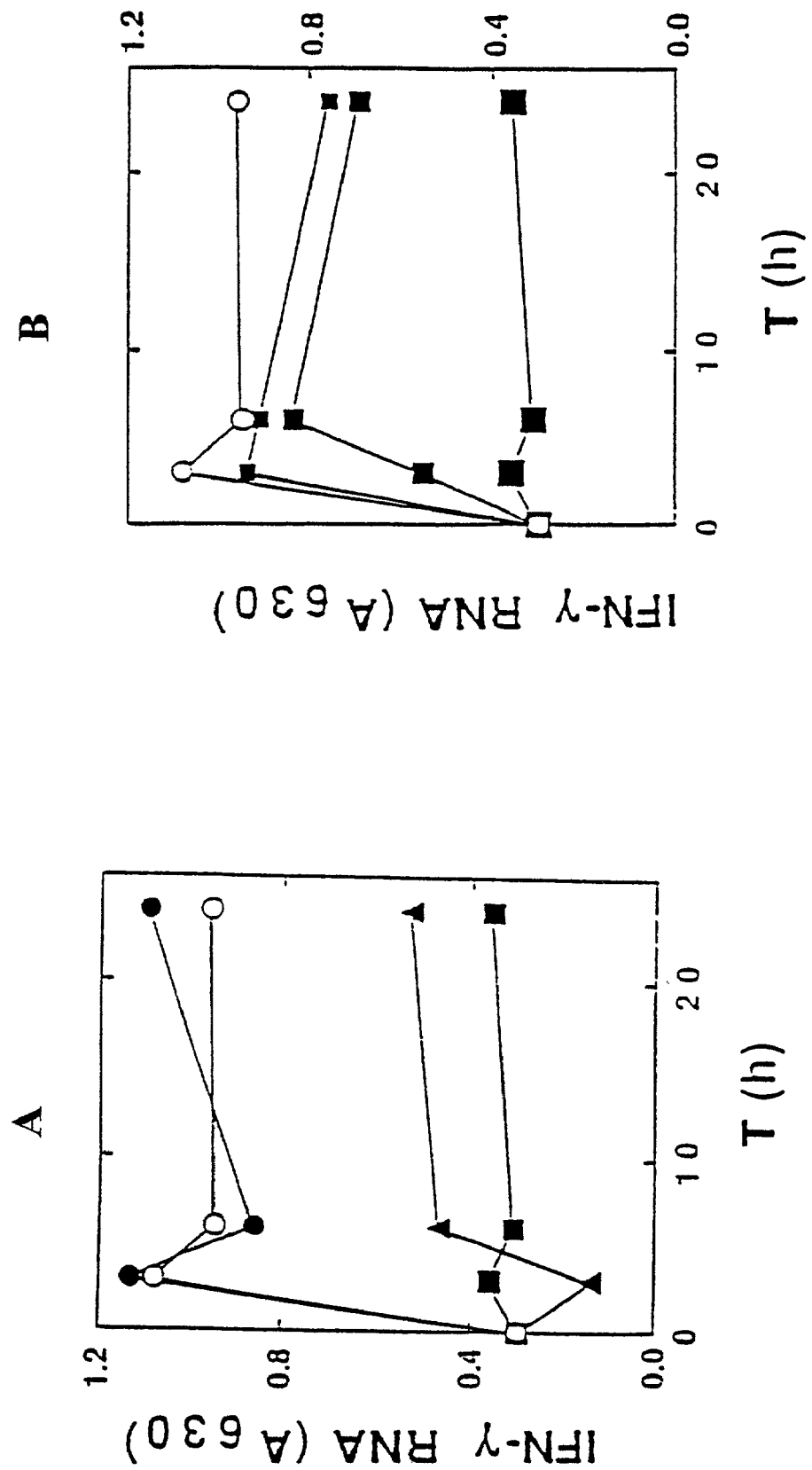
FIGS. 7A–7B are graphs showing the SEB antagonist activity of p12(150–161) monomer, dimer and trimer.

With PBMC populations from occasional healthy donors, it was observed that p12(150–161) was only weakly or not inhibitory to SEB. Such an experiment is illustrated in FIG. 7. Whereas p12(150–161) did not inhibit induction of IL-2 and IFN-γ mRNA, both its dimer and trimer forms were strongly inhibitory (shown for IFN-γ in FIG. 7A). FIG. 7B shows that even when diluted 100-fold, the dimer still gave a detectable inhibition.

Figure 8:
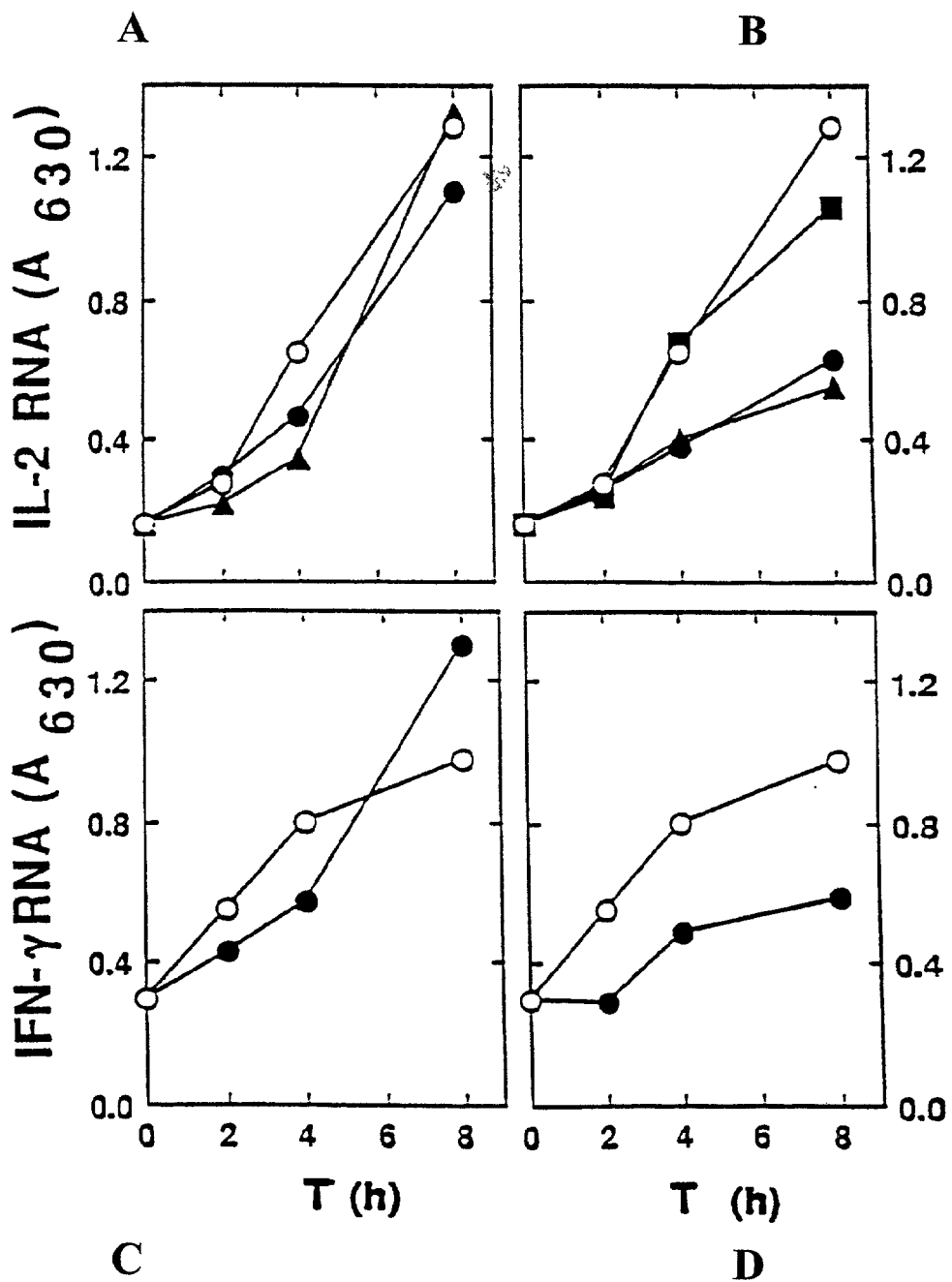
FIGS. 8A–8D show the SEB antagonist activity of Cys-p12(150–161). Aliquots of $4\times10^6$ PBMC were induced with 100 ng/ml of SEB alone (open circles), or with SEB in the presence of undiluted peptide (filled triangles) (in 420-fold molar excess over SEB), or of peptide diluted 1:10 (filled circles) or 1:100 (filled squares).

A similar rise in efficacy was observed when p12 (150–161) was cyclized with terminal cysteines (Cys-p12 (150–161)) (FIG. 8). Given the oxidizing conditions in aqueous solution, this peptide will tend to cyclize by forming an intramolecular disulfide bridge in a zero-order reaction; multimeric forms generated by disulfide bridges between separate peptide molecules will tend to be rarer as they result from a higher order reaction. Whereas p12 (150–161) was weakly or not inhibitory at 8 hrs (FIGS. 8A and 8C), Cys-p12(150–161) showed significant SEB antagonist activity, even upon tenfold dilution (FIGS. 8B and 8D). An enhancement in SEB antagonist activity was also obtained by addition of a D-Ala residue at both N- and C-termini (see FIGS. 11 and 12 below).

Example 6

Broad-Spectrum Pyrogenic Exotoxin Antagonist Activity

The SEB 150–161 domain is conserved among pyrogenic toxins. The sequence of p12(150–161), shown in SEQ ID NO: 2, differs in several positions from the corresponding sequence in SEB, TNKKKVTAQELD (SEQ ID NO: 1) found in pSEB(150–161), but shared KK and QELD motifs are spaced equally in both peptides. Residues T 150, K152, E159 and D161 of this SEB domain are conserved among all staphylococcal enterotoxins [Swaminathan et al. (1992) ibid.]. Indeed, domain 150–161 of SEB is highly conserved among pyrogenic toxins, with 10/12 identities for SEA, SEC1, SEC2, and SPE A and 9/12 for SEE [Bohach and Schlievert (1987) ibid.; Couch et al. (1988) ibid.; Bohach and Schlievert (1989) ibid.]. All of these toxins contain the residues underlined above [Swaminathan et al. (1992) ibid.; Bohach and Schlievert (1987) ibid.; Couch et al. (1988) ibid.; Bohach and Schlievert (1989) ibid.].

Figure 9:
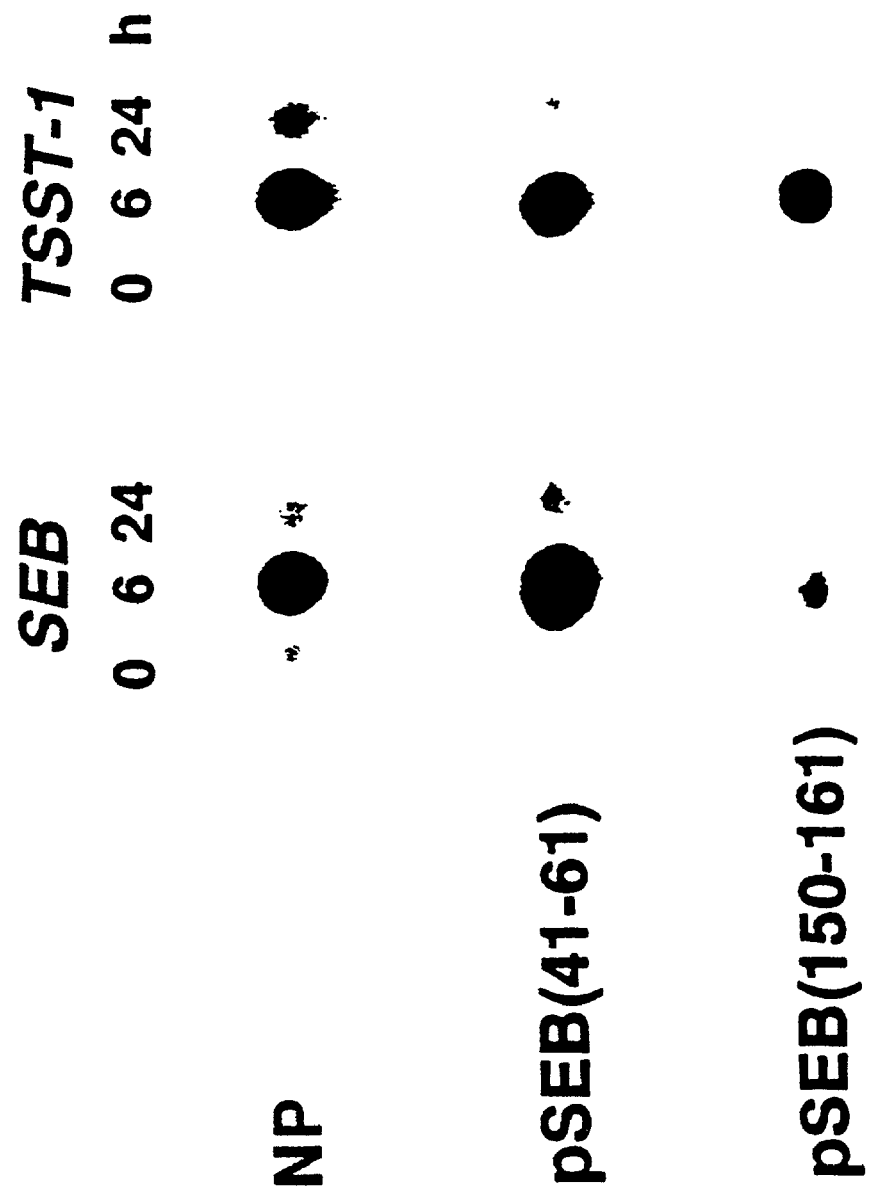
FIG. 9 shows the lack of antagonist activity of pSEB (150–161) for TSST-1. Aliquots of $3\times10^7$ PBMC were induced with SEB or TSST-1 as shown, in the presence of no peptide (NP) or of 1 μg/ml of pSEB(41–61) or pSEB (150–161) as indicated. At times shown (h), total RNA was extracted and subjected to RNase protection analysis, using a $^{32}$P-labeled IL-2 antisense RNA probe as for FIG. 1D.
Figure 10:
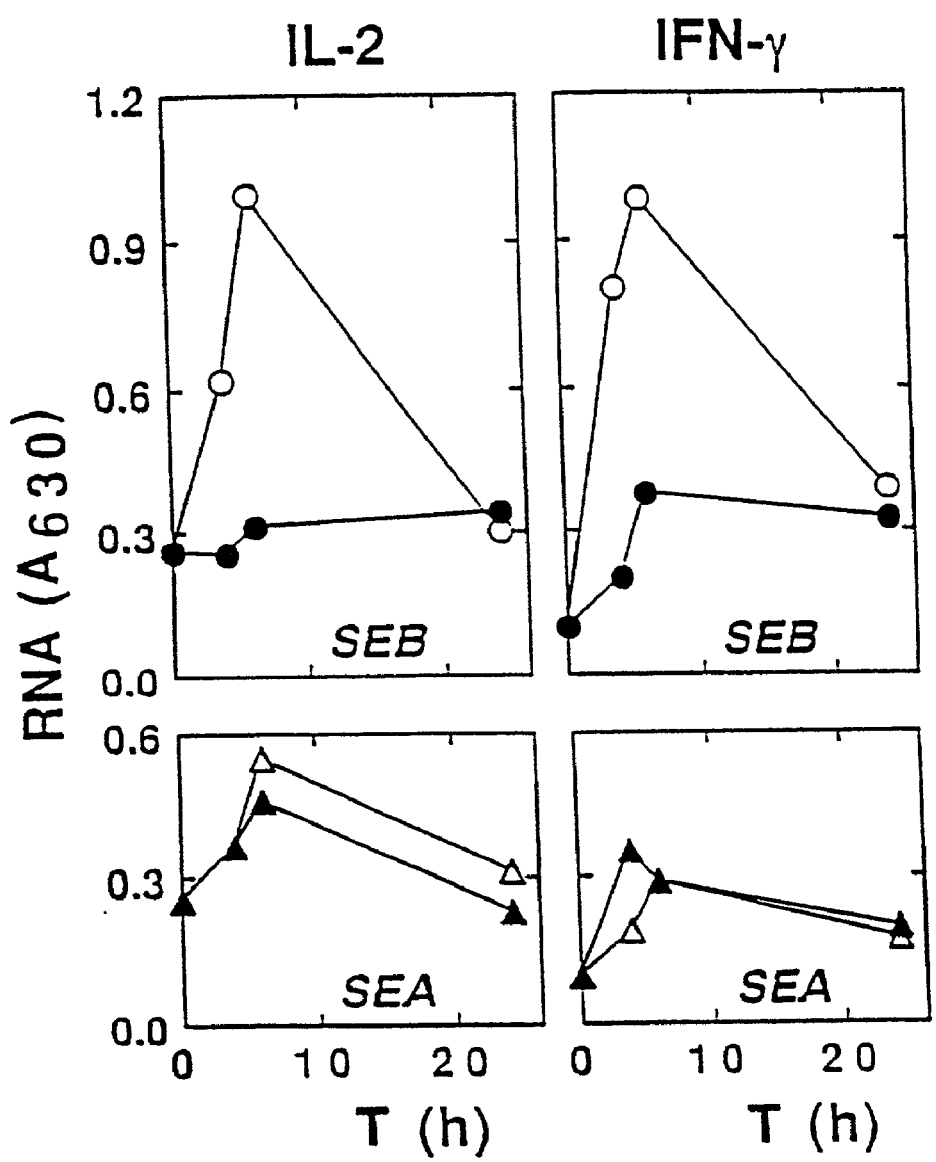
FIGS. 10A–10D show the lack of antagonist activity of p12(150–161) for SEA. Aliquots of $4\times10^6$ human PBMC were induced with SEB (FIGS. 10A, 10B) or SEA (FIGS. 10C, 10D), in the absence (open circles, open triangles) or presence (filled circles, filled triangles) of 1 μg/ml of peptide p12(150–161). Total RNA was extracted at times [T(h)] indicated and serial twofold dilutions were subjected to dot blot hybridization analysis with $^{32}$P-labeled IL-2 (FIGS. 10A, 10C) and IFN-γ (FIGS. 10B, 10D) anti-sense RNA probes. Autoradiograms were quantitated by densitometry at 630 nm.

The prediction that SEB antagonist peptides may have wider antagonist activity was tested. FIG. 9 shows that pSEB(150–161) failed to inhibit the induction of IL-2 mRNA by TSST-1, although it strongly reduced the induction of this mRNA by SEB. As seen in FIG. 10, moreover, p12(150–161) effectively inhibited the induction by SEB of waves of IL-2 mRNA (A) and IFN-γ mRNA (B) but had no significant effect on their induction by SEA.

The results of FIGS. 9 and 10 lend support to the earlier conclusion that the antagonist activity of pSEB(150–161) and p12(150–161) for SEB does not result from a cytotoxic effect on the cells examined because these peptides fail to inhibit induction by TSST-1 and SEA.

These results would lead a man of the art to the conclusion that the SEB antagonist activity of the peptides examined does not extend to two less related toxins, TSST-1 and SEA.

Figure 11:
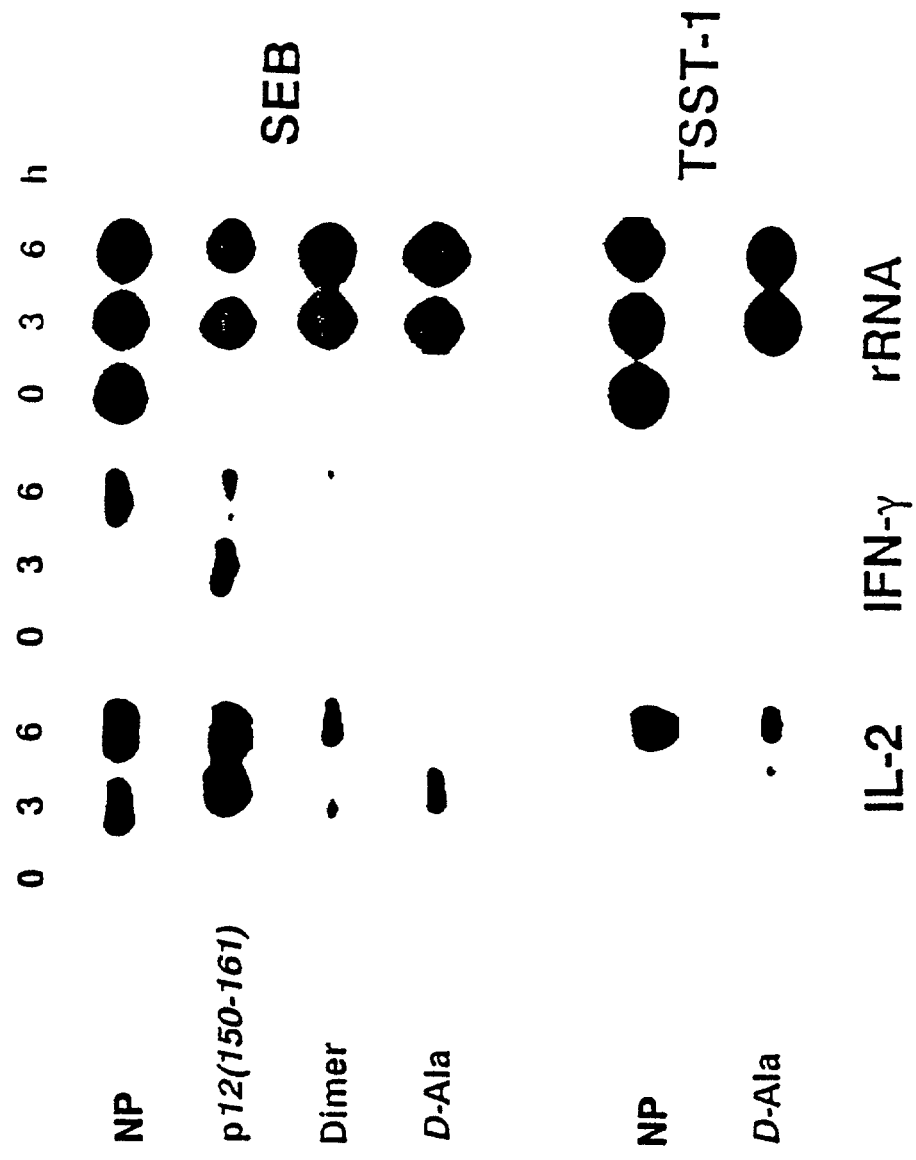
FIG. 11 shows the toxin antagonist activity of p12 (150–161) dimer and D-Ala forms: for SEB and TSST-1. Aliquots of $3\times10^7$ PBMC were induced with SEB or TSST-1 as indicated, in the presence of no peptide (NP) or of 10 μg/ml of p12(150–161) or, where indicated, an equal molar concentration of p12(150–161) dimer (dimer) or of p12 (150–161) carrying a D-Ala residue at both N- and C-termini (D-Ala). At times shown, total RNA was extracted and subjected to RNase protection analysis, using $^{32}$P-labeled IL-2 and IFN-γ antisense RNA probes as for FIG. 1D. rRNA served as loading control.
Figure 12:
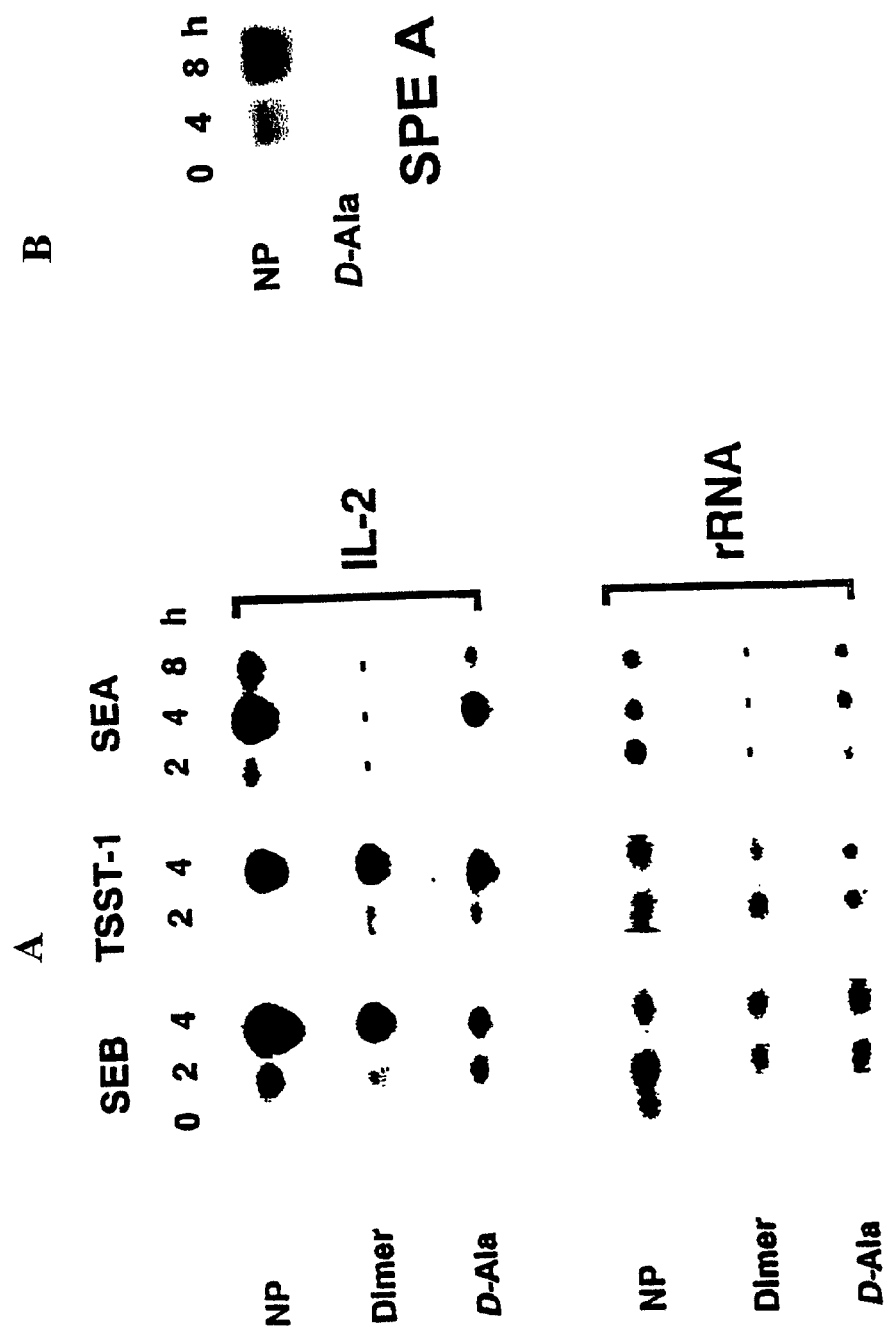
FIGS. 12A–12B show the toxin antagonist activity of p12(150–161) dimer and D-Ala forms: SEB, TSST-1, SEA and SPE A. Aliquots of $3\times10^7$ PBMC were induced with SEB, TSST-1 or SEA as indicated, in the presence of no peptide (NP), p12(150–161) dimer (dimer) or p12(150–161) carrying a D-Ala residue at both N- and C-termini (D-Ala), each of the latter at a molar concentration equivalent to 10 μg/ml of p12(150–161) (FIG. 12A). At times shown, total RNA was extracted and subjected to RNase protection analysis, using $^{32}$P-labeled IL-2 antisense RNA probe as for FIG. 1D. rRNA served as loading control. In addition, aliquots of $3\times10^7$ PBMC were induced with 100 ng/ml of SPE A, in the presence of no peptide (NP) or of p12 (150–161) carrying a D-Ala residue at both N- and C-termini (D-Ala) at a molar concentration equivalent to 10 μg/ml of p12(150–161) (FIG. 12B). At times shown, total RNA was extracted and subjected to RNase protection analysis, using $^{32}$P-labeled IL-2 antisense RNA probe as for FIG. 1D.

Nevertheless, in contrast to the results of FIGS. 9 and 10 which suggest narrow specificity for the antagonist peptides, FIGS. 11 and 12 show that broad-spectrum antagonist activity is exhibited by derivatives of p12(150–161), the dimer described in FIG. 7 and p12(150–161) carrying D-Ala at both N- and C-termini.

FIG. 11 shows induction of IL-2 and IFN-γ mRNA in a PBMC population where peptide p12(150–161) did not significantly inhibit SEB-induced gene expression. However, both dimer and p12(150–161) carrying D-Ala at both N- and C-termini were effective as antagonist, with the latter showing highest antagonist activity. Despite the low homology between corresponding regions in SEB and TSST-1 (FIG. 12A), the D-Ala form also inhibited induction of IL-2 mRNA by TSST-1 (6-hour point in FIG. 11).

FIG. 12A shows, for another PBMC population, induction of IL-2 mRNA by SEB, by TSST-1 as well as by SEA. Induction of IL-2 mRNA by all three toxins was inhibited by p12(150–161) carrying D-Ala at both N- and C-termini. For SEB and TSST-1, data with the dimer of p12(150–161) are also shown. Induction of IL-2 mRNA by both toxins was inhibited by the dimer.

Induction of IL-2 mRNA by SPE A for another PMBC population is depicted in FIG. 12B. Induction of IL-2 mRNA was inhibited by p12(150–161) carrying D-Ala at both N- and C-termini.

The results of FIGS. 12A–12B show that the SEB antagonist activity of the p12(150–161) dimer and/or D-Ala forms extends to other members of the pyrogenic exotoxin family, TSST-1, SEA and the streptococcal SPE A, indicating their potential broad-spectrum toxin antagonist activity. The dimer, Cys and D-Ala forms are each more powerful as antagonist than p12(150–161) (FIGS. 7, 8 and 10). Independent of the basis for enhanced antagonist activity in p12(150–161) derivatives (they may be more stable, exhibit higher affinity for a target, or both), these results show that the sequence of p12(150–161) has the potential of being a broad-spectrum pyrogenic exotoxin antagonist.

Example 7

Antiserum Against p12(150–161) Blocks the Action of SEB, SEA, SPE A and TSST-1

Dodecamer antagonist peptide p12(150–161) elicits, in rabbits, antibodies that protect human T cells, capable of expressing IL-2 and IFN-γ genes, from activation not only by SEB but also by SEA and TSST-1. This finding indicates that used as vaccine, the peptide has the potential to confer broad-spectrum protective immunity.

Antibodies raised against a SEB-related peptide might bind to a pyrogenic exotoxin, for example SEB and modulate its action. To allow study of their immunogenicity and ability to elicit protective immunity against pyrogenic exotoxins, most peptides were synthesized also with an added N-terminal lauryl-Cys or C-terminal Cys (Table 2), to permit their linkage to proteosomes or KLH adjuvant, respectively [as described by Lowell et al. (1996) ibid.], in order to facilitate generation of antibodies. In addition, alum may be used as an immunization adjuvant directly with non-linked peptide, or after linking a peptide to proteosomes or to KLH [Lowell et al. (1996) ibid.].

Sera from rabbits immunized with individual peptides were titrated for their ability to bind SEB. Most of the peptides in Table 2 proved immunogenic by this parameter but greatly differed in titer of serum anti-SEB IgG achieved. Thus, serum against pSEB(13–33)C had a titer of 102,400 while corresponding titers for pSEB(81–93), pSEBLC (41–61) and p12LC(150–161) were 50, 1,600 and 1,600, respectively (Table 3). On the basis of the results in Table 3, one would not select p12(150–161) for use as a peptide vaccine but instead, prefer to use pSEB(13–33)C.

Figure 13:
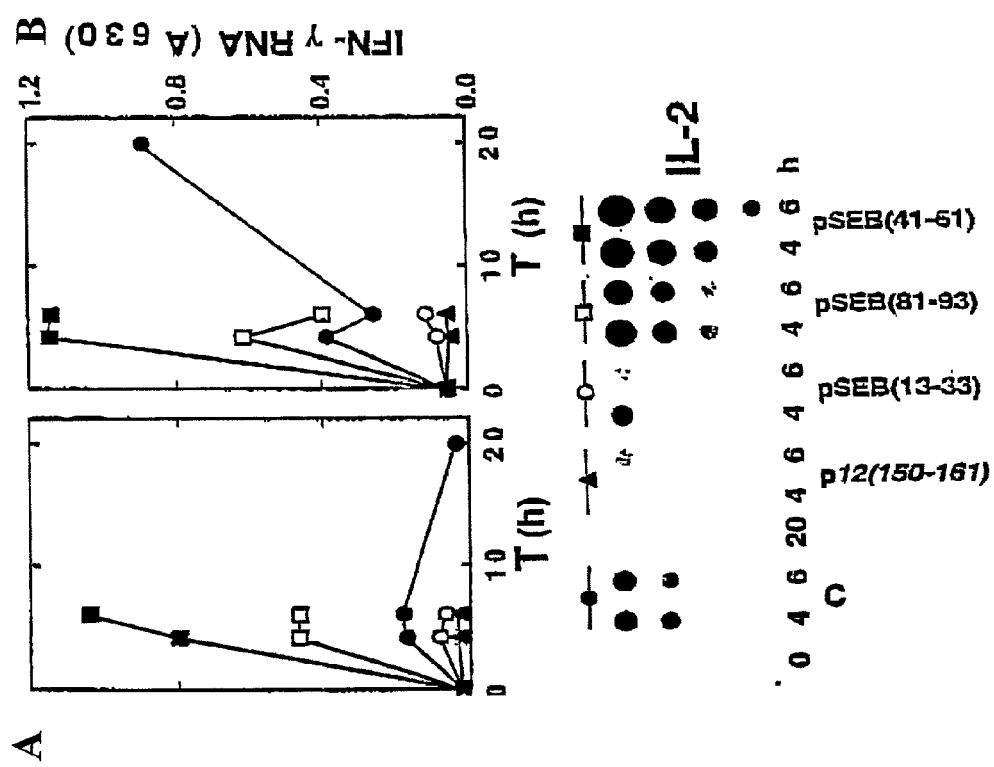
FIGS. 13A–13B show the effect of anti-SEB peptide sera on induction of IL-2 and IFN-γ mRNA by SEB. Aliquots of $4\times10^6$ PBMC were induced with SEB (control, C) (filled circles). Rabbit sera against SEB peptides p12LC(150–161) (filled triangles), pSEBLC(13–33) (open circles), pSEB (81–93) (open squares) or pSEB(41–61) (filled squares) in 1:100 dilution were included from the onset of induction. At times [T(h)] indicated, total RNA was extracted and serial twofold dilutions (vertical rows) were subjected to dot blot hybridization analysis with $^{32}$P-labeled IL-2 (FIG. 13A) and IFN-γ (FIG. 13B) anti-sense RNA probes. Only autoradiograms for IL-2 are shown. Autoradiograms were quantitated by densitometry at 630 nm (FIGS. 13A, 13B).

None of the antisera raised against individual SEB-related peptides had any SEB agonist activity, defined by ability to induce IL-2 or IFN-γ mRNA (not shown). Ability to inhibit SEB-mediated induction of these genes is examined in FIG. 13. Normal rabbit serum did not affect this induction (not shown). Consistent with its high titer of anti-SEB IgG, anti-pSEB(13–33)C serum partially inhibited induction of IL-2 and IFN-γ mRNA. However, despite its far lower titer, anti-p12LC(150–161) serum completely blocked the induction of both genes (FIGS. 13A and 13B).

Antisera against pSEB(81–93) and pSEBLC(41–61), which had low titers of anti-SEB IgG, not only failed to inhibit expression of IL-2 and IFN-γ mRNA but significantly stimulated their SEB-mediated induction (FIGS. 13A and 13B). This result was unexpected. This finding raises the possibility that elicitation of SEB-sensitizing antibodies, for example, by a toxoid [Lowell et al., Infect Immun 64:1706 (1996a); Lowell et al., Infect Immun 64: 4686 (1996b)] or mutant toxin vaccine [Stiles et al., Infect. Immun. 63:1229 (1995); Woody et al., Vaccine 15:133 (1997)], could lead, in a polyclonal antibody reaction, to exacerbation of toxic immune responses in SEB-exposed individuals. Antibodies raised against peptide p12(150–161), on the other hand, are free of exacerbating properties as measured in vitro, indicating that the peptide, or its derivatives, may serve as safer anti-toxin vaccine.

There was a striking lack of correlation between the ability of anti-peptide sera to bind SEB and to block SEB action. Antisera against pSEBLC(41–61) and p12LC (150–161) showed identical anti-SEB IgG titers yet affected induction of IL-2 and IFN-γ genes by SEB in an opposite manner, stimulation vs. complete inhibition. Apparently, certain antibodies effectively potentiate SEB action while others block it. As judged by serial dilution, inhibition of SEB-mediated gene induction was also up to 30-fold more sensitive for detecting blocking antibodies than binding of IgG to SEB.

In an earlier study, rabbit sera raised against SEB peptides 113–144, 130–160, 151–180 and 171–200 each reduced SEB-induced lymphocyte proliferation weakly ($\leq$2.5-fold), apparently in a nonspecific manner [Jett et al. (1994) ibid.].

Antibodies against p12(150–161) have broad-spectrum toxin blocking activity. In FIGS. 14A and 14B, SEA was used as inducer. Again, sera raised against p12LC(150–161) and pSEB(13–33)C strongly inhibited IL-2 and IFN-γ gene expression. As for SEB (FIG. 13A), sera raised against pSEB(81–93) or pSEBLC(41–61) failed to inhibit but instead, stimulated induction of IL-2 mRNA by up to 7-fold over the SEA control. Antiserum against pSEB(81–93) also stimulated expression of IFN-γ mRNA.

Antibodies raised against p12(150–161) and pSEB (21–33)C likewise inhibited the action of the even less related toxin, TSST-1 (FIG. 15A). Furthermore, antibodies raised against p12(150–161) inhibited the action of the streptococcal toxin, SPE A (FIG. 15B).

Figure 14:
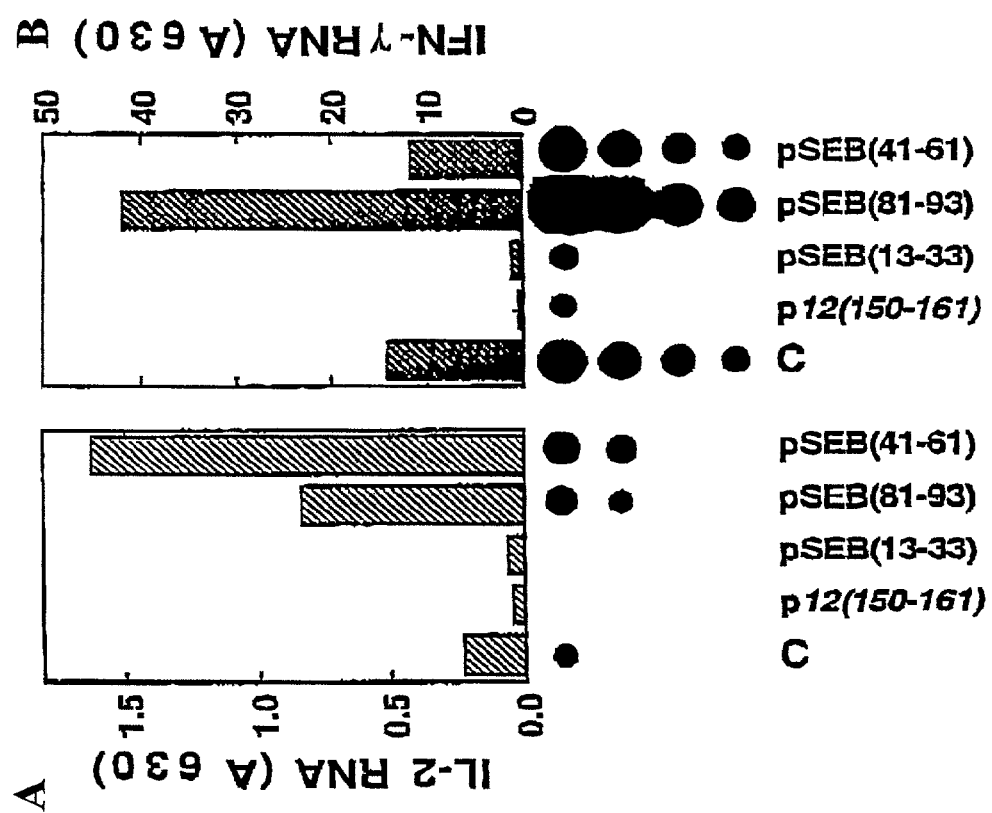
FIGS. 14A–14B show the effect of anti-SEB peptide sera on induction of IL-2 and IFN-γ mRNA by SEA. Aliquots of $4\times10^6$ PBMC were induced with SEA (control, C). Where shown, rabbit sera against SEB peptides p12LC(150–161), pSEBLC(13–33), pSEB(81–93) or pSEB(41–61) in 1:100 dilution were included from the onset of induction. At 6 hrs (FIG. 14A) and 20 hrs (FIG. 14B), total RNA was extracted and serial twofold dilutions (vertical rows) were subjected to dot blot hybridization analysis with $^{32}$P-labeled IL-2 (FIG. 14A) and IFN-γ (FIG. 14B) anti-sense RNA probes; autoradiograms shown were quantitated by densitometry at 630 nm.
Figure 15:
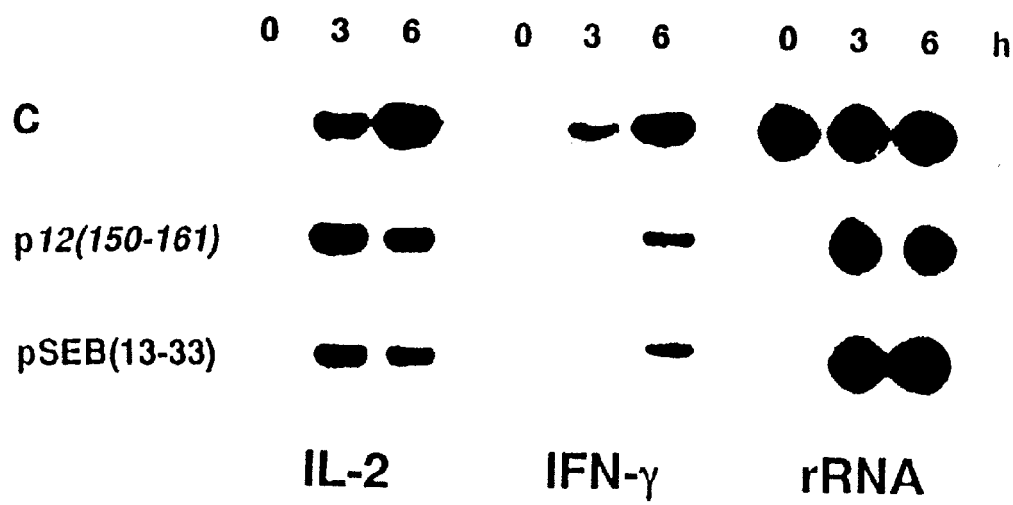
FIGS. 15A–15B show the effect of anti-SEB peptide sera on induction of IL-2 and IFN-γ mRNA by TSST-1, SEB, SPE A or SEA Aliquots of $3\times10^7$ PBMC were induced with 100 ng/ml of TSST-1 (control, (C)) (FIG. 15A). Where shown, rabbit sera against SEB peptides p12LC(150–161) or pSEBLC(13–33) in 1:10$^4$ dilution were included from the onset of induction. At times shown, total RNA was extracted and subjected to RNase protection analysis, using $^{32}$P-labeled IL-2 and IFN-γ antisense RNA probes as for FIG. 1D. rRNA served as loading control. In addition, aliquots of $3\times10^7$ PBMC were induced with 100 ng/ml of SEB, SPE A or SEA (control, (C)) (FIG. 15B). Where shown, rabbit serum against SEB peptide p12LC(150–161) in 1:10$^4$ dilution was included from the onset of induction. At times shown, total RNA was extracted and subjected to RNase protection analysis, using $^{32}$P-labeled IL-2 and IFN-γ antisense RNA probes as for FIG. 1D; for SEA, only the IL-2 probe was used.
Figure 15:
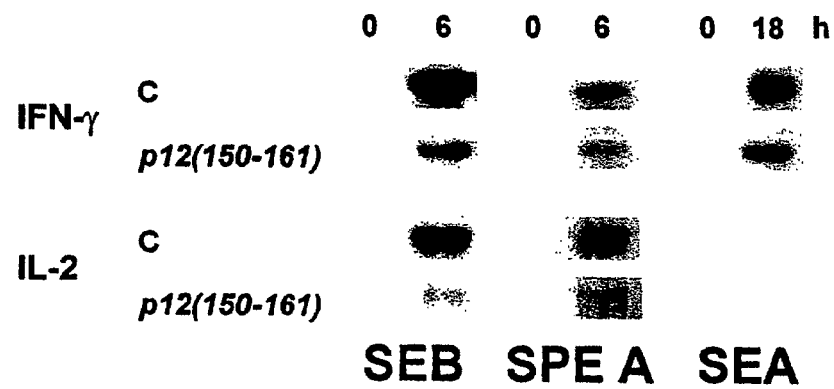

Hence, as judged from inhibition of IL-2 and/or IFN-γ gene expression analysis, protective activity of antibodies elicited by p12(150–161) is not narrowly restricted in range of pyrogenic exotoxins (FIGS. 13–15). These results suggest that p12(150–161) is potentially a broad-spectrum peptide vaccine against pyrogenic exotoxins.

TABLE 3

Anti-SEB antibody titers in sera from rabbits immunized with SEB-related peptides

| SEB Peptide | SEB IgG Titer |
| --- | --- |
| pSEBLC(13–24) | 800 |
| pSEBLC(13–33) | 800 |
| pSEBLC(21–33) | 100 |
| pSEBLC(41–61) | 1,600 |
| pSEBLC(53–61) | 1,600 |
| pSEBLC(81–92) | 1,600 |
| p12LC(150–161) | 1,600 |
| pSEBLC(208–218) | 1,600 |
| pSEB(13–33)C | 102,400 |
| pSEB(21–33)C | 25,600 |
| pSEB(41–61)C | 200 |
| pSEB(51–61)C | 400 |
| pSEB(81–93) | 50 |
| pSEB(208–218)C | 200 |

See Table 2 for explanation of SEB peptides. For immunization, peptides carrying LC at their N-terminus were coupled to proteosomes; peptides carrying C at their C-terminus were coupled to KLH. Sera were assayed for IgG able to bind SEB.

Example 8

Protective Effect of SEB-Related Peptides as SEB Vaccine in Mice

The finding that antiserum against p12(150–161) blocks the action of SEB in human PBMC suggested its potential as peptide vaccine. To examine this point, the D-galactosamine-treated mouse model was used [Lowell et al. (1996a) ibid.]. Mice were repeatedly immunized with individual peptides and then challenged with a lethal dose of SEB. Table 4 details the results of 3 separate trials.

In the first, formalin-inactivated intact SEB toxoid protected 20% of the mice against a lethal dose of SEB, either upon parenteral (i.m.) or intranasal vaccination. The fact that SEB toxoid did not afford complete protection as reported [Lowell et al. (1996a) ibid.] shows that the conditions of toxin challenge were more severe in the present experiment. In this trial, proteosome-coupled p12(150–161) yielded 10% protection. Relative to SEB toxoid, p12(150–161) thus did show protective activity.

In the second trial, the ability of proteosome-coupled pSEB(150–161) and p12(150–161) to provide immune protection against SEB challenge was compared to that of several larger, synthetic peptides [Jett et al. (1994)] derived from the SEB amino acid sequence, including pSEB (130–160) which overlaps almost completely with pSEB (150–161) and p12(150–161). None of the larger peptides showed detectable protective activity 1 against intranasal challenge with SEB, yet both pSEB(150–161) and p12 (150–161) afforded protection, evident from 22–29% survival (Table 4). pSEB(150–161) also elicited protective immunity (22%) when vaccination was by the intramuscular route (trial 3) rather than intranasally (trial 2). By contrast, two larger peptides, pSEB(130–160) and pSEB(151–180) that overlap in part with pSEB(150–161), failed to give protection. Moreover, peptide pSEB(13–33)C, though able to elicit in rabbits a high titer of IgG that inhibit the action of SEB, SEA and TSST-1 on human T cells, capable of expressing IL-2 and IFN-γ genes, in vitro (Table 3 and FIGS. 13–15), was not protective in mice.

Despite the severity of challenge with SEB toxin in these early trials, two SEB-related peptides exhibiting SEB antagonist activity, pSEB(150–161) and p12(150–161), also showed activity as SEB vaccine. Protective effect of SEB-related peptides tended to correlate with SEB antagonist activity on human PBMC in vitro (FIGS. 4–6) rather than with the ability to elicit SEB-binding IgG (Table 3). In trials 2 and 3, murine SEB-binding IgG titers were 50–200 for all peptides and did not correlate with protection (Table 4). Significantly, peptide pSEB(13–33)C, though able to elicit in rabbits a high titer of IgG that bind SEB and inhibit SEB action on PBMC in vitro (Table 3 and FIG. 13, was neither active as SEB antagonist (FIG. 4) nor protective in mice (Trial 3).

These examples show that it is possible to design an effective pyrogenic exotoxin antagonist. It is surprising that a linear, unstructured dodecapeptide, such as p12(150–161) or pSEB(150–161), can compete effectively with the intact, folded 239-amino acid SEB protein chain which interacts at multiple domains with regions in the MHC Class II molecule and in the T cell receptor. Such concerted interaction would lead to far higher affinity of binding for intact SEB vis-a-vis the peptides. Yet, as shown clearly in FIGS. 4–6, the action of SEB on human PBMC can be neutralized almost completely by the dodecapeptides, especially by p12(150–161). This first-generation antagonist, moreover, elicited in rabbits the production of antibodies that block the action of SEB on human T cells.

Subtle changes in peptide composition had marked effects on its SEB antagonist activity (FIGS. 4–6), indicating that substantial improvement is possible by methods known to a man of the art. In principle, significantly enhanced pyrogenic exotoxin antagonist activity can be obtained by generating dimers or multimeric forms (as shown in FIG. 7) or by constraining conformation, by use of disulfide bridges (as shown in FIG. 8), by internal bridges, short-range cyclizations or other means. In principle, improvement of the stability of the described peptides by these means will also render them more effective as peptide vaccine against pyrogenic toxins.

For example, the amino acid sequence of these dodecapeptides could also be extended stepwise at their N- or C-termini, or both, either with the natural SEB amino acid sequence, or with a D-amino acid that will tend to render the peptide less amenable to digestion by L-amino-acid-specific proteases (as shown for D-Ala in FIGS. 11 and 12) or with aromatic residues such as Trp to enhance the hydrophobicity of the resulting peptide, or with a random sequence of amino acids followed by selection using existing methods, for example, phage display, in order to obtain peptide(s) with enhanced antagonist activity and/or immunoprotective properties. Immunogenicity may be enhanced, for example, by use of in vitro reconstituted MHC/peptide complex as described by Sakita et al. [Sakita et al., J. Immunol. Methods 192:105 (1996)].

There are few examples of short peptides able to bind with sufficiently high affinity to a receptor in order to mimic the binding of the full-length ligand or to block its action. A T-cell receptor antagonist peptide of 4 amino acids was able to inhibit clinical disease progression in experimental allergic encephalomyelitis mediated by a diverse T cell repertoire [Kuchroo et al., J. Immunol. 153:3326 (1994)]. Peptides derived from the predicted helical region of MHC class II molecules may interact directly with T cell receptors: one such a peptide, a 16-mer, appeared capable of modulating immune responses in a physiologically significant manner [Williams et al., Immunol Res 11:11, (1992)]. In another example, a synthetic, 22-amino-acid segment of the human IFN-γ receptor was found to antagonize the action of IFN-γ [Seelig et al., J Biol Chem 270:9241 (1995)]. The linear forms of peptides generally lack a stable conformation in solution. Interaction with the cognate binding site on a receptor may induce folding of the peptide to mimic conformation in the native protein. Significant improvement in binding affinity can be achieved by generating dimers or multimeric forms of the peptide (FIG. 7) or by constraining conformation, for example, through cyclization (FIG. 8). Thus, by dimerizing bioactive peptides based on an antibody hypervariable region sequence, higher affinity binding was produced; an optimized cyclic peptide showed up to 40-fold enhanced affinity when compared to the linear form [Williams et al., J Biol Chem 266:5182, (1991)]. A hexapeptide, once cyclized by oxidizing a Cys-hexapeptide-Cys form, showed a higher avidity for the collagen receptor than the more flexible linear structure [Cardarelli et al., J Biol Chem 267:23159 (1992)]. A synthetic 15-amino-acid peptide mimic of plasma apolipoprotein E failed to bind to the low density lipoprotein receptor but its dimeric form was active in binding; a trimer, moreover, had 20-fold greater activity than the dimer [Dyer and Curtiss, J Biol Chem 266:22803 (1991)]. In addition to affecting peptide conformation and thus enhancing its binding affinity and/or immunogenicity, multimerization or cyclization of a peptide may also enhance its biostability, thus enhancing its efficacy as vaccine. These examples provide to a man of the art methods to improve upon the antagonist activity of SEB-related peptides as detailed in this invention and through this criterion, potential vaccine efficacy.

Methods for generating multimeric or cyclic forms of peptides exist, as by direct synthesis (FIG. 7). Another approach is to generate two terminal Cys residues as described above [Cardarelli et al. (1992) ibid.]; their oxidation will yield both cyclic and multimeric forms, mostly dimers (FIG. 8). An efficient procedure for the preparation of protected cyclized and protected symmetrical dimeric pep tide disulfides by oxidative detachment from a support has been described [Rietman et al., Int J Pept Protein Res 44:199 (1994)]. Fully cyclic forms of peptides will lack free termini but cyclic peptides can be made by internal bridges, or short-range cyclizations [Toniolo, Int J Peptide Protein Res 35:287 (1990); Gilon et al., Biopolymers 31:745 (1991)] to allow synthesis of LC- or -C termini.

The experimental approach employed here used expression of human cytokine genes in vitro as a tool for designing both a broad-spectrum pyrogenic toxin antagonist and a prototypical peptide vaccine. This molecular approach is far more rapid than conventional methods that are based solely on animal tests, allowing evaluation of the biological properties of a candidate peptide well before moving on to animal studies for analysis of vaccine efficacy, prophylactic and therapeutic activity. Specifically, analysis of pyrogenic toxin antagonist activity on human T cells can be used to direct effective vaccine development, even before ability to elicit antibodies is studied in animals.

Efficacy of potential vaccine candidates can be evaluated not only by their pyrogenic toxin antagonist activity but also by their ability to elicit production of antibodies in rabbits (shown for SEB in Table 3) that can block the harmful action of pyrogenic exotoxins on human lymphoid cells (FIGS. 13–15), independently of their ability to bind toxin. The examples show that assay of the ability of anti-peptide antibodies to block the action of SEB on human cytokine gene expression is far more sensitive than assay of the ability to bind SEB (Table 3 and FIGS. 13 and 14. At least certain antisera showing very high anti-SEB IgG titers (Table 3) are not necessarily protective against the toxin. This result casts doubt on the relevance of IgG assays for evaluating or predicting immunoprotection against SEB, as also shown in Table 4, trials 2 and 3.

In order to vaccinate humans effectively against one or more pyrogenic toxins, there in a need to assess the efficacy of vaccination. This requirement is independent of the nature of the vaccine, whether a toxoid, a mutant toxin or a peptide. However, unlike experimental animals (Table 4), humans cannot be challenged with toxin to test if the vaccination was effective. Therefore, it is desirable to use a surrogate marker instead, preferably one based on human T cell activation. Such a marker is provided through the method used in FIGS. 13–15, which measures the ability of serum from an immunized individual to antagonize toxin-mediated activation of human T cells. Given the fact that humans are far more sensitive than mice to staphylococcal toxins, use of human T cells as shown in FIGS. 13 to 15 has advantages over use of murine cells [Stiles et al., Infect Immun 63:1229 (1995)]. Toxin-mediated activation of T cells is preferably measured by the induction of IL-2, IFN-γ or TNF-β gene expression, which yields information on the response of these genes within a few hours after their induction, long before any effect on cell proliferation.

SEB-related peptides with demonstrated SEB antagonist activity, p12(150–161) and pSEB(150–161), carry sequence elements that are highly conserved amongst pyrogenic toxins. Through improved peptide design, including introduction of structural constraints, peptides may thus be generated that exhibit broader antagonist activity (FIGS. 11, 12). A peptide antagonist able to protect against a range of related enterotoxins would be far more valuable than a narrowly active one.

Rabbit sera raised against p12(150–161) were equally able to block the ability of SEB, SEA, SPE A or TSST-1 to induce expression of IL-2 and IFN-γ genes (FIGS. 13–15) These results show a potential for broader protective immunity. A peptide vaccine able to impart protective immunity against a range of related enterotoxins would be far more valuable than a narrowly active one.

An unexpected finding, shown in FIGS. 13 and 14, is that antisera against certain SEB peptides not only fail to block the action of SEB on human lymphoid cells, but actually stimulate it significantly. This result should alert one to the possibility that vaccination with such peptide domains, including those present in SEB toxoid or other derivatives of the SEB toxin molecule, could sensitize an exposed person to the lethal effects of SEB and other pyrogenic exotoxins, for example SEA, rather than protect him.

TABLE 4

Protective Effect of SEB Peptides in Mice

| Trial | Vaccine | No. of Animals | Vaccine Route | Challenge Route | Challenge (μg SEB) | IgG Titer | Percent Survival |
|---|---|---|---|---|---|---|---|
| 1 | p12LC(150–161) | 10 | IM | IM | 25 | | 10 |
| | p12LC(150–161) | 10 | IN | IM | 25 | | 10 |
| | SEB Toxoid | 10 | IM | IM | 25 | | 20 |
| | SEB Toxoid | 10 | IN | IM | 25 | | 20 |
| 2 | PSEBLC (150–161) | 7 | IN | IN | 350 | 200 | 29 |
| | p12LC(150–161) | 9 | IN | IN | 350 | 200 | 22 |
| | pSEBLC(93–112) | 9 | IN | IN | 350 | 200 | 0 |
| | pSEBLC (130–160) | 9 | IN | IN | 350 | 200 | 0 |
| | pSEBLC (191–220) | 9 | IN | IN | 350 | 200 | 0 |
| | pSEB(191–220)C | 9 | IN | IN | 350 | 50 | 0 |
| | Control | 5 | IN | IN | 350 | 100 | 0 |
| 3 | pSEBLC (150–161) | 9 | IM | IN | 350 | 200 | 22 |
| | pSEB(13–33)C | 9 | IM | IN | 350 | 100 | 0 |
| | pSEBLC (93–112) | 9 | IM | IN | 350 | 200 | 0 |
| | pSEBLC (130–160) | 9 | IM | IN | 350 | 100 | 0 |
| | pSEBLC (151–180) | 9 | IM | IN | 350 | 200 | 0 |
| | pSEBLC (191–220) | 9 | IM | IN | 350 | 200 | 0 |
| | pSEB(191–220)C | 9 | IM | IN | 350 | 50 | 0 |

Groups of mice were vaccinated with SEB-related peptides or SEB toxoid as indicated. SEB toxoid [Lowell et al., (1996) ibid.], peptides pSEB(93–112), pSEB(130–160), pSEB(151–180), pSEB(191–220) and pSEB(191–220)C [Jett et al., (1994) ibid.] and preparation of LC-derivatives for coupling to proteosomes [Lowell et al., (1996) ibid.], were described elsewhere. In trial 1, 2 vaccinations were given 2 weeks apart, with SEB challenge after 1 month. In trials 2 and 3, 3 vaccinations were given at 2-week intervals, followed by a boost after 6 weeks and SEB challenge 2 weeks later. IgG were determined 3 weeks before challenge. IM, intramuscular; IN, intranasal.

Table 5 lists for each of the SEQ ID NOS of the sequence listing, the corresponding alternative notation used in the specification.

TABLE 5

Identification of SEB Related Peptides by Their SEQ ID Numbers

Figure 16:
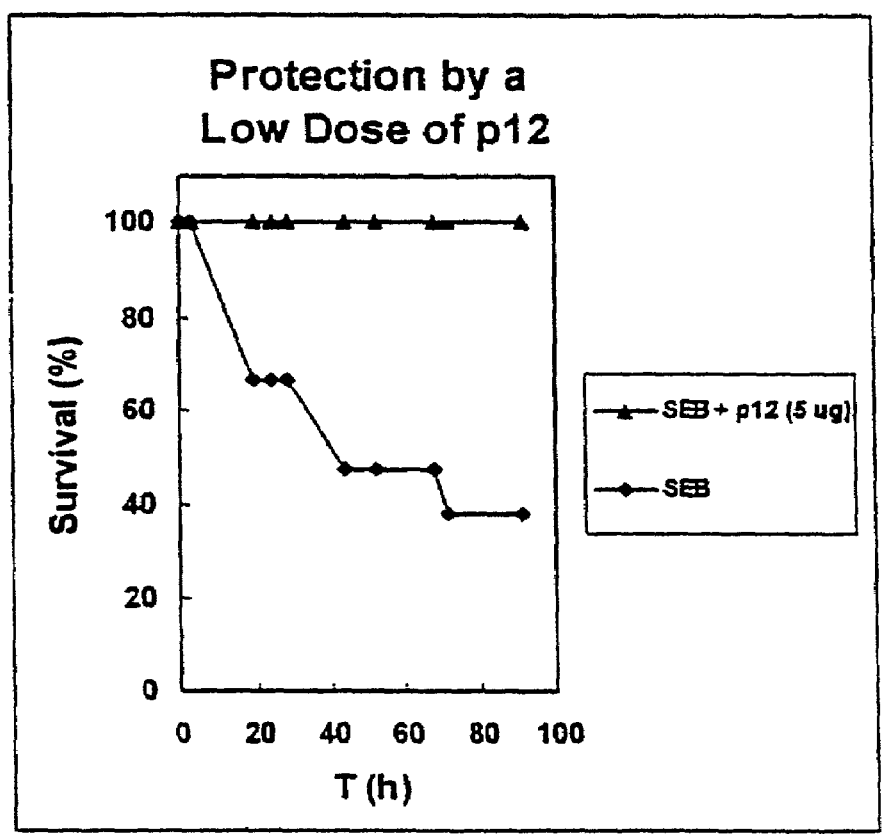
FIG. 16 shows protection of mice from the lethal effect of a low dose of SEB by p12(150–161) carrying a D-Ala residue at both N- and C-termini. Groups of 10 mice each (9–10 week BALB/C females) were injected intraperitoneally with 20 mg per mouse of D-galactosamine. Two hours later, one group (filled triangles) received 5 μg per mouse of p12(150–161) carrying a D-Ala residue at both N- and C-termini (p12), by intravenous injection. Thirty minutes later, each mouse received 20 μg of SEB by intraperitoneal administration. Survival in each group was determined thereafter, at the times in hours indicated. Surviving animals showed no signs of malaise and were indistinguishable from normal controls in behavior; they survived for as long as monitored, two weeks.
Figure 17:
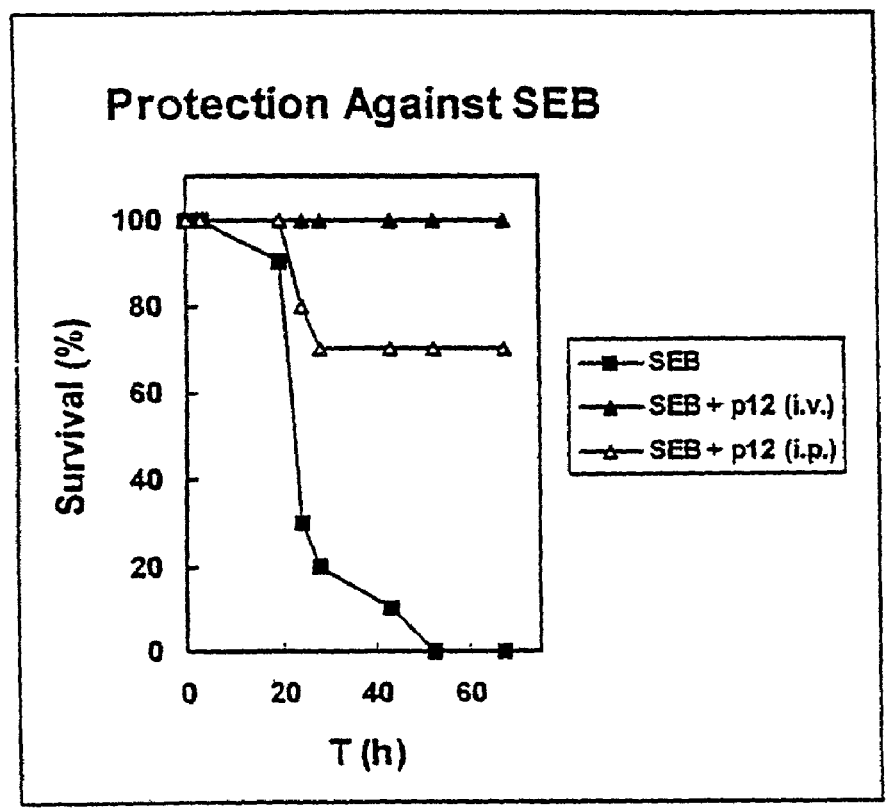
FIG. 17 shows protection of mice from the lethal effect of SEB by p12(150–161) carrying a D-Ala residue at both N- and C-termini. Groups of 10 mice each (9–10 week BALB/C females) were injected intraperitoneally with 20 mg per mouse of D-galactosamine. Two hours later, 25 μg per mouse of p12 (see FIG. 16) were administered to one group by intravenous injection (filled triangles) and to a second group by intraperitoneal administration (open triangles). Control group mice did not receive peptide (filled square). Thirty minutes later, each mouse received 20 μg of SEB by intraperitoneal administration. Survival in each group was determined thereafter, at the times in hours indicated. Surviving animals showed no signs of malaise and were indistinguishable from normal controls in behavior; they survived for as long as monitored, two weeks.
Figure 18:
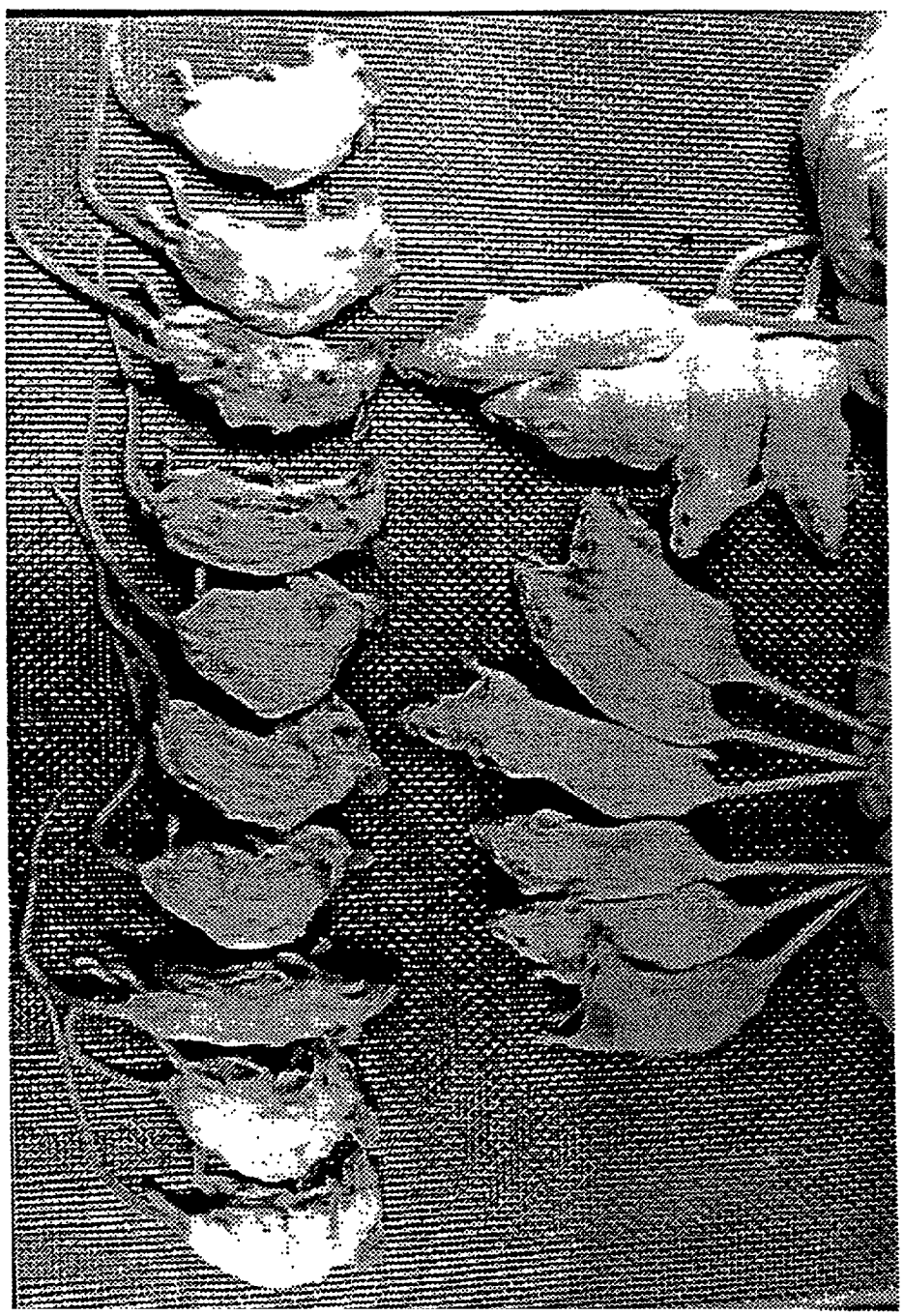
FIG. 18 shows protection of mice from the lethal effect of SEB by p12(150–161) carrying a D-Ala residue at both N- and C-termini. Photograph of two groups of 10 mice from the experiment of FIG. 17, taken two weeks after challenge with SEB. Top group: mice that received 25 μg of p12 (see FIG. 16) by intravenous injection before challenge with SEB. Bottom group: mice that did not receive peptide before challenge with SEB.

| SEQ ID NO: | Alternative Notatior | Sequence |
|---|---|---|
| SEQ ID No. 1 | pSEB(150–161) | T N K K K V T A Q E L D |
| SEQ ID No. 2 | p12(150–161) | Y N K K K A T V Q E L D |
| SEQ ID No. 3 | pSEB(152–161) | K K K V T A Q E L D |
| SEQ ID No. 4 | p10(152–161) | K K K A T V Q E L D |
| SEQ ID No. 5 | pSEBLC(150–161) | lcT N K K K V T A Q E L D |
| SEQ ID No. 6 | p12LC(150–161) | lcY N K K K A T V Q E L D |
| SEQ ID No. 7 | Dimer | Y N K K K A T V Q E L D Y N K K K A T V Q E L I |
| SEQ ID No. 8 | Trimer | Y N K K K A T V Q E L D Y N K K K A T V Q E L I<br>Y N K K K A T V Q E L D |
| SEQ ID No. 9 | Cys-p12(150–161) | C Y N K K K A T V Q E L D C |
| SEQ ID No. 10 | D-Ala | daY N K K K A T V Q E L Dda |
| SEQ ID No. 11 | Ac-p12(150–161) | acY N K K K A T V Q E L Dda |
| SEQ ID No. 12 | SEB | E S Q P D P K P D E L H K S S K F T G L M E N M<br>K V L Y D D N H V S A I N V K S I D Q F L Y F D I<br>I Y S I K D T K L G N Y D N V R V E F K N K D L<br>A D K Y K D K Y V D V F G A N Y Y Y Q C Y F S<br>K K T N D I N S H E T D K R K T C M Y G G V T E<br>H N G N Q L D K Y R S I T V R V F E D G K N L L<br>S F D V Q T N K K K V T A Q E L D Y L T R H Y L<br>V K N K K L Y E F N N S P Y E T G Y I K F I E N E<br>N S F W Y D M M P A P G D K F D Q S K Y L M M<br>Y N D N K M V D S K D V K I E V Y L T T K K K |
| SEQ ID No: 13 | p14 | V Q Y N K K K A T V Q E L D |
| SEQ ID No: 14 | p14A (D-Ala) | daV Q Y N K K K A T V Q E L Dda |
| SEQ ID No: 15 | p14-LP | lpV Q Y N K K K A T V Q E L D | lc, N-lauryl-cysteyl;
da, D-Ala;
ac, N-acetyl,
lp- N-lysyl-palmitoyl

Example 9

Protection and Rescue of Mice from Lethal Shock

Groups of 10 mice each (9–10 week BALB/C females) were injected intraperitoneally with 20 mg per mouse of D-galactosamine. Two hours later, one group received 5 μg per mouse of p12(150–161) carrying a D-Ala residue at both N- and C-termini, by intravenous injection. Thirty minutes later, each mouse received 20 μg of SEB by intraperitoneal administration. Survival in each group was determined thereafter, at the times in hours indicated in FIG. 16. Surviving animals showed no signs of malaise and were indistinguishable from normal controls in behavior; they survived for as long as monitored, two weeks.

Groups of 10 mice each (9–10 week BALB/C females) were injected intraperitoneally with 20 mg per mouse of D-galactosamine. Two hours later, 25 μg per mouse of p12(150–161) carrying a D-Ala residue at both N- and C-termini were administered to one group by intravenous injection and to a second group by intraperitoneal administration. Control group mice did not receive peptide. Thirty minutes later, each mouse received 20 μg of SEB by intraperitoneal administration. Survival in each group was determined thereafter, at the times in hours indicated in FIG. 17. Surviving animals showed no signs of malaise and were indistinguishable from normal controls in behavior; they survived for as long as monitored, two weeks.

Groups of 10 mice each (9–10 week BALB/C females) were injected intraperitoneally with 40 mg per mouse of D-galactosamine. Two hours later, 25 μg per mouse of p12(150–161) carrying a D-Ala residue at both N- and C-termini were administered by intravenous injection to each group except a control group of 20 mice. Thirty minutes later, each mouse received 5 μg of TSST-1 by intraperitoneal administration. An additional intravenous injection of 25 μg per mouse of the peptide were administered at 3 hr post-challenge or at 3 and 18 hr post-challenge. Survival in each group was determined thereafter, at the times in hours indicated in FIG. 19. Surviving animals showed no signs of malaise and were indistinguishable from normal controls in behavior; they survived for as long as monitored, two weeks.

While 100% of mice exposed to SEB lethal challenge died within 1–2 days in the control group, 100% survived lethal challenge with SEB when p12(150–161) carrying a D-Ala residue at both N- and C-termini was administered intravenously half an hour before challenge, and 70% when it was administered intraperitoneally (FIGS. 16–18). Surviving animals showed no signs of malaise and were indistinguishable from normal controls in behavior; they survived for as long as monitored, two weeks. No side effects of p12(150–161) carrying a D-Ala residue at both N- and C-termini could be detected.

Figure 19:
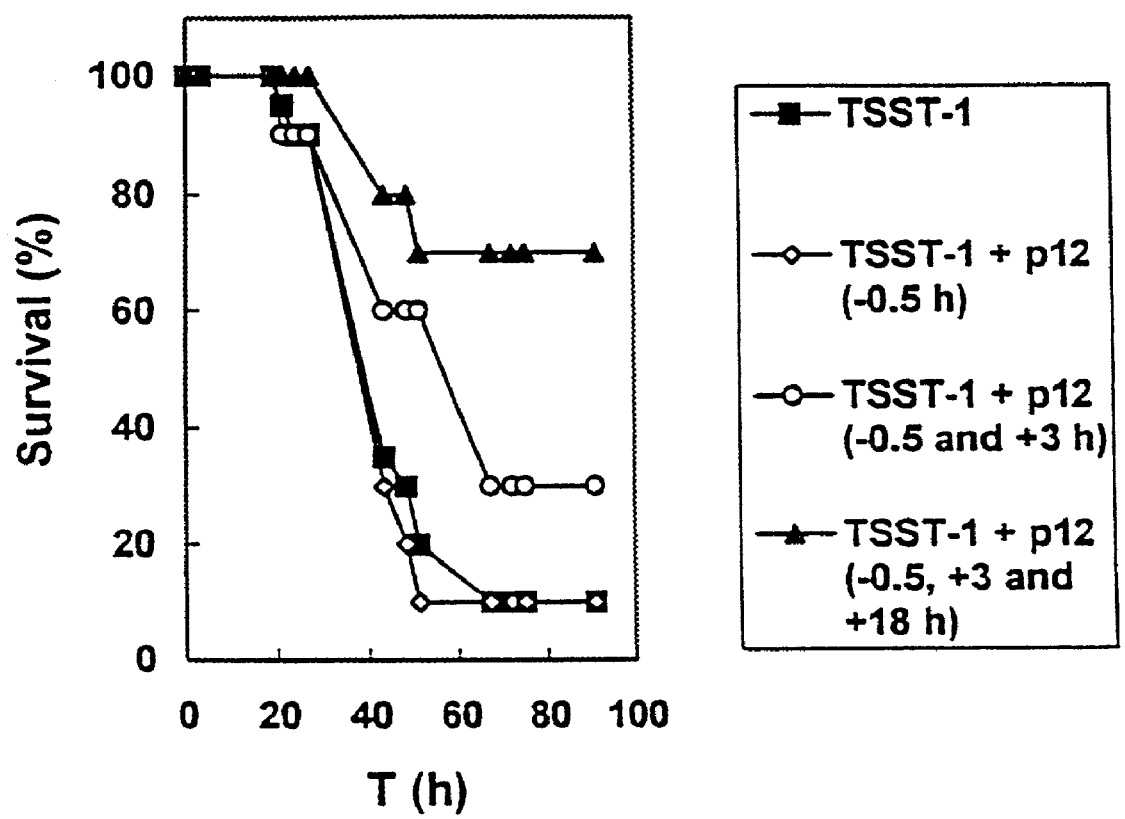
FIG. 19 shows protection of mice from the lethal effect of TSST-1 by p12(150–161) carrying a D-Ala residue at both N- and C-termini. Groups of 10 mice each (9–10 week BALB/C females) were injected intraperitoneally with 40 mg per mouse of D-galactosamine. Two hours later, 25 μg per mouse of p12 (see FIG. 16) were administered by intravenous injection to each group (open square, open circle, filled triangle) except a control group of 20 mice (filled square). Thirty minutes later, each mouse received 5 μg of TSST-1 by intraperitoneal administration. An additional intravenous injection of 25 μg per mouse of p12 was administered at 3 hr post-challenge (open circle) or at 3 and 18 hr post-challenge (filled triangle). Survival in each group was determined thereafter, at the times in hours indicated. Surviving animals showed no signs of malaise and were indistinguishable from normal controls in behavior; they survived for as long as monitored, two weeks.

To extend this result to other toxins and to demonstrate broad-spectrum protective activity of this peptide, lethal challenge with TSST-1 was tested. Within the superantigen toxin family, TSST-1 is most remote from SEB, showing only 6% amino acid homology for the whole toxin molecule. TSST-1 kills more slowly than SEB, requiring a longer toxin exposure (FIGS. 17 and 19). p12(150–161) carrying a D-Ala residue at both N- and C-termini did not protect against lethal challenge with TSST-1 when administered once, just before challenge, but it afforded significant protection upon repeated administration post-challenge (FIG. 19). The protective effect of p12(150–161) carrying a D-Ala residue at both N- and C-termini became more pronounced with increasing number of administrations (FIG. 19), showing that survival from TSST-1 challenge is dependent on sustained presence of the peptide.

The p12(150–161) peptide carrying D-Ala residues at both its N- and C-termini, which is SEB-related, afforded good antagonist activity not only against SEB intoxication, but also against the remotely homologous TSST-1. Thus, p12(150–161) peptide carrying D-Ala residues at both its N- and C-termini can be used as an effective broad-spectrum antagonist against pyrogenic exotoxins.

Example 10

Potent Protecting Activity of p14A on Lethally Challenged Mice

Figure 20:
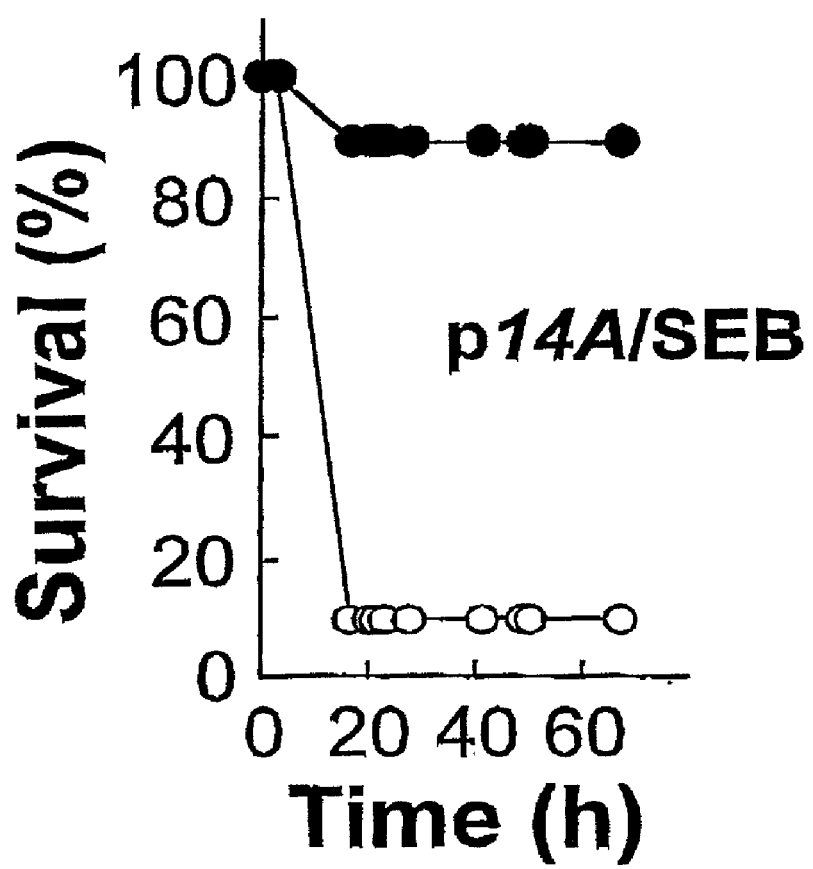
FIG. 20 shows that antagonist peptide protects mice from SEB-induced lethal shock. Ten Balb/c mice were sensitized with 20 mg D-galactosamine and challenged simultaneously with 10 μg SEB (open circles). Another 10 mice received 25 μg p14A 30 min before SEB challenge (filled circles). Survival was monitored.

In the experiment of FIG. 20, 90% of control mice were killed within less than 20 h when exposed to SEB. However, when p14A, which is a derivative of p14 carrying D-Ala residues at both its N- and C-termini, was administered just before lethal challenge with SEB, 90% of these mice survived (FIG. 20). A protective effect of p14A was observed reproducibly in over fifteen experiments. Surviving animals showed no signs of distress and remained indistinguishable from normal controls in behavior; they survived for as long as monitored, two weeks. Mice exposed to p14A alone stayed fully viable and showed no detectable side effects.

Example 11

Antagonist Peptide Protects and Rescues Mice from SEB-Induced Lethal Shock

Figure 21:
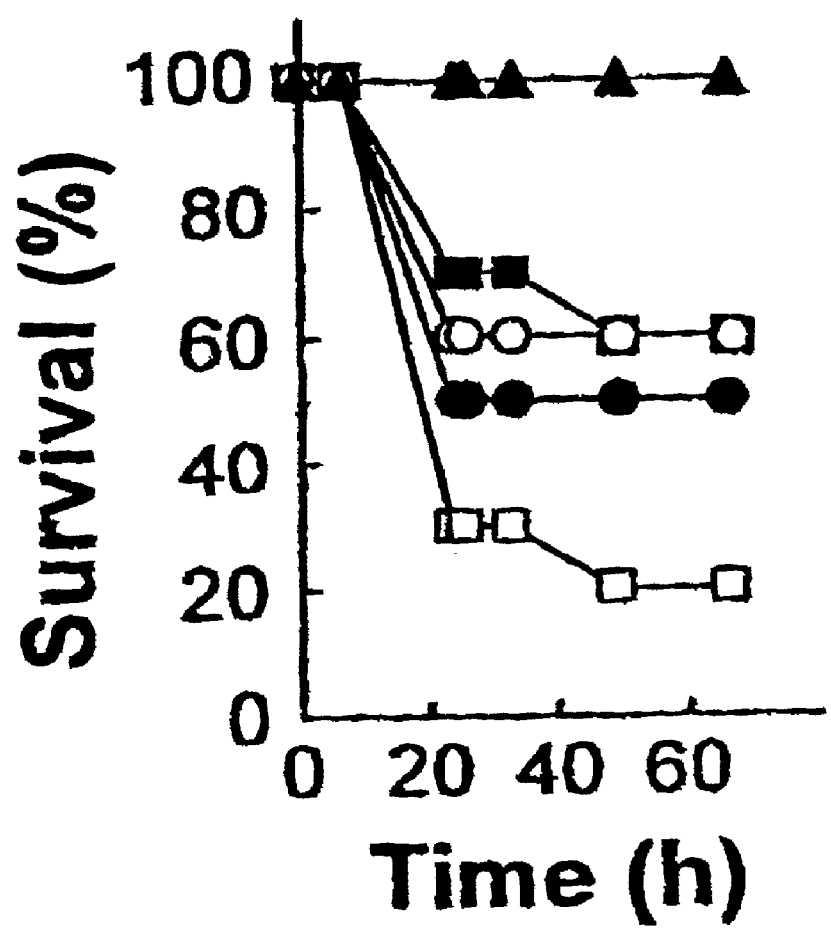
FIG. 21 shows that the antagonist peptide protects and rescues mice from SEB-induced lethal shock. Groups of 10 BALB/c mice were sensitized with 20 mg D-galactosamine and challenged simultaneously with 10 μg SEB, injected together. An aliquot of 25 μg p14A was injected at 30 min before SEB (filled triangle) or at 3 (filled squares), 5 (open circles), or 7 (filled circles) h after SEB. Ten sensitized, naive mice that did not receive p14A served as SEB controls (open squares). All injections were IP.

Mice exposed to antagonist peptide alone remained viable and showed no detectable side effects. Of the mice challenged with SEB, only 30% were still alive at 24 h after toxin exposure and 20% at later times. However, all of the SEB-challenged mice were protected by p14A given 30 min before toxin (p=0.0003). Surviving animals showed no signs of distress and remained indistinguishable from normal controls in behavior; they survived for as long as monitored, two weeks. Partial protection was obtained when administration of the antagonist peptide was delayed to 3 h (p=0.05), 5 h (p=0.08) or even 7 h after lethal challenge. A progressively decreasing protective effect of p14A was seen between 20 and 40 h, yielding 70%, 60% and 50% survival, respectively. Remarkably, p14A is not only fully protective when given before SEB challenge but able to rescue mice already deeply into toxic shock. These results are shown in FIG. 21.

Protection or rescue was observed when the antagonist peptide was in 20- to 40-fold molar-excess over SEB, showing that the peptide is a potent superantigen antagonist in vivo.

Example 12

Potent Protecting Activity of p14A on Lethally Challenged Mice

Figure 22:
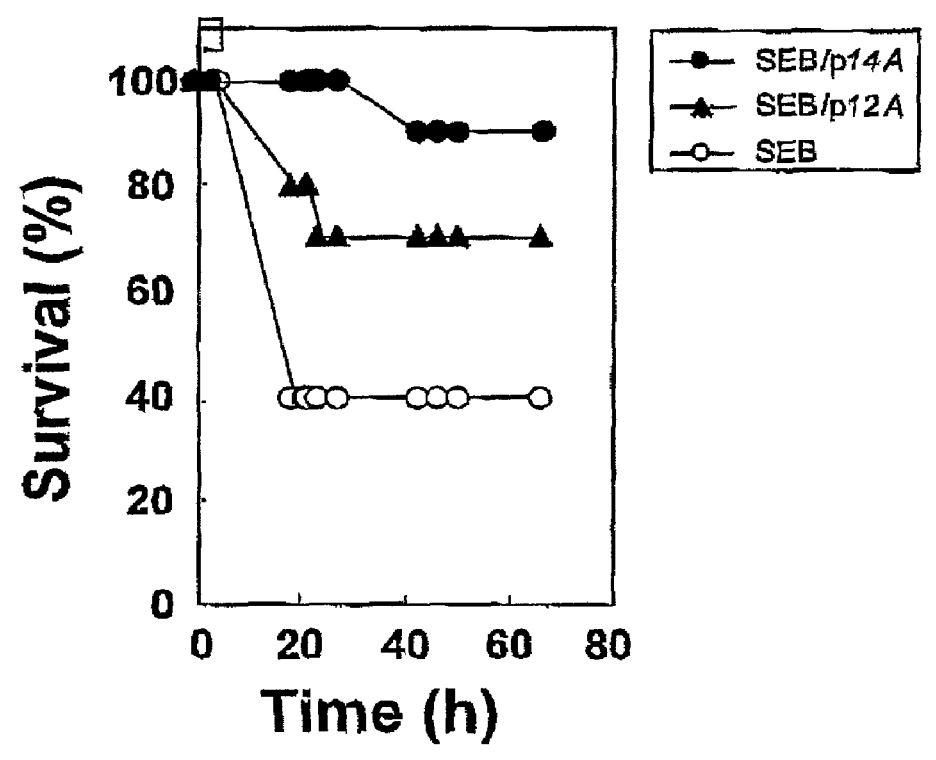

Using D-galactosamine-sensitized mice, an accepted animal model for studying lethality of the superantigens, the protective activity of p12A and p14A was investigated. FIG. 22 shows that when p14A was administered just before lethal challenge with SEB, about 90% of these mice survived after over 60 hours, in comparison to about 70% surviving mice treated with p12A, and only 40% of the untreated animals (no peptide administered). A protective effect of p14A was observed reproducibly in over 15 experiments. Surviving animals showed no signs of distress and remained indistinguishable from normal controls in behavior; they survived for as long as monitored, 2 weeks. Mice exposed to p14A or p12A alone stayed fully viable and showed no detectable side effects.

Example 13

Potent Antagonistic Activity of p14A on Induction of IFN-γ Gene Expression

Figure 23:
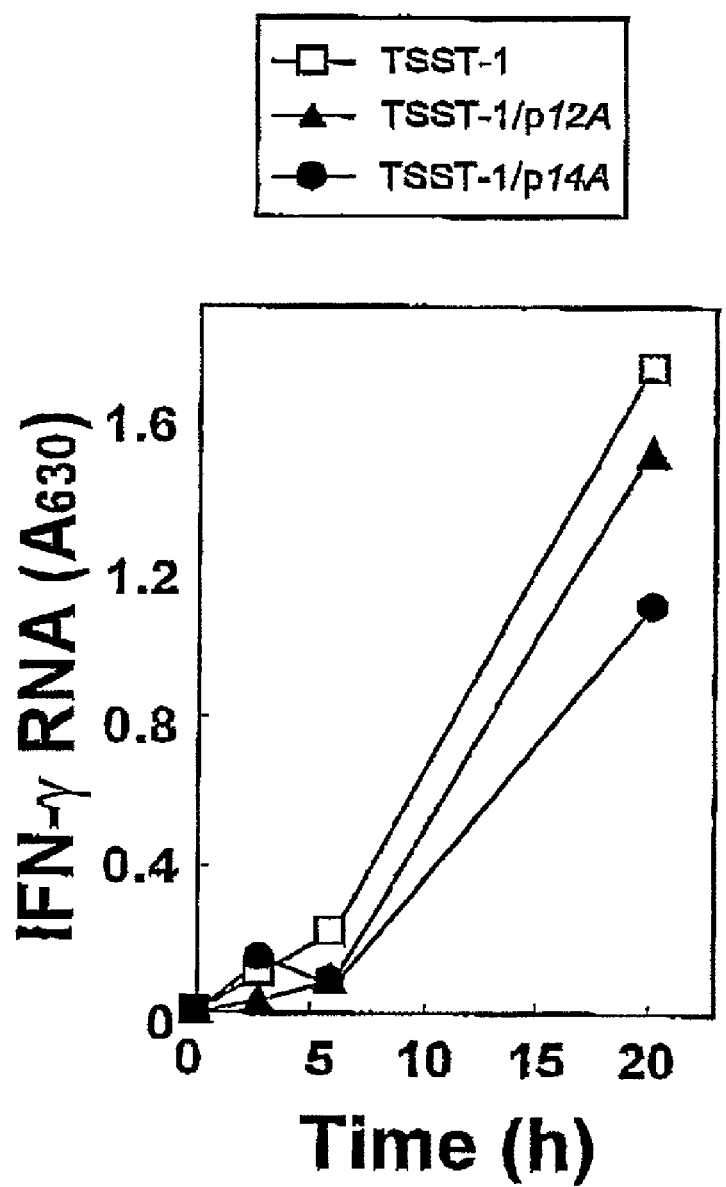
FIG. 23 shows the effect of antagonist peptides p12A and p14A on the induction of IFN-γ gene expression by TSST-1. PBMC from healthy human donors were separated on Ficoll Paque (Pharmacia), washed twice with 50 ml of RPMI 1640 medium, resuspended at a density of $4 \times 10^6$/ml and cultured in this medium supplemented with 2% fetal calf serum, 2 mM glutamine, 10 mM MEM nonspecific amino acids, 100 mM Na-pyruvate, 10 mM Hepes, pH 7.2, $5 \times 10^{-5}$ M 2-ME, 100 units/ml penicillin, 100 μg/ml streptomycin and 5 μg/ml nystatin. After overnight resting, aliquots of $4 \times 10^6$ PBMC in 1 ml were cultured for the times indicated in the presence of 100 ng/ml of TSST-1 (Sigma) alone or in the presence of 10 μg/ml of p12A or p14A as indicated. Total RNA was extracted at times shown and serial twofold dilutions were subjected to blot hybridization analysis with $^{32}$P-labeled IFN-γ antisense RNA probe [as described in the Examples (Materials and Methods)]. The autoradiogram was quantitated by densitometry at 630 nm and absorbency at 630 nm is plotted.
Figure 24:
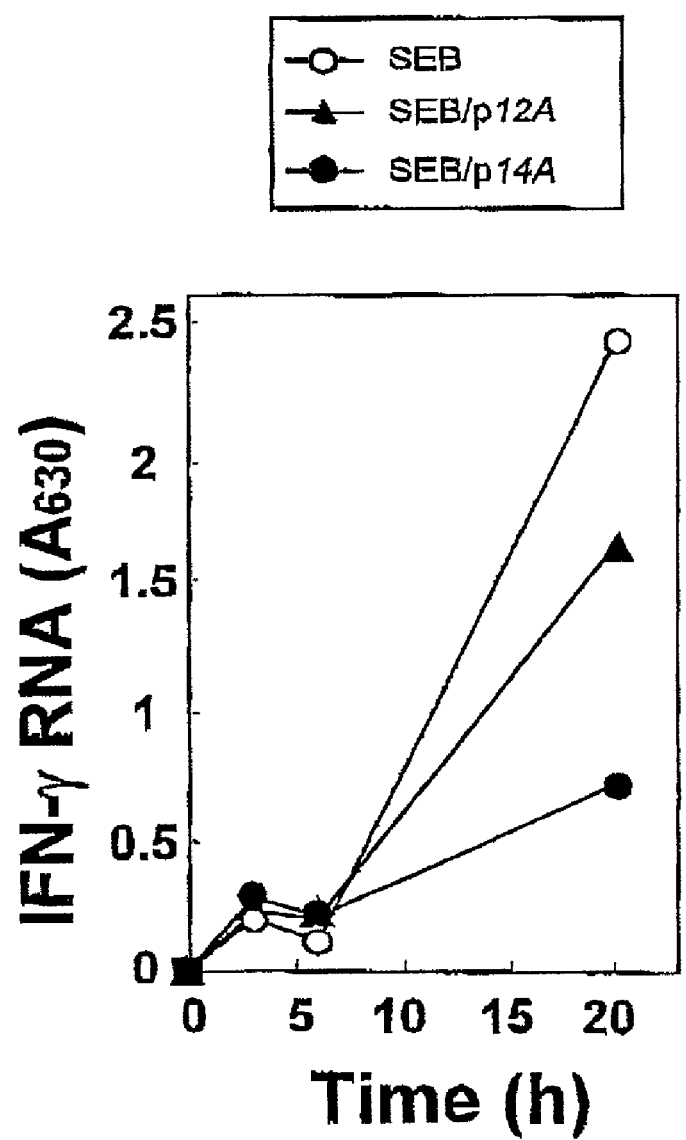
FIG. 24 shows the effect of antagonist peptides p12A and p14A on the induction of IFN-γ gene expression by SEB. Aliquots of $4 \times 10^6$ PBMC in 1 ml were cultured for the times indicated in the presence of 100 ng/ml of SEB lot 14–30, from the Department of Toxicology, United States Army Medical Research Institute of Infectious Diseases (USAMRIID, Frederick, Md.) alone or in the presence of 10 μg/ml of p12A or p14A as indicated. Total RNA was extracted at times shown and serial twofold dilutions were subjected to blot hybridization analysis with $^{32}$P-labeled IFN-γ antisense RNA probe. The autoradiogram was quantitated by densitometry at 630 nm and absorbency at 630 nm is plotted. The same PBMC population was used as for FIG. 23.

The effect of p14A and p12A (SEQ ID NO:14 and SEQ ID NO:10, respectively) on the extent of induction of IFN-γ by TSST-1 or SEB in PBMC populations was compared, and the results are shown in FIGS. 23 and 24.

Although TSST-1 exhibits a mere 6% homology with the overall sequence of SEB, both p12A and p14A inhibited IFN-γ expression induced by this toxin (TSST-1, FIG. 23). Both p12A and p14A also inhibited the expression induced by SEB (FIG. 24). Surprisingly, p14A exhibited remarkably more potent antagonistic activity than p12A, whether against TSST-1 or SEB.

p12A and p14A share very little homology with the corresponding domain in TSST-1. Nonetheless, both peptides inhibited TSST-1-induced expression of IFN-γ, and also here p14A was unexpectedly more efficient, despite the fact that it shares only 4/14 amino acid residues with the corresponding domain in TSST-1, as compared to 4/12 for p12A.

Example 14

Protected Mice Rapidly Develop Broad-Spectrum Resistance to Lethal Shock

To examine whether the antagonist peptide exhibits broad-spectrum, protective activity, the inventors studied its effect during lethal challenge with SEA, a superantigen showing only 27% overall amino-acid sequence homology with SEB [Betley and Mekalanos 1988. J. Bacteriol. 170: 34–41.] As seen in FIG. 25A, p14A also protected mice from lethal challenge with SEA. As was shown by the present invention, the antagonist peptide p12A protected mice from death induced by SEB (FIGS 16, 17 and 22) or TSST-1 (FIG. 19), which exhibits only 7% and 6% overall sequence homology with SEA and SEB, respectively.

Figure 25:
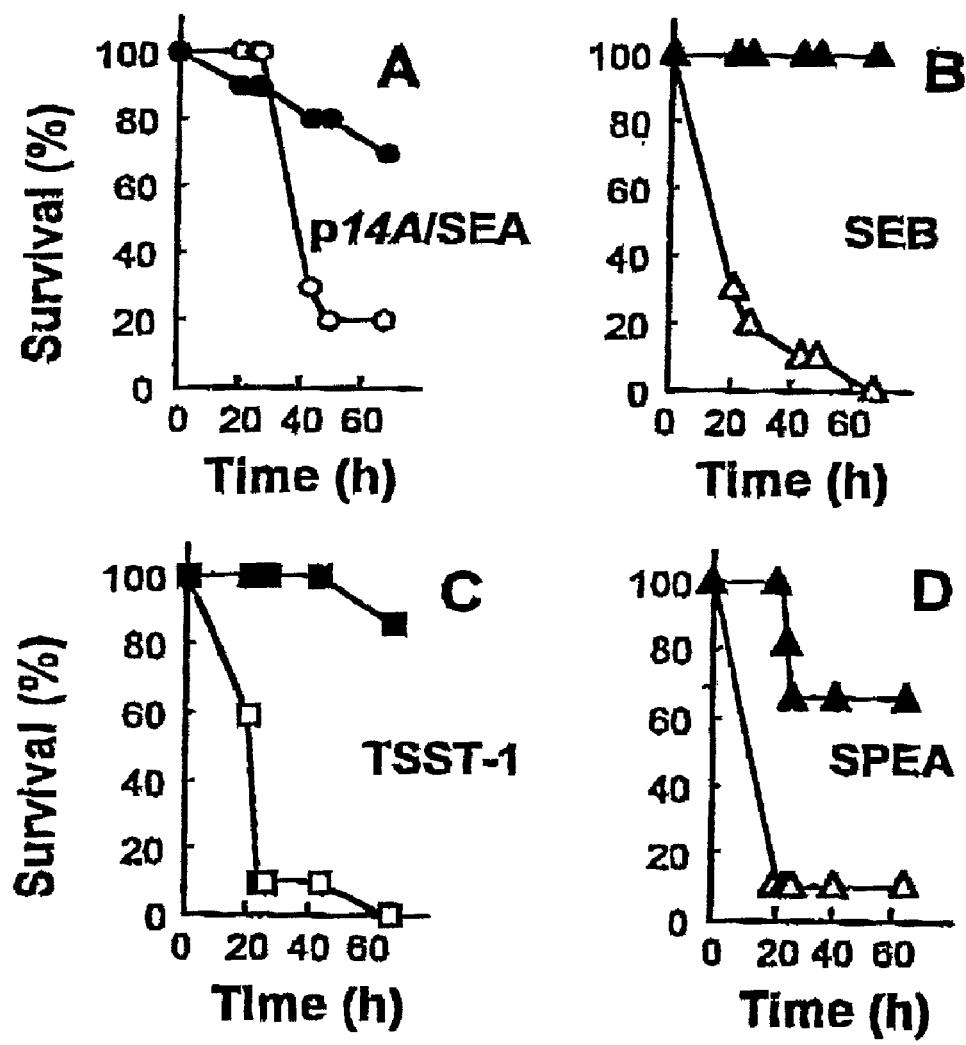
FIGS. 25A–D show mice protected by antagonist rapidly develop broad-spectrum immunity to lethal shock. (A) Ten BALB/c mice received p14A 30 min before sensitization with 20 mg D-Galactosamine and simultaneous challenge with 10 μg SEA (filled circles). Without further injection of p14A, the seven survivors were rechallenged after 2 weeks with 10 μg SEB (filled triangles; B) and 2 weeks later, with 10 μg TSST-1 (filled squares; C) and then, 2 weeks later, with 15 μg SPEA (filled triangles; D). At each challenge, 10 sensitized, naive mice served as toxin controls (open circles, open triangles, open squares). All injections were IP.

In the experiment of FIG. 25, seven of the mice that had survived a lethal challenge with SEA owing to protection by p14A (FIG. 25A) were rechallenged 2 weeks later with SEB, this time in the absence of peptide antagonist (FIG. 25B). All of these mice survived, whereas in the control group of 10 mice, none survived SEB exposure. Two weeks later, mice that had survived this second challenge with SEB were exposed once more to yet another superantigen toxin, this time TSST-1, again in the absence of peptide antagonist. Whereas all 10 mice died in the control group, only 1 out of 7 mice died in the treated group that had been challenged with TSST-1 (FIG. 25C). These six survivors were challenged 2 weeks later for a fourth time, now with SPEA. Four out of six of these mice survived, whereas in the control group, only 1 out of 10 mice survived SPEA exposure. Thus, mice that were protected by p14A against SEA-medicated lethal shock had rapidly acquired resistance to subsequent challenges with different pyrogenic exotoxins.

Example 15

Antagonist Peptide Protects Mice from SEA-Induced Lethal Shock

Figure 26:
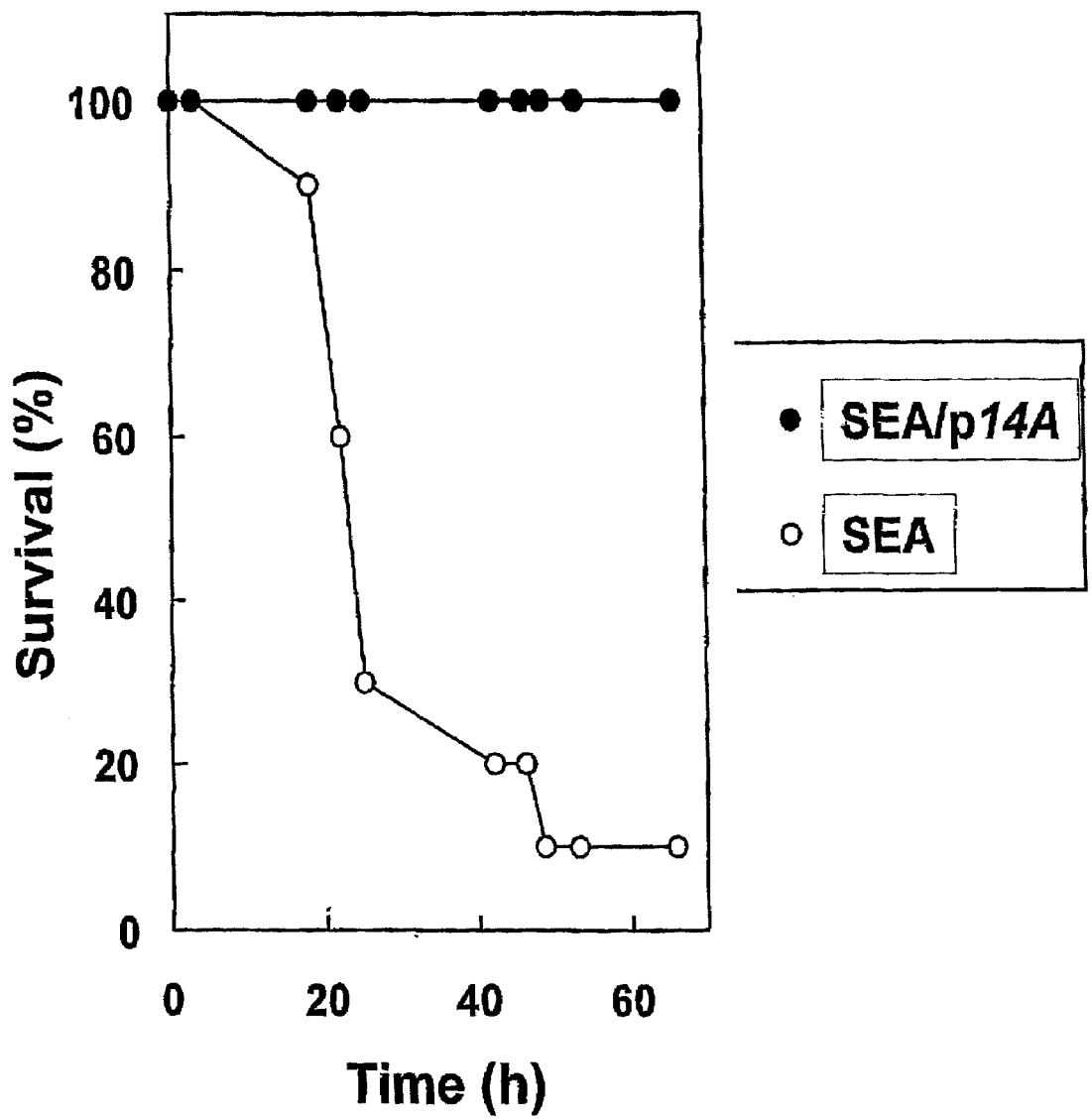
FIG. 26 shows that antagonist peptide protects mice from SEA-induced lethal shock. Groups of 10 BALB/c mice were challenged IP with 10 μg SEA; 25 μg p14A was injected IP 30 min before SEA.
Figure 27:
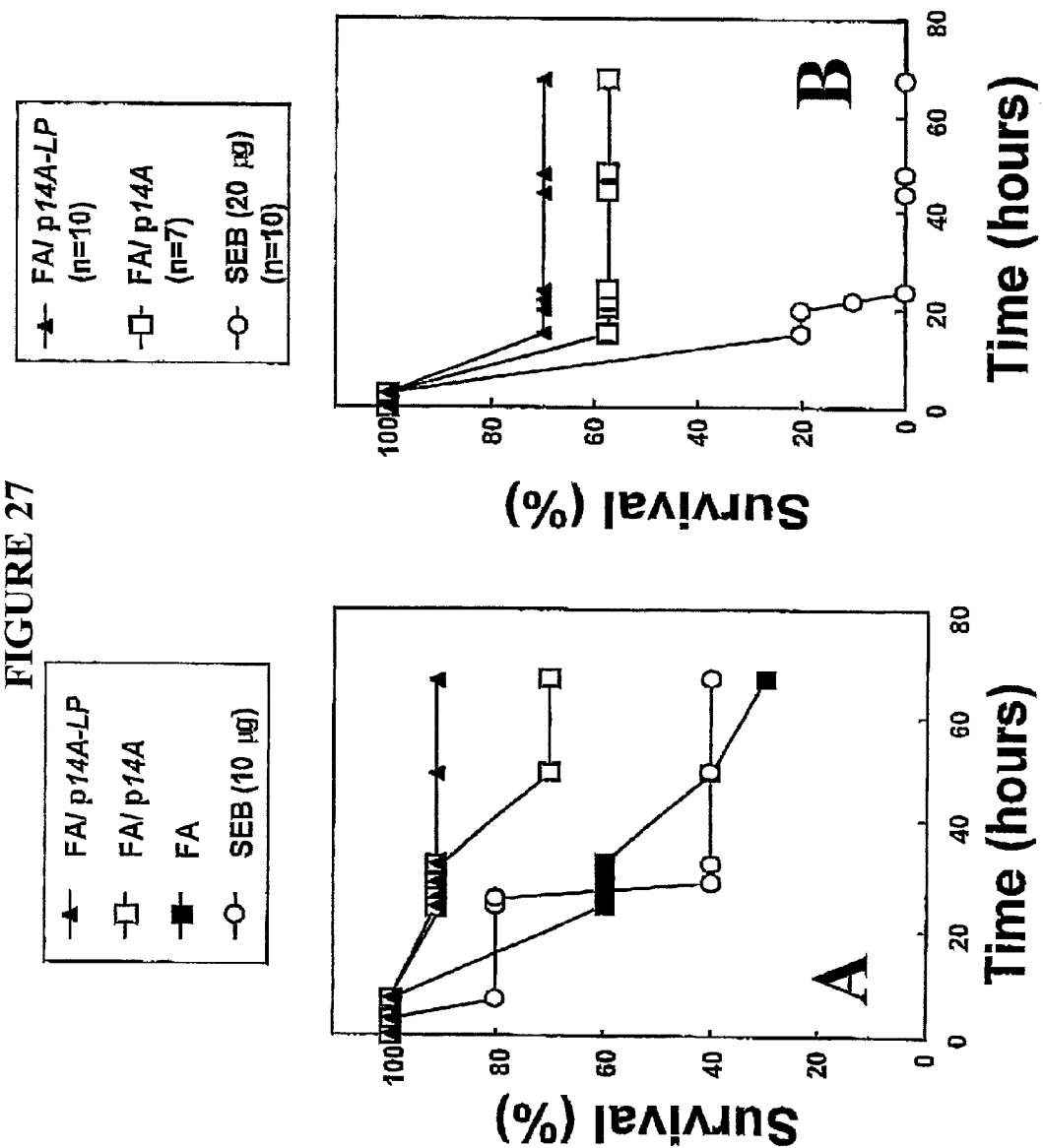
FIGS. 27A–B show that immunization with antagonist peptide protects mice from SEB-induced lethal shock. A: Groups of 10 BALB/c mice (11 mice for p14A-LP) were immunized by three injections (at 0, 2 and 4 weeks) of 10 μg of the indicated peptides in Freund's Adjuvant (FA), and then challenged at 6 weeks by IP injection of 10 μg SEB and 20 mg D-galactosamine. Survival was monitored. B: two weeks after the first challenge, survivors from A (p14A-LP, n=10; p14A, n=7) were rechallenged with 20 μg SEB and 20 mg D-galactosamine. LP, lysyl-palmitoyl. Mice immunized with FA and p14A-LP (filled triangles), with FA and p14A (open squares), or FA alone (filled squares); naive control mice challenged with SEB (open circles).

Mice were injected with p14A 30 min before challenge with SEA. The results are shown in FIG. 26. As may be seen, pre-treatment with the antagonist peptide afforded 100% protection against SEA challenge, compared to only 10% survival of untreated mice after 60 hours. Even though p14A exhibits identity in only 10/14 residues with the corresponding domain in SEA, p14A is an effective antagonist of SEA.

Example 16

Immunization with Antagonist Peptide Protects Mice from SEB-Induced Lethal Shock The inventors have considered the possibility that by anchoring the antagonist peptide into the cell membrane, one might enhance its immunogenicity. p14A was synthesized with a N-terminal lysyl-palmitoyl leader, in which lysine serves as linker and palmitic acid as a hydrophobic anchor, to generate p14A-LP. FIG. 27 shows immunization of mice with p14A-LP and p14A. Ten out of 11 mice immunized with p14A-LP and 7 out of 10 mice immunized with p14A survived lethal SEB challenge, as compared to only 3 out of 10 mice in the control group that was immunized with adjuvant. When the immunized survivors were rechallenged two weeks later, 7 out of the 10 p14A-LP-immunized mice and 4 out of the 7 p14A-immunized mice survived a double dose of SEB; this dose killed 10 out of 10 naive control mice within 24 hours (FIG. 27B). Enzyme-linked immune sorbent assay (ELISA) assays of sera from immunized mice, collected one week after the first challenge with SEB, revealed significant levels of anti-SEB IgM (0.835 units) but very low values for IgM directed against p14A peptide (0.08 units). Moreover, overnight preincubation of these sera with increasing concentrations of p14A, up to 10 μg/ml, did not reduce their ability to bind SEB (0.840 units). Apparently, the antagonist peptide does not compete for the SEB-binding antibodies. It is remarkable that the antagonist peptide elicits anti-SEB antibodies, yet no antibodies against itself are detected. This suggests the affinity of the antagonist peptide for the antibodies it elicits is far lower than the affinity of the toxin. These results show that the anti-toxin vaccine approach using antagonist peptide is productive, including but not limited to the use of a hydrophobic anchor.

Example 17 p14A Protects Pigs from SEA-Induced Incapacitation

Human T cells are at least two orders of magnitude more sensitive to staphylococcal superantigens than murine ones and while humans are sensitive to developing toxic shock syndrome, mice are resistant, apparently because cells that display the most highly reactive Vβ chains of the TCR were deleted from the murine T cell repertoire or the relevant Vβ genes eliminated. Mice thus have acquired a natural resistance to superantigen toxins and must be sensitized before they will undergo toxic shock. Moreover, mice are remote from humans in terms of weight and immune system. It is thus important to demonstrate efficacy of an antagonist also in an animal model closer to man.

The inventors have addressed both issues: toxin incapacitation and use of a higher animal model. Pigs have an immune system similar to humans; thus, between pigs and humans the nucleotide sequence homology of mRNA encoding the Th1 cytokines IL-2 and IFN-γ that mediate shock is in the order of 75–85%, whereas there is no detectable similarity between the human and mouse mRNAs.

Pigs are sensitive to acute superantigen exposure without need for sensitization, and develop incapacitation symptoms similar to those seen in humans. A reproducible pig model for the early incapacitation symptoms of toxic shock that include nausea and vomiting (a neuronal response) as well as severe diarrhea (an intestinal immune response) was established. As may be seen in FIG. 28, antagonist peptide p14A effectively reduces toxin-induced incapacitation.

Using five-day old mixed breed pigs (mainly Yorkshire; 2.5 kg) in randomized groups of 6 piglets for each test condition, each group under its own sow, SEA (25 μg) caused a severe incapacitation that became apparent within 2 h and subsided by 24–36 h, with similar kinetics and intensity whether given by the IV or IP route. IP administration of SEA was used for incapacitation studies in pigs because this route is less traumatizing yet similarly effective to IV. This result confirms that pigs are especially sensitive to SEA [Taylor et al., Infect Immun 36:1263 (1982)]. The reason for this selective sensitivity may be that SEA also uses its beta-grasp to bind the MHC II molecule at an independent second site, binding it far more tightly and allowing crosslinking to occur between MHC II molecules [Hudson et al., J Exp Med 182:711 (1995); Schad et al., EMBO J 14:3292 (1995); Abrahmsen et al., EMBO J 14:2978 (1995)]. The domain targeted by toxin antagonist is remote from both of the binding sites for MHC II and from the binding site for TCR in SEA. Nonetheless, antagonist p14A protected 7 out of 10 mice against death induced by SEA and elicited broad-spectrum protective immunity in the survivors (FIG. 25) and 10 out of 10 SEA-challenged mice in the experiment of FIG. 26.

The following criteria were used to quantitate incapacitation in pigs: vomiting (score of 4); diarrhea, scored for mild (score of 1), regular (score of 2), severe (score of 4), and watery diarrhea (score of 6) (data not shown). Prolonged anorexia and resort to the water spout instead of the sow's teat, apathy and staggering are observed clearly but cannot be quantitated readily; temperature deviations remain on average less than 1° C. from normal controls.

The inventors have shown that p14A is more potent than p12A in terms of its ability to block the action of superantigens in vitro in human PBMC (FIGS. 23 and 24) and in protecting mice against lethal toxic shock (FIG. 22). The p14A antagonist peptide suppressed SEA incapacitation symptoms in pigs (vomiting and diarrhea).

Figure 28:
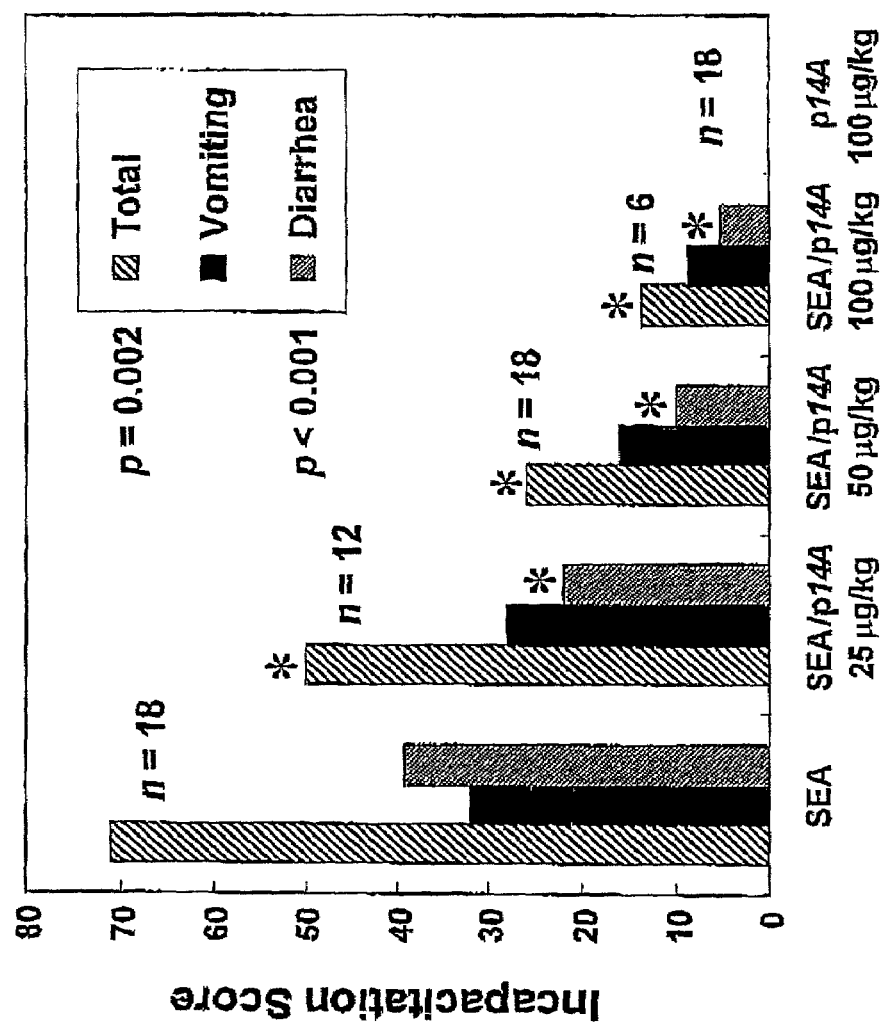
FIG. 28 shows that pyrogenic exotoxin antagonist protects pigs against incapacitation by SEA in a dose-dependent manner. Groups of pigs (total group size, n) were challenged i.p. with 25 μg/kg SEA at 0 h. Where indicated, p14A (25, 50 or 100 μg/kg) was given IP at −0.5 h and at 1, 2, 3, 4 and 5 h post-SEA. Observations were made for that block the harmful action of pyrogenic exotoxins, such as SEB on the human cellular immune response, monitored by the ability of rabbit serum raised against a peptide to inhibit, in PBMC, the induction of IL-2 and IFN-γ mRNA by SEB or by other pyrogenic exotoxins such as TSST-1 or the more related toxin, SEA.

As seen in FIG. 28, with increasing dose of p14A there was a progressive reduction in total incapacitation, as well as in vomiting and in diarrhea. These results were highly significant for total incapacitation (p=0.002) and for diarrhea (p<0.001), which was sustained and occurred largely after the last of 6 antagonist administrations had been made, with post hoc testing significant. Vomiting also decreased in response to antagonist dose.

There were no observable side effects of antagonist peptide alone: a combined group of 18 pigs that received p14A alone failed to develop any symptoms of incapacitation (FIG. 28).

The inventors observed effective suppression of diarrhea by antagonist peptide p14A, which is prolonged in the controls and occurs mainly beyond 5 h (the time of last administration of antagonist peptide in the experimental groups) and up to 24 h; this demonstrates a longer lasting effect of the antagonist peptide.

Figure 29:
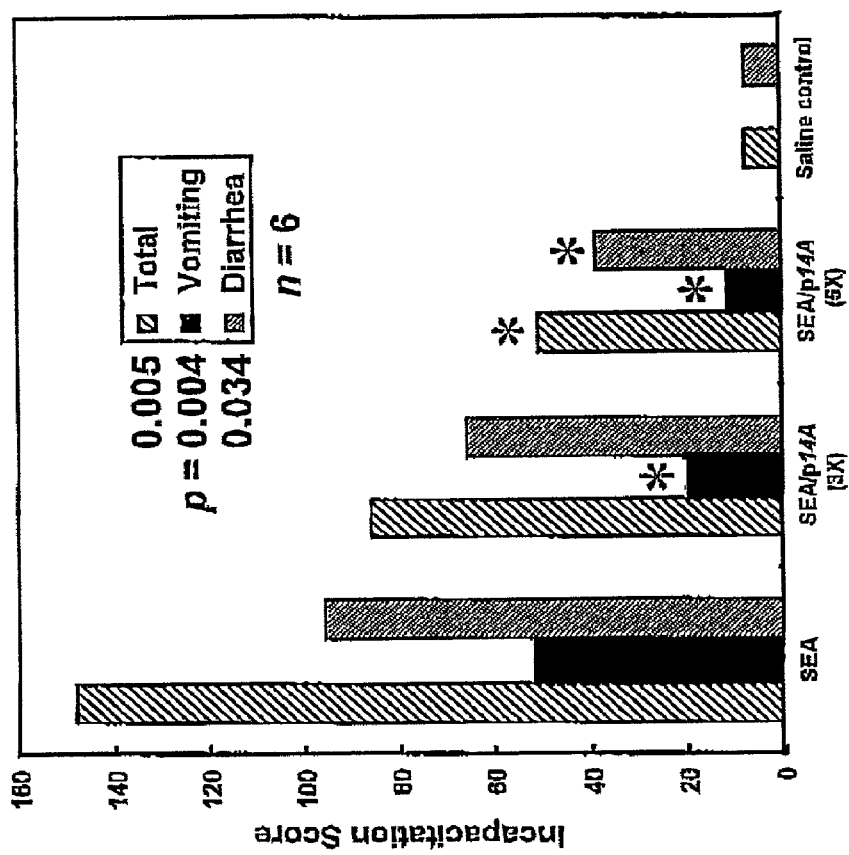

The p14A antagonist peptide suppressed SEA incapacitation symptoms in pigs (vomiting and diarrhea) and its effect increased with number of administrations of antagonist (FIG. 29). This suppression was statistically significant. It is seen that the group of pigs that received 4 administrations of p14A antagonist peptide post-exposure to SEA showed less incapacitation that the group that received only 2 antagonist peptide administrations post-exposure to SEA. Though both of the latter groups had also received a single dose of antagonist peptide at 30 min before exposure to SEA, it is the greater number of post-toxin treatments that gave a greater suppression of incapacitation. These results suggest a potential utility of the antagonist peptide in the treatment of incapacitation symptoms as are seen, for example, in humans during toxic shock and during severe food poisoning.

It has thus been shown that antagonist peptide p14A is able to block the toxic shock symptoms of a superantigen toxin, SEA, not only in mice but also in pigs, an animal whose immune system is more closely related to that of humans, without any detectable toxin agonist activity in vivo.

Example 18

Peptide Antagonist Targets Structurally Conserved Superantigen Domain

The finding of the invention, that a peptide derived from the SEB(150–161) domain exhibits SEB antagonist activity, whereas peptides from regions known to be essential for the interaction of SEB with the TCR and/or MHC class II molecule lacked such activity, drew the inventors attention to the location and conformation of the 12-amino acid 150–161 domain within the structure of SEB. This domain is well-removed from functionally important regions in SEB shown to participate in binding of TCR and/or MHC II (Swaminathan et al. 1992, Nature 359:801–805; Jardetzky et al., 1994, Nature 368:711–718: Li et al., 1998, Immunity 9:807–816; Pagageorgiou et al., 1998, J. Mol. Bio. 277: 61–79; Leder et al., 1998, J Exp Med, 187:823–833) which map into the left half of the molecule (FIG. 30A). Moreover, this domain lies outside the region sufficient for mitogenic activity, the N-terminal 138 amino acids (Buelow et al., 1992, J. Immunol. 148:1–6; Kappler et al., 1992, J. Exp Med. 175:387–389). Thus, the ability of p12(150–161) to act as a SEB antagonist is surprising. The SEB(150–161) domain forms a central turn starting within a β-strand, to an α-helix (FIG. 30A). The sequence in this domain, TNKKKVTAQELD (SEQ ID NO: 1), is conserved among pyrogenic toxins, with 10/12 identities for SEA, SEC1, SEC2, and SPEA, 9/12 for SEE, 5/12 for SPEC and SPEGG and 4/12 for the most remotely related member of the staphylococcal superantigen family, TSST-1 (Hoffmann et al., 1994, Infect. Immun. 62:3396–3407). Although highly homologous with SEB in the 150–161 domain, SEA shows, as stated, only 27% overall sequence homology with SEB; SPEA has 48% homology with SEB and 30% with SEA, and TSST-1 has merely 6% homology with SEB (Betley et al. 1988, J. Bacteriol. 170:34–41). Notwithstanding these differences in overall sequence, the 3-dimensional structures of these superantigens, resolved for SEB, SEA, and TSST-1 by X-ray diffraction and predicted for SPEA, are remarkably similar, especially in there right halves (FIG. 30A). A structurally conserved β-strand-hinge-α-helix domain corresponding to residues 150–161 in SEB is found in each, including TSST-1 (FIG. 30A). Indeed, antagonist peptide p12A inhibits the induction of IL-2 and IFN-γ mRNA by each of SEB, SEA, SPEA, and TSST-1. Thus, the present invention shows that the induction of Th1 cytokine gene expression by a superantigen depends critically on this domain.

The SEB(150–161) domain and its equivalents in SEA, SPEA, and TSST-1 show not only overall spatial conservation (FIG. 30A) but also a remarkable structural similarity (FIG. 30B). In SEB, SEA, and SPEA, this domain forms a pocket in which Thr, Lys, and Glu residues are oriented to allow hydrogen bonding. In TSST-1, the core of this pocket is hydrophobic in character, containing proximal Phe, Leu, and Thr residues, with Lys residue extending away from the pocket.

The sequence of p12(150–161) differs in several positions from the corresponding sequence in SEB. The KK and QELD motifs are spaced equally in both, but p12(150–161) contains the hydrophobic residue Tyr where SEB contains Thr, resembling Phe more closely at this position in TSST-1 (FIG. 30B). Thus, p12(150–161) combined features of the four superantigens in their corresponding domains. The inventors have shown by the present invention that this peptide indeed has broad-spectrum antagonist activity against superantigens, including TSST-1, on human PBMC and in mice.

These examples further describe and demonstrate embodiments within the scope of the present invention. The examples are given solely for the purpose of illustration and are not to be construed as limitations of the present invention, as many variations thereof are possible without departing from the spirit and scope of the invention.

All references cited herein are incorporated herein in their entirety.

The invention claimed is:

1. An isolated and purified peptide comprising the sequence Val-Gln-Tyr-Asn-Lys-Lys-Lys-Ala-Thr-Val-Gln-Glu-Leu-Asp (SEQ ID NO: 13), wherein said isolated peptide does not have toxin agonist activity and is capable of antagonizing toxin-mediated activation of T lymphocytes and/or eliciting protective immunity against toxic shock induced by a pyrogenic exotoxin or by a mixture of pyrogenic exotoxins and protecting against toxic shock induced by a pyrogenic exotoxin or by a mixture of pyrogenic exotoxins.

2. An isolated and purified peptide according to claim 1, comprising a dimer or trimer of said sequence.

3. An isolated and purified peptide according to claim 1, linked to a lauryl-cysteine residue at the N-terminus, linked to a cysteine residue at the C-terminus, or linked to both a lauryl-cysteine residue at the N-terminus and a cysteine residue at the C-terminus.

4. An isolated and purified peptide according to claim 1, linked to other residues suitable for linking the peptide to adjuvants for immunization.

5. An isolated and purified peptide according to claim 1, linked to a D-Ala group at one or both of the N- and C-termini.

6. An isolated and purified peptide according to claim 1, linked to a moiety that can serve as a hydrophobic anchor.

7. An isolated and purified peptide according to claim 6, wherein said linked hydrophobic anchor is a lysyl palmitoyl tail.

8. An isolated and purified peptide according to claim 1, having an N-acetyl group at the N- and/or C-terminus.

9. An isolated and purified peptide according to claim 1, consisting of the peptide of SEQ ID NO: 13.

10. An isolated and purified peptide according to claim 1, consisting of the peptide of SEQ ID NO: 14.

11. An isolated and purified peptide according to claim 1, consisting of the peptide of SEQ ID NO: 15.

12. A pharmaceutical composition comprising a peptide in accordance with any one of claims 1–11 and a pharmaceutically acceptable carrier, diluent, adjuvant and/or excipient.

* * * * *

SEQUENCE LISTING

<160> NUMBER OF SEQ ID NOS: 57

<210> SEQ ID NO 1
<211> LENGTH: 12
<212> TYPE: PRT
<213> ORGANISM: Staphylococcus aureus

<400> SEQUENCE: 1

Thr Asn Lys Lys Lys Val Thr Ala Gln Glu Leu Asp
 1               5                  10

<210> SEQ ID NO 2
<211> LENGTH: 12
<212> TYPE: PRT
<213> ORGANISM: Staphylococcus aureus

<400> SEQUENCE: 2

Tyr Asn Lys Lys Lys Ala Thr Val Gln Glu Leu Asp
 1               5                  10

<210> SEQ ID NO 3
<211> LENGTH: 10
<212> TYPE: PRT
<213> ORGANISM: Staphylococcus aureus

<400> SEQUENCE: 3

Lys Lys Lys Val Thr Ala Gln Glu Leu Asp
 1               5                  10

<210> SEQ ID NO 4
<211> LENGTH: 10
<212> TYPE: PRT
<213> ORGANISM: Staphylococcus aureus

<400> SEQUENCE: 4

Lys Lys Lys Ala Thr Val Gln Glu Leu Asp
 1               5                  10

<210> SEQ ID NO 5
<211> LENGTH: 13
<212> TYPE: PRT
<213> ORGANISM: Staphylococcus aureus
<220> FEATURE:
<221> NAME/KEY: LIPID
<222> LOCATION: (1)...(1)
<223> OTHER INFORMATION: N-lauryl cysteine residue

<400> SEQUENCE: 5

Cys Thr Asn Lys Lys Lys Val Thr Ala Gln Glu Leu Asp
 1               5                  10

<210> SEQ ID NO 6
<211> LENGTH: 13
<212> TYPE: PRT
<213> ORGANISM: Staphylococcus aureus
<220> FEATURE:
<221> NAME/KEY: LIPID
<222> LOCATION: (1)...(1)
<223> OTHER INFORMATION: N-lauryl cysteine residue

<400> SEQUENCE: 6

Cys Tyr Asn Lys Lys Lys Ala Thr Val Gln Glu Leu Asp
 1               5                  10

```
<210> SEQ ID NO 7
<211> LENGTH: 24
<212> TYPE: PRT
<213> ORGANISM: Staphylococcus aureus

<400> SEQUENCE: 7

Tyr Asn Lys Lys Lys Ala Thr Val Gln Glu Leu Asp Tyr Asn Lys Lys
1               5                   10                  15

Lys Ala Thr Val Gln Glu Leu Asp
            20

<210> SEQ ID NO 8
<211> LENGTH: 36
<212> TYPE: PRT
<213> ORGANISM: Staphylococcus aureus

<400> SEQUENCE: 8

Tyr Asn Lys Lys Lys Ala Thr Val Gln Glu Leu Asp Tyr Asn Lys Lys
1               5                   10                  15

Lys Ala Thr Val Gln Glu Leu Asp Tyr Asn Lys Lys Lys Ala Thr Val
            20                  25                  30

Gln Glu Leu Asp
        35

<210> SEQ ID NO 9
<211> LENGTH: 14
<212> TYPE: PRT
<213> ORGANISM: Staphylococcus aureus
<220> FEATURE:
<221> NAME/KEY: DISULFID
<222> LOCATION: (1)...(1)
<220> FEATURE:
<221> NAME/KEY: DISULFID
<222> LOCATION: (14)...(14)

<400> SEQUENCE: 9

Cys Tyr Asn Lys Lys Lys Ala Thr Val Gln Glu Leu Asp Cys
1               5                   10

<210> SEQ ID NO 10
<211> LENGTH: 14
<212> TYPE: PRT
<213> ORGANISM: Staphylococcus aureus
<220> FEATURE:
<221> NAME/KEY: MOD_RES
<222> LOCATION: (1)...(1)
<223> OTHER INFORMATION: D-alanine
<220> FEATURE:
<221> NAME/KEY: MOD_RES
<222> LOCATION: (14)...(14)
<223> OTHER INFORMATION: D-alanine

<400> SEQUENCE: 10

Ala Tyr Asn Lys Lys Lys Ala Thr Val Gln Glu Leu Asp Ala
1               5                   10

<210> SEQ ID NO 11
<211> LENGTH: 13
<212> TYPE: PRT
<213> ORGANISM: Staphylococcus aureus
<220> FEATURE:
<221> NAME/KEY: ACETYLATION
<222> LOCATION: (1)...(1)
<220> FEATURE:
<221> NAME/KEY: MOD_RES
<222> LOCATION: (13)...(13)
<223> OTHER INFORMATION: D-alanine
```

```
<400> SEQUENCE: 11

Tyr Asn Lys Lys Lys Ala Thr Val Gln Glu Leu Asp Ala
1               5                   10

<210> SEQ ID NO 12
<211> LENGTH: 239
<212> TYPE: PRT
<213> ORGANISM: Staphylococcus aureus

<400> SEQUENCE: 12

Glu Ser Gln Pro Asp Pro Lys Pro Asp Glu Leu His Lys Ser Ser Lys
1               5                   10                  15

Phe Thr Gly Leu Met Glu Asn Met Lys Val Leu Tyr Asp Asp Asn His
            20                  25                  30

Val Ser Ala Ile Asn Val Lys Ser Ile Asp Gln Phe Leu Tyr Phe Asp
        35                  40                  45

Leu Ile Tyr Ser Ile Lys Asp Thr Lys Leu Gly Asn Tyr Asp Asn Val
    50                  55                  60

Arg Val Glu Phe Lys Asn Lys Asp Leu Ala Asp Lys Tyr Lys Asp Lys
65                  70                  75                  80

Tyr Val Asp Val Phe Gly Ala Asn Tyr Tyr Gln Cys Tyr Phe Ser
                85                  90                  95

Lys Lys Thr Asn Asp Ile Asn Ser His Glu Thr Asp Lys Arg Lys Thr
            100                 105                 110

Cys Met Tyr Gly Gly Val Thr Glu His Asn Gly Asn Gln Leu Asp Lys
            115                 120                 125

Tyr Arg Ser Ile Thr Val Arg Val Phe Glu Asp Gly Lys Asn Leu Leu
    130                 135                 140

Ser Phe Asp Val Gln Thr Asn Lys Lys Val Thr Ala Gln Glu Leu
145                 150                 155                 160

Asp Tyr Leu Thr Arg His Tyr Leu Val Lys Asn Lys Lys Leu Tyr Glu
                165                 170                 175

Phe Asn Asn Ser Pro Tyr Glu Thr Gly Tyr Ile Lys Phe Ile Glu Asn
            180                 185                 190

Glu Asn Ser Phe Trp Tyr Asp Met Met Pro Ala Pro Gly Asp Lys Phe
        195                 200                 205

Asp Gln Ser Lys Tyr Leu Met Met Tyr Asn Asp Asn Lys Met Val Asp
    210                 215                 220

Ser Lys Asp Val Lys Ile Glu Val Tyr Leu Thr Thr Lys Lys Lys
225                 230                 235

<210> SEQ ID NO 13
<211> LENGTH: 14
<212> TYPE: PRT
<213> ORGANISM: Staphylococcus aureus

<400> SEQUENCE: 13

Val Gln Tyr Asn Lys Lys Lys Ala Thr Val Gln Glu Leu Asp
1               5                   10

<210> SEQ ID NO 14
<211> LENGTH: 16
<212> TYPE: PRT
<213> ORGANISM: Staphylococcus aureus
<220> FEATURE:
<221> NAME/KEY: MOD_RES
<222> LOCATION: (1)...(1)
<223> OTHER INFORMATION: D-alanine
<220> FEATURE:
```

```
<221> NAME/KEY: MOD_RES
<222> LOCATION: (16)...(16)
<223> OTHER INFORMATION: D-alanine

<400> SEQUENCE: 14

Ala Val Gln Tyr Asn Lys Lys Lys Ala Thr Val Gln Glu Leu Asp Ala
 1               5                  10                  15

<210> SEQ ID NO 15
<211> LENGTH: 14
<212> TYPE: PRT
<213> ORGANISM: Staphylococcus aureus
<220> FEATURE:
<221> NAME/KEY: LIPID
<222> LOCATION: (1)...(1)
<223> OTHER INFORMATION: N-lysyl-palmitoylated residue

<400> SEQUENCE: 15

Val Gln Tyr Asn Lys Lys Lys Ala Thr Val Gln Glu Leu Asp
 1               5                  10

<210> SEQ ID NO 16
<211> LENGTH: 12
<212> TYPE: PRT
<213> ORGANISM: Staphylococcus aureus

<400> SEQUENCE: 16

Lys Ser Ser Lys Phe Thr Gly Leu Met Glu Asn Met
 1               5                  10

<210> SEQ ID NO 17
<211> LENGTH: 21
<212> TYPE: PRT
<213> ORGANISM: Staphylococcus aureus

<400> SEQUENCE: 17

Lys Ser Ser Lys Phe Thr Gly Leu Met Glu Asn Met Lys Val Leu Tyr
 1               5                  10                  15

Asp Asp Asn His Val
            20

<210> SEQ ID NO 18
<211> LENGTH: 13
<212> TYPE: PRT
<213> ORGANISM: Staphylococcus aureus

<400> SEQUENCE: 18

Met Glu Asn Met Lys Val Leu Tyr Asp Asp Asn His Val
 1               5                  10

<210> SEQ ID NO 19
<211> LENGTH: 13
<212> TYPE: PRT
<213> ORGANISM: Staphylococcus aureus

<400> SEQUENCE: 19

Ile Asp Gln Phe Leu Tyr Phe Asp Leu Ile Tyr Ser Ile
 1               5                  10

<210> SEQ ID NO 20
<211> LENGTH: 21
<212> TYPE: PRT
<213> ORGANISM: Staphylococcus aureus

<400> SEQUENCE: 20
```

-continued

Ile Asp Gln Phe Leu Tyr Phe Asp Leu Ile Tyr Ser Ile Lys Asp Thr
1               5                   10                  15

Lys Leu Gly Asn Tyr
            20

<210> SEQ ID NO 21
<211> LENGTH: 11
<212> TYPE: PRT
<213> ORGANISM: Staphylococcus aureus

<400> SEQUENCE: 21

Tyr Ser Ile Lys Asp Thr Lys Leu Gly Asn Tyr
1               5                   10

<210> SEQ ID NO 22
<211> LENGTH: 9
<212> TYPE: PRT
<213> ORGANISM: Staphylococcus aureus

<400> SEQUENCE: 22

Ile Lys Asp Thr Lys Leu Gly Asn Tyr
1               5

<210> SEQ ID NO 23
<211> LENGTH: 12
<212> TYPE: PRT
<213> ORGANISM: Staphylococcus aureus

<400> SEQUENCE: 23

Tyr Val Asp Val Phe Gly Ala Asn Tyr Tyr Tyr Gln
1               5                   10

<210> SEQ ID NO 24
<211> LENGTH: 13
<212> TYPE: PRT
<213> ORGANISM: Staphylococcus aureus

<400> SEQUENCE: 24

Tyr Val Asp Val Phe Gly Ala Asn Tyr Tyr Tyr Gln Cys
1               5                   10

<210> SEQ ID NO 25
<211> LENGTH: 11
<212> TYPE: PRT
<213> ORGANISM: Staphylococcus aureus

<400> SEQUENCE: 25

Phe Asp Gln Ser Lys Tyr Leu Met Met Tyr Asn
1               5                   10

<210> SEQ ID NO 26
<211> LENGTH: 14
<212> TYPE: PRT
<213> ORGANISM: Streptococcus pyogenes

<400> SEQUENCE: 26

Ile Glu Thr Asn Lys Lys Met Val Thr Ala Gln Glu Leu Asp
1               5                   10

<210> SEQ ID NO 27
<211> LENGTH: 14
<212> TYPE: PRT
<213> ORGANISM: Streptococcus pyogenes

<400> SEQUENCE: 27

```
Ile Glu Thr Asn Lys Lys Met Val Thr Ala Gln Glu Leu Asp
 1               5                  10
```

<210> SEQ ID NO 28
<211> LENGTH: 14
<212> TYPE: PRT
<213> ORGANISM: Streptococcus pyogenes

<400> SEQUENCE: 28

```
Ile Ile Leu Glu Lys Asp Ile Val Thr Phe Gln Glu Ile Asp
 1               5                  10
```

<210> SEQ ID NO 29
<211> LENGTH: 14
<212> TYPE: PRT
<213> ORGANISM: Streptococcus pyogenes

<400> SEQUENCE: 29

```
Val Arg Ile Lys Lys Lys Gln Phe Thr Leu Gln Glu Phe Asp
 1               5                  10
```

<210> SEQ ID NO 30
<211> LENGTH: 14
<212> TYPE: PRT
<213> ORGANISM: Streptococcus pyogenes

<400> SEQUENCE: 30

```
Ile Thr Val Asn Lys Pro Lys Val Thr Ala Gln Glu Val Asp
 1               5                  10
```

<210> SEQ ID NO 31
<211> LENGTH: 14
<212> TYPE: PRT
<213> ORGANISM: Streptococcus pyogenes

<400> SEQUENCE: 31

```
Val Ser Thr Asp Lys Lys Glu Val Thr Ile Gln Glu Leu Asp
 1               5                  10
```

<210> SEQ ID NO 32
<211> LENGTH: 14
<212> TYPE: PRT
<213> ORGANISM: Streptococcus pyogenes

<400> SEQUENCE: 32

```
Ile Lys Ile Asp Lys Pro Ile Phe Thr Ile Gln Glu Phe Asp
 1               5                  10
```

<210> SEQ ID NO 33
<211> LENGTH: 14
<212> TYPE: PRT
<213> ORGANISM: Streptococcus pyogenes

<400> SEQUENCE: 33

```
Ile Ser Thr Asn Lys Thr Thr Val Thr Ala Gln Glu Ile Asp
 1               5                  10
```

<210> SEQ ID NO 34
<211> LENGTH: 14
<212> TYPE: PRT
<213> ORGANISM: Streptococcus pyogenes

<400> SEQUENCE: 34

```
Ile Leu Ile Lys His Lys Gln Phe Thr Leu Gln Glu Phe Asp
```

<210> SEQ ID NO 35
<211> LENGTH: 14
<212> TYPE: PRT
<213> ORGANISM: Staphylococcus aureus

<400> SEQUENCE: 35

Val Lys Thr Asn Lys Lys Asn Val Thr Val Gln Glu Leu Asp
1               5                   10

<210> SEQ ID NO 36
<211> LENGTH: 14
<212> TYPE: PRT
<213> ORGANISM: Staphylococcus aureus

<400> SEQUENCE: 36

Val Gln Thr Asn Lys Lys Val Thr Ala Gln Glu Leu Asp
1               5                   10

<210> SEQ ID NO 37
<211> LENGTH: 14
<212> TYPE: PRT
<213> ORGANISM: Staphylococcus aureus

<400> SEQUENCE: 37

Val Gln Thr Asp Lys Lys Ser Val Thr Ala Gln Glu Leu Asp
1               5                   10

<210> SEQ ID NO 38
<211> LENGTH: 14
<212> TYPE: PRT
<213> ORGANISM: Staphylococcus aureus

<400> SEQUENCE: 38

Val Gln Thr Asp Lys Lys Asn Val Thr Val Gln Glu Leu Asp
1               5                   10

<210> SEQ ID NO 39
<211> LENGTH: 14
<212> TYPE: PRT
<213> ORGANISM: Staphylococcus aureus

<400> SEQUENCE: 39

Val Lys Thr Ser Lys Lys Glu Val Thr Val Gln Glu Leu Asp
1               5                   10

<210> SEQ ID NO 40
<211> LENGTH: 14
<212> TYPE: PRT
<213> ORGANISM: Staphylococcus aureus

<400> SEQUENCE: 40

Ile Thr Thr Asn Lys Asn Met Val Thr Ile Gln Glu Leu Asp
1               5                   10

<210> SEQ ID NO 41
<211> LENGTH: 14
<212> TYPE: PRT
<213> ORGANISM: Staphylococcus aureus

<400> SEQUENCE: 41

Ile Arg Thr Asn Lys Lys Asn Val Thr Leu Gln Glu Leu Asp
1               5                   10

```
<210> SEQ ID NO 42
<211> LENGTH: 14
<212> TYPE: PRT
<213> ORGANISM: Staphylococcus aureus

<400> SEQUENCE: 42

Ile Ala Thr Asn Lys Lys Leu Val Thr Ala Gln Glu Ile Asp
 1               5                  10

<210> SEQ ID NO 43
<211> LENGTH: 14
<212> TYPE: PRT
<213> ORGANISM: Staphylococcus aureus

<400> SEQUENCE: 43

Val Lys Thr Asn Lys Lys Lys Val Thr Ile Gln Glu Leu Asp
 1               5                  10

<210> SEQ ID NO 44
<211> LENGTH: 14
<212> TYPE: PRT
<213> ORGANISM: Staphylococcus aureus

<400> SEQUENCE: 44

Thr Asp Thr Asp Lys Lys Met Val Thr Ala Gln Glu Ile Asp
 1               5                  10

<210> SEQ ID NO 45
<211> LENGTH: 14
<212> TYPE: PRT
<213> ORGANISM: Staphylococcus aureus

<400> SEQUENCE: 45

Val Ser Thr Asn Lys Lys Leu Val Thr Ala Gln Glu Ile Asp
 1               5                  10

<210> SEQ ID NO 46
<211> LENGTH: 14
<212> TYPE: PRT
<213> ORGANISM: Staphylococcus aureus

<400> SEQUENCE: 46

Ile Lys Thr Lys Lys Ala Lys Val Thr Val Gln Glu Leu Asp
 1               5                  10

<210> SEQ ID NO 47
<211> LENGTH: 14
<212> TYPE: PRT
<213> ORGANISM: Staphylococcus aureus

<400> SEQUENCE: 47

Val Thr Thr Asp Lys Lys Lys Val Thr Ala Gln Glu Leu Asp
 1               5                  10

<210> SEQ ID NO 48
<211> LENGTH: 14
<212> TYPE: PRT
<213> ORGANISM: Staphylococcus aureus

<400> SEQUENCE: 48

Val Lys Thr Asn Lys Lys Glu Val Thr Val Gln Glu Leu Asp
 1               5                  10

<210> SEQ ID NO 49
```

```
<211> LENGTH: 14
<212> TYPE: PRT
<213> ORGANISM: Staphylococcus aureus

<400> SEQUENCE: 49

Pro Lys Phe Asp Lys Lys Gln Leu Ala Ile Ser Thr Leu Asp
1               5                   10

<210> SEQ ID NO 50
<211> LENGTH: 14
<212> TYPE: PRT
<213> ORGANISM: Staphylococcus aureus

<400> SEQUENCE: 50

Val Gln Thr Asn Lys Lys Val Thr Ala Gln Glu Leu Asp
1               5                   10

<210> SEQ ID NO 51
<211> LENGTH: 12
<212> TYPE: PRT
<213> ORGANISM: Staphylococcus aureus

<400> SEQUENCE: 51

Thr Asn Lys Lys Asn Val Thr Val Gln Glu Leu Asp
1               5                   10

<210> SEQ ID NO 52
<211> LENGTH: 12
<212> TYPE: PRT
<213> ORGANISM: Streptococcus pyogenes

<400> SEQUENCE: 52

Thr Asp Lys Lys Met Val Thr Ala Gln Glu Leu Asp
1               5                   10

<210> SEQ ID NO 53
<211> LENGTH: 12
<212> TYPE: PRT
<213> ORGANISM: Staphylococcus aureus

<400> SEQUENCE: 53

Phe Asp Lys Lys Gln Leu Ala Ile Ser Thr Leu Asp
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Consensus sequence
<220> FEATURE:
<221> NAME/KEY: UNSURE
<222> LOCATION: (1)...(1)
<223> OTHER INFORMATION: Any amino acid
<220> FEATURE:
<221> NAME/KEY: UNSURE
<222> LOCATION: (1)...(1)
<223> OTHER INFORMATION: Variable number of amino acid residues from
      1 to 10
<220> FEATURE:
<221> NAME/KEY: UNSURE
<222> LOCATION: (3)...(10)
<223> OTHER INFORMATION: Any amino acid

<400> SEQUENCE: 54

Xaa Lys Xaa Xaa Xaa Xaa Xaa Xaa Xaa Xaa Asp
1               5                   10
```

```
<210> SEQ ID NO 55
<211> LENGTH: 11
<212> TYPE: PRT
<213> ORGANISM: Artificial Sequence
<220> FEATURE:
<223> OTHER INFORMATION: Consensus sequence
<220> FEATURE:
<221> NAME/KEY: UNSURE
<222> LOCATION: (1)...(1)
<223> OTHER INFORMATION: Any amino acid
<220> FEATURE:
<221> NAME/KEY: UNSURE
<222> LOCATION: (1)...(1)
<223> OTHER INFORMATION: Variable number of amino acid residues from
      1 to 10
<220> FEATURE:
<221> NAME/KEY: UNSURE
<222> LOCATION: (3)...(5)
<223> OTHER INFORMATION: Any amino acid
<220> FEATURE:
<221> NAME/KEY: UNSURE
<222> LOCATION: (7)...(7)
<223> OTHER INFORMATION: Any amino acid
<220> FEATURE:
<221> NAME/KEY: UNSURE
<222> LOCATION: (10)...(10)
<223> OTHER INFORMATION: Any amino acid

<400> SEQUENCE: 55

Xaa Lys Xaa Xaa Xaa Thr Xaa Gln Glu Xaa Asp
 1               5                   10

<210> SEQ ID NO 56
<211> LENGTH: 11
<212> TYPE: PRT
<213> ORGANISM: Artificial Sequence
<220> FEATURE:
<223> OTHER INFORMATION: Consensus sequence
<220> FEATURE:
<221> NAME/KEY: UNSURE
<222> LOCATION: (1)...(1)
<223> OTHER INFORMATION: Any amino acid
<220> FEATURE:
<221> NAME/KEY: UNSURE
<222> LOCATION: (1)...(1)
<223> OTHER INFORMATION: Variable number of amino acid from 1 to 10
<220> FEATURE:
<221> NAME/KEY: UNSURE
<222> LOCATION: (4)...(9)
<223> OTHER INFORMATION: Any amino acid

<400> SEQUENCE: 56

Xaa Lys Lys Xaa Xaa Xaa Xaa Xaa Xaa Leu Asp
 1               5                   10

<210> SEQ ID NO 57
<211> LENGTH: 10
<212> TYPE: PRT
<213> ORGANISM: Artificial Sequence
<220> FEATURE:
<223> OTHER INFORMATION: Consensus sequence
<220> FEATURE:
<221> NAME/KEY: UNSURE
<222> LOCATION: (1)...(1)
<223> OTHER INFORMATION: Any charged amino acid
<220> FEATURE:
<221> NAME/KEY: UNSURE
<222> LOCATION: (2)...(3)
<223> OTHER INFORMATION: Any amino acid
<220> FEATURE:
<221> NAME/KEY: UNSURE
<222> LOCATION: (4)...(4)
<223> OTHER INFORMATION: Any hydrophobic amino acid
<220> FEATURE:
```

```
<221> NAME/KEY: UNSURE
<222> LOCATION: (5)...(5)
<223> OTHER INFORMATION: Any amino acid
<220> FEATURE:
<221> NAME/KEY: UNSURE
<222> LOCATION: (6)...(6)
<223> OTHER INFORMATION: Any hydrophobic amino acid
<220> FEATURE:
<221> NAME/KEY: UNSURE
<222> LOCATION: (7)...(8)
<223> OTHER INFORMATION: Any polar amino acid
<220> FEATURE:
<221> NAME/KEY: UNSURE
<222> LOCATION: (9)...(9)
<223> OTHER INFORMATION: Any hydrophobic amino acid

<400> SEQUENCE: 57

Xaa Xaa Xaa Xaa Xaa Xaa Xaa Xaa Xaa Asp
 1               5                   10
```